United States Patent
Von Melchner et al.

(10) Patent No.: US 9,085,767 B2
(45) Date of Patent: Jul. 21, 2015

(54) ENHANCER-CONTAINING GENE TRAP VECTORS FOR RANDOM AND TARGETED GENE TRAPPING

(75) Inventors: Harald Von Melchner, Kronberg/Taunus (DE); Frank Schnütgen, Alzenau (DE); Wolfgang Wurst, München (DE); Patricia Ruiz, Berlin (DE)

(73) Assignees: FRANKGEN BIOTECHNOLOGIE AG, Kronberg (DE); GSF FORSCHUNGSZENTRUM FUR UMWELT UND GESUNDHEIT GMBH, Neuherberg (DE); MPG MAX-PLANCK-GESELLSCHAFT ZUR FORDERUNG DER WISSENSCHAFTEN E.V., Munich (DE)

( * ) Notice: Subject to any disclaimer, the term of this patent is extended or adjusted under 35 U.S.C. 154(b) by 1617 days.

(21) Appl. No.: 11/720,227

(22) PCT Filed: Nov. 28, 2005

(86) PCT No.: PCT/EP2005/056278
§ 371 (c)(1), (2), (4) Date: Aug. 3, 2007

(87) PCT Pub. No.: WO2006/056615
PCT Pub. Date: Jun. 1, 2006

(65) Prior Publication Data
US 2010/0199360 A1    Aug. 5, 2010

(30) Foreign Application Priority Data
Nov. 26, 2004 (EP) .................................... 04028194

(51) Int. Cl.
| | |
|---|---|
| *C12N 15/86* | (2006.01) |
| *C12N 15/867* | (2006.01) |
| *C12N 15/65* | (2006.01) |
| *C12N 15/90* | (2006.01) |
| *C12N 15/10* | (2006.01) |

(52) U.S. Cl.
CPC .. *C12N 15/1051* (2013.01); *C12N 2740/13043* (2013.01); *C12N 2800/30* (2013.01); *C12N 2800/60* (2013.01)

(58) Field of Classification Search
None
See application file for complete search history.

(56) References Cited

U.S. PATENT DOCUMENTS

| | | | | |
|---|---|---|---|---|
| 2002/0194635 A1* | 12/2002 | Dunne et al. | ..................... | 800/15 |
| 2004/0137490 A1* | 7/2004 | Finney et al. | ..................... | 435/6 |
| 2004/0137572 A1* | 7/2004 | Finney et al. | ................. | 435/69.1 |
| 2004/0191873 A1* | 9/2004 | Young et al. | ................. | 435/91.2 |
| 2004/0221330 A1* | 11/2004 | Klimyuk et al. | .............. | 800/278 |
| 2005/0214793 A1* | 9/2005 | Lawn et al. | ....................... | 435/6 |
| 2008/0104723 A1* | 5/2008 | Takeda et al. | ................... | 800/25 |
| 2013/0205421 A1* | 8/2013 | Petolino et al. | ................ | 800/260 |

OTHER PUBLICATIONS

Wahlers et al, In Vivo Analysis of Retroviral Enhancer Mutations in Hematopoietic Cells: SP1/EGR1 and ETS/GATA Motifs Contribute to Long Terminal Repeat Specificity, Journal of Virology, Jan. 2002, pp. 303-312.*
Baghdoyan et al, Capture of cytokine-responsive genes (NACA and RBM3) using a gene trap approach, Blood, Jun. 15, 2000, 95 (12), pp. 3750-3757.*
Zambrowicz et al, Disruption and sequence identification of 2,000 genes in mouse embryonic stem cells, Nature, vol. 392, Apr. 9, 1998, pp. 608-611.*
De Palma et al, Blood, 2005, Promoter trapping reveals significant differences in integration site selection between MLV and HIV vectors in primary hematopoietic cells, p. 2307-2315.*
Groskreutz et al, Increased Expression and Convenience with the New pGL3 Luciferase Reporter Vectors, Promega Notes Magazine No. 50, 1995, p. 1-5.*

* cited by examiner

*Primary Examiner* — Maria Marvich
(74) *Attorney, Agent, or Firm* — Norris McLaughlin & Marcus, P.A.

(57) ABSTRACT

The present invention relates to a novel class of gene trap vector (enhanced gene trap vectors, eGTV) for efficiently identifying silent or weakly expressed target genes in mammalian genomes, methods of their production and methods for identifying and mutating target genes by using the enhanced gene trap vectors. The gene trap vectors of the present invention can also be used for inducing the expression of silent genes and enhancing the expression of weakly expressed genes. The use of the enhanced gene trap vectors for creating transgenic organisms to identify gene function and to validate pharmaceutical compounds prior to clinical applications is a further aspect of the present invention.

19 Claims, 5 Drawing Sheets

SEQUENCE LISTING

```
<160> NUMBER OF SEQ ID NOS: 33

<210> SEQ ID NO 1
<211> LENGTH: 8586
<212> TYPE: DNA
<213> ORGANISM: Artificial
<220> FEATURE:
<223> OTHER INFORMATION: Retroviral vector FlipROSAbetaGeo(int)

<400> SEQUENCE: 1
ctgcagcctg aatatgggcc aaacaggata tctgtggtaa gcagttcctg ccccggctca      60
gggccaagaa cagatggaac agctgaatat gggccaaaca ggatatctgt ggtaagcagt     120
tcctgccccg gctcagggcc aagaacagat ggtcccagat gcggtccagc cctcagcag     180 tttctagaga accatcagat gtttccaggg tgccccaagg acctgaaatg accctgtgcc     240
ttatttgaac taaccaatca gttcgcttct cgcttctgtt cgcgcgcttc tgctccccga     300
gctcaataaa agagcccaca acccctcact cggggcgcca gtcctccgat tgactgagtc     360
gcccgggtac ccgtgtatcc aataaaccct cttgcagttg catccgactt gtggtctcgc     420
tgttccttgg gagggtctcc tctgagtgat tgactacccg tcagcggggg tctttcattt     480
gggggctcgt ccgggatcgg gagacccctg cccagggacc accgacccac caccgggagg     540
caagctggcc agcaacttat ctgtgtctgt ccgattgtct agtgtctatg actgatttta     600
tgcgcctgcg tcggtactag ttagctaact agctctgtat ctggcggacc cgtggtggaa     660
ctgacgagtt cggaacaccc ggccgcaacc ctgggagacg tcccagggac ttcgggggcc     720 gttttgtgg cccgacctga gtccaaaaat cccgatcgtt ttggactctt tggtgcaccc     780
cccttagagg agggatatgt ggttctggta ggagacgaga acctaaaaca gttcccgcct     840
```

```
ccgtctgaat ttttgctttc ggtttgggac cgaagccgcg ccgcgcgtct tgtctgctgc    900
agcatcgttc tgtgttgtct ctgtctgact gtgtttctgt atttgtctga gaattagggc    960
cagactgtta ccactccctt aagtttgacc ttaggtcact ggaaagatgt cgagcggatc   1020
gctcacaacc agtcggtaga tgtcaagaag agacgttggg ttaccttctg ctctgcagaa   1080
tggccaacct ttaacgtcgg atggccgcga cacggcacct ttaaccgaga cctcatcacc   1140
caggttaaga tcaaggtctt ttcacctggc ccgcatggac acccagacca ggtcccctac   1200
atcgtgacct gggaagcctt ggcttttgac ccccctccct gggtcaagcc ctttgtacac   1260
cctaagcctc cgcctcctct tcctccatcc gccccgtctc tcccccttga acctcctcgt   1320
tcgaccccgc ctcgatcctc cctttatcca gccctcactc cttctctagg cgccggccgg   1380
atccgttgct gaagttccta ttccgaagtt cctattcttc aaatagtata ggaacttcgt   1440
taacgaagtt cctattccga agttcctatt ctctagaaag tataggaact tctcgtgacg   1500
gtctcgaagc cgcggtgcgg gtgccagggc gtgcccttgg gctccccggg cgcgtactcc   1560
acctcaccca tctggtccac gggatcccag tgtggtggta ctcgaggtcg actctagagg   1620
atcgagcccc agctggttct ttccgtctca gaagccatag agcccaccgc atccccagca   1680
tgcctgctat tgtcttccca atcctccccc ttgctgtcct gccccacccc accccccaga   1740
atagaatgac acctactcag acaatgcgat gcaatttcct cattttatta ggaaaggaca   1800
gtgggagtgg caccttccag ggtcaaggaa ggcacggggg aggggcaaac aacagatggc   1860
tggcaactag aaggcacagt cgaggctgat cagcgagctc tagagaattg atcccctcag   1920
aagaactcgt caagaaggcg atagaaggcg atgcgctgcg aatcgggagc ggcgataccg   1980
taaagcacga ggaagcggtc agcccattcg ccgccaagct cttcagcaat atcacgggta   2040
gccaacgcta tgtcctgata gcggtccgcc acacccagcc ggccacagtc gatgaatcca   2100
gaaaagcggc catttccac catgatattc ggcaagcagg catcgccatg ggtcacgacg   2160
agatcctcgc cgtcgggcat gcgcgccttg agcctggcga acagttcggc tggcgcgagc   2220
ccctgatgct cttcgtccag atcatcctga tcgacaagac cggcttccat ccgagtacgt   2280
gctcgctcga tgcgatgttt cgcttggtgg tcgaatgggc aggtagccgg atcaagcgta   2340
tgcagccgcc gcattgcatc agccatgatg gatactttct cggcaggagc aaggtgagat   2400
gacaggagat cctgccccgg cacttcgccc aatagcagcc agtccttccc gcttcagtg   2460
acaacgtcga gcacagctgc gcaaggaacg cccgtcgtgg ccagccacga tagccgcgct   2520
gcctcgtcct gcagttcatt cagggcaccg gacaggtcgg tcttgacaaa aagaaccggg   2580
cgcccctgcg ctgacagccg gaacacggcg gcatcagagc agccgattgt ctgttgtgcc   2640
cagtcatagc cgaatagcct ctccacccaa gcggccggag aacctgcgtg caatccatct   2700
tgttcaatgg ccgatcccat attggctgca gccggggga tccctgaca ccagaccaac   2760
tggtaatggt agcgaccggc gctcagctgg aattccgccg atactgacgg gctccaggag   2820
tcgtcgccac caatccccat atggaaaccg tcgatattca gccatgtgcc ttcttccgcg   2880
tgcagcagat ggcgatggct ggtttccatc agttgctgtt gactgtagcg gctgatgttg   2940
aactggaagt cgccgcgcca ctggtgtggg ccataattca attcgcgcgt cccgcagcgc   3000
agaccgtttt cgctcgggaa gacgtacggg gtatacatgt ctgacaatgg cagatcccag   3060
cggtcaaaac aggcggcagt aaggcggtcg ggatagtttt cttgcggccc taatccgagc   3120
cagtttaccc gctctgctac ctgcgccagc tggcagttca ggccaatccg cgccggatgc   3180
```

```
ggtgtatcgc tcgccacttc aacatcaacg gtaatcgcca tttgaccact accatcaatc    3240
cggtaggttt tccggctgat aaataaggtt ttcccctgat gctgccacgc gtgagcggtc    3300
gtaatcagca ccgcatcagc aagtgtatct gccgtgcact gcaacaacgc tgcttcggcc    3360
tggtaatggc ccgccgcctt ccagcgttcg acccaggcgt tagggtcaat gcgggtcgct    3420
tcacttacgc caatgtcgtt atccagcggt gcacgggtga actgatcgcg cagcggcgtc    3480
agcagttgtt ttttatcgcc aatccacatc tgtgaaagaa agcctgactg gcggttaaat    3540
tgccaacgct tattacccag ctcgatgcaa aaatccattt cgctggtggt cagatgcggg    3600
atggcgtggg acgcggcggg gagcgtcaca ctgaggtttt ccgccagacg ccactgctgc    3660
caggcgctga tgtgcccggc ttctgaccat gcggtcgcgt tcggttgcac tacgcgtact    3720
gtgagccaga gttgcccggc gctctccggc tgcggtagtt caggcagttc aatcaactgt    3780
ttaccttgtg gagcgacatc cagaggcact tcaccgcttg ccagcggctt accatccagc    3840
gccaccatcc agtgcaggag ctcgttatcg ctatgacgga acaggtattc gctggtcact    3900
tcgatggttt gcccggataa acggaactgg aaaaactgct gctggtgttt tgcttccgtc    3960
agcgctggat gcggcgtgcg gtcggcaaag accagaccgt tcatacagaa ctggcgatcg    4020
ttcggcgtat cgccaaaatc accgccgtaa gccgaccacg ggttgccgtt ttcatcatat    4080
ttaatcagcg actgatccac ccagtcccag acgaagccgc cctgtaaacg gggatactga    4140
cgaaacgcct gccagtattt agcgaaaccg ccaagactgt tacccatcgc gtgggcgtat    4200
tcgcaaagga tcagcgggcg cgtctctcca ggtagcgaaa gccattttt gatggaccat    4260 ttcggcacag ccgggaaggg ctggtcttca tccacgcgcg cgtacatcgg gcaaataata    4320
tcggtggccg tggtgtcggc tccgccgcct tcatactgca ccgggcggga aggatcgaca    4380
gatttgatcc agcgatacag cgcgtcgtga ttagcgccgt ggcctgattc attccccagc    4440
gaccagatga tcacactcgg gtgattacga tcgcgctgca ccattcgcgt tacgcgttcg    4500
ctcatcgccg gtagccagcg cggatcatcg gtcagacgat tcattggcac catgccgtgg    4560
gtttcaatat tggcttcatc caccacatac aggccgtagc ggtcgcacag cgtgtaccac    4620
agcggatggt tcgataatg cgaacagcgc acggcgttaa agttgttctg cttcatcagc    4680
aggatatcct gcaccatcgt ctgctcatcc atgacctgac catgcagagg atgatgctcg    4740
tgacggttaa cgcctcgaat cagcaacggc ttgccgttca gcagcagcag accattttca    4800
atccgcacct cgcggaaacc gacatcgcag gcttctgctt caatcagcgt gccgtcggcg    4860
gtgtgcagtt caaccaccgc acgatagaga ttcgggattt cggcgctcca cagtttcggg    4920
ttttcgacgt tcagacgtag tgtgacgcga tcggcataac caccacgctc atcgataatt    4980
tcaccgccga aaggcgcggt gccgctggcg acctgcgttt caccctgcca taaagaaact    5040
gttacccgta ggtagtcacg caactcgccg cacatctgaa cttcagcctc cagtacagcg    5100
cggctgaaat catcattaaa gcgagtggca acatggaaat cgctgatttg tgtagtcggt    5160
ttatgcagca acgagacgtc acggaaaatg ccgctcatcc gccacatatc ctgatcttcc    5220
agataactgc cgtcactcca acgcagcacc atcaccgcga ggcggttttc tccggcgcgt    5280
aaaaatgcgc tcaggtcaaa ttcagacggc aaacgactgt cctggccgta accgaccag    5340 cgcccgttgc accacagatg aaacgccgag ttaacgccat caaaaataat tcgcgtctgg    5400
ccttcctgta gccagctttc atcaacatta aatgtgagcg agtaacaacc cgtcggattc    5460
tccgtgggaa caaacggcgg attgaccgta atggataggt tacgttggt gtagatgggc    5520 gcatcgtaac cgtgcatctg ccagtttgag gggacgacga cagtatcggc ctcaggaaga    5580
```

```
tcgcactcca gccagctttc cggcaccgct tctggtgccg aaaccaggc aaagcgccat    5640 tcgccattca ggctgcgcaa ctgttgggaa gggcgatcgg tgcgggcctc ttcgctatta    5700
cgccagctgg cgaaagggg atgtgctgca aggcgattaa gttgggtaac gccagggttt    5760
tcccagtcac gacgttgtaa aacgacggga tccgccatgt cacagatcat caagcttatc    5820
gataccgtcg atccccactg aaagaccgc gaagagtttg tcctcaaccg cgagctgtgg    5880 aaaaaaagg gacaggataa gtatgacatc atcaaggaaa ccctggacta ctgcgcccta    5940
cagatctgca gcccggggga tccactagtt ctagcctcga gtaggaattc gtgtcatgtc    6000
ggcgacccta cgccccccaac tgagagaact caaaggttac cccagttggg cactatctc    6060 ccgaaaaccg cttctagcaa cgaagttcct atactatttg aagaatagga acttcggaat    6120
aggaacttca gcagatctgc atcagatacc attagacata cgatagacg atacagatct    6180 gtatcgtcta tcgttatgtg atgcagatct gctgaagttc ctatactttc tagagaatag    6240
gaacttcgga aaggaacttc gaattctcga gggcccgggc tcgaccagct gtgcgcatag    6300
tggcttgaat cgataaaata aaagatttta tttagtctcc agaaaaggg gggaatgaaa    6360 gaccccacct gtaggtttgg caagctagca caaccctca ctcggggcgc cagtcctccg    6420
attgactgag tcgcccgggt acccgtgtat ccaataaacc ctcttgcagt tgcatccgac    6480
ttgtggtctc gctgttcctt gggagggtct cctctgagtg attgactacc cgtcagcggg    6540 ggtcttttcac atgcagcatg tatcaaaatt aatttggttt tttttcttaa gtatttacat    6600
taaatggcca tagttgcatt aatgaatcgg ccaacgcgcg gggagaggcg gtttgcgtat    6660
tgggcgctct tccgcttcct cgctcactga ctcgctgcgc tcggtcgttc ggctgcggcg    6720
agcggtatca gctcactcaa aggcggtaat acggttatcc acagaatcag ggataacgc    6780 aggaaagaac atgtgagcaa aaggccagca aaaggccagg aaccgtaaaa aggccgcgtt    6840
gctggcgttt ttccataggc tccgccccc tgacgagcat cacaaaaatc gacgctcaag    6900
tcagaggtgg cgaaacccga caggactata aagataccag gcgtttcccc ctggaagctc    6960
cctcgtgcgc tctcctgttc cgaccctgcc gcttaccgga tacctgtccg cctttctccc    7020
ttcgggaagc gtggcgcttt ctcatagctc acgctgtagg tatctcagtt cggtgtaggt    7080
cgttcgctcc aagctgggct gtgtgcacga accccccgtt cagcccgacc gctgcgcctt    7140
atccggtaac tatcgtcttg agtccaaccc ggtaagacac gacttatcgc cactggcagc    7200
agccactggt aacaggatta gcagagcgag gtatgtaggc ggtgctacag agttcttgaa    7260
gtggtggcct aactacggct acactagaag gacagtattt ggtatctgcg ctctgctgaa    7320
gccagttacc ttcggaaaaa gagttggtag ctcttgatcc ggcaaacaaa ccaccgctgg    7380
tagcggtggt ttttttgttt gcaagcagca gattacgcgc agaaaaaaag gatctcaaga    7440
agatcctttg atcttttcta cggggtctga cgctcagtgg aacgaaaact cacgttaagg    7500
gattttggtc atgagattat caaaaaggat cttcacctag atcctttgc ggccgcaaat    7560 caatctaaag tatatatgag taaacttggt ctgacagtta ccaatgctta atcagtgagg    7620
cacctatctc agcgatctgt ctatttcgtt catccatagt tgcctgactc cccgtcgtgt    7680
agataactac gatacgggag ggcttaccat ctggccccag tgctgcaatg ataccgcgag    7740
acccacgctc accggctcca gatttatcag caataaacca gccagccgga agggccgagc    7800
gcagaagtgg tcctgcaact ttatccgcct ccatccagtc tattaattgt tgccgggaag    7860
ctagagtaag tagttcgcca gttaatagtt tgcgcaacgt tgttgccatt gctgcaggca    7920
```

| | |
|---|---|
| tcgtggtgtc acgctcgtcg tttggtatgg cttcattcag ctccggttcc caacgatcaa | 7980 |
| ggcgagttac atgatccccc atgttgtgca aaaaagcggt tagctccttc ggtcctccga | 8040 |
| tcgttgtcag aagtaagttg gccgcagtgt tatcactcat ggttatggca gcactgcata | 8100 |
| attctcttac tgtcatgcca tccgtaagat gcttttctgt gactggtgag tactcaacca | 8160 |
| agtcattctg agaatagtgt atgcggcgac cgagttgctc ttgcccggcg tcaatacggg | 8220 |
| ataataccgc gccacatagc agaactttaa aagtgctcat cattggaaaa cgttcttcgg | 8280 |
| ggcgaaaact ctcaaggatc ttaccgctgt tgagatccag ttcgatgtaa cccactcgtg | 8340 |
| cacccaactg atcttcagca tcttttactt tcaccagcgt ttctgggtga gcaaaaacag | 8400 |
| gaaggcaaaa tgccgcaaaa aagggaataa gggcgacacg gaaatgttga atactcatac | 8460 |
| tcttcctttt tcaatattat tgaagcattt atcagggtta ttgtctcatg agcggataca | 8520 |
| tatttgaatg tatttagaaa aataaacaaa taggggttcc gcgcacattt ccccgaaaag | 8580 |
| tgccac | 8586 |

<210> SEQ ID NO 2
<211> LENGTH: 3728
<212> TYPE: DNA
<213> ORGANISM: Artificial
<220> FEATURE:
<223> OTHER INFORMATION: Retroviral vector pBABErfl

<400> SEQUENCE: 2

| | |
|---|---|
| ctgcagcctg aatatgggcc aaacaggata tctgtggtaa gcagttcctg ccccggctca | 60 |
| gggccaagaa cagatggaac agctgaatat gggccaaaca ggatatctgt ggtaagcagt | 120 |
| tcctgccccg gctcagggcc aagaacagat ggtccccaga tgcggtccag ccctcagcag | 180 |
| tttctagaga accatcagat gtttccaggg tgccccaagg acctgaaatg accctgtgcc | 240 |
| ttatttgaac taaccaatca gttcgcttct cgcttctgtt cgcgcgcttc tgctccccga | 300 |
| gctcaataaa agagcccaca acccctcact cggggcgcca gtcctccgat tgactgagtc | 360 |
| gcccgggtac ccgtgtatcc aataaaccct cttgcagttg catccgactt gtggtctcgc | 420 |
| tgttccttgg gagggtctcc tctgagtgat tgactacccg tcagcggggg tctttcattt | 480 |
| gggggctcgt ccgggatcgg gagacccctg cccagggacc accgacccac caccgggagg | 540 |
| caagctggcc agcaacttat ctgtgtctgt ccgattgtct agtgtctatg actgatttta | 600 |
| tgcgcctgcg tcggtactag ttagctaact agctctgtat ctggcggacc cgtggtggaa | 660 |
| ctgacgagtt cggaacaccc ggccgcaacc tggagacg tcccagggac ttcggggcc | 720 |
| gtttttgtgg cccgacctga gtccaaaaat cccgatcgtt ttggactctt tggtgcaccc | 780 |
| cccttagagg agggatatgt ggttctggta ggagacgaga acctaaaaca gttcccgcct | 840 |
| ccgtctgaat ttttgctttc ggtttgggac cgaagccgcg ccgcgcgtct tgtctgctgc | 900 |
| agcatcgttc tgtgttgtct ctgtctgact gtgtttctgt atttgtctga gaattagggc | 960 |
| cagactgtta ccactccctt aagtttgacc ttaggtcact ggaaagatgt cgagcggatc | 1020 |
| gctcacaacc agtcggtaga tgtcaagaag agacgttggg ttaccttctg ctctgcagaa | 1080 |
| tggccaacct ttaacgtcgg atggccgcga cggcaccctt aaccgaga cctcatcacc | 1140 |
| caggttaaga tcaaggtctt tcacctggcc cgcatggac acccagacca ggtccctac | 1200 |
| atcgtgacct gggaagcctt ggcttttgac cccctcct gggtcaagcc ctttgtacac | 1260 |
| cctaagcctc cgcctcctct tcctccatcc gccccgtctc tcccccttga acctcctcgt | 1320 |
| tcgacccgc ctcgatcctc cctttatcca gccctcactc cttctctagg cgccggccgg | 1380 |

```
atcccagtgt ggtggtacgt aggaattctc gagggcccgg gctcgaccag ctgtgcgcat    1440
agtggcttga atcgataaaa taaaagattt tatttagtct ccagaaaaag gggggaatga    1500
aagaccccac ctgtaggttt ggcaagctag cacaacccct cactcggggc gccagtcctc    1560
cgattgactg agtcgcccgg gtacccgtgt atccaataaa ccctcttgca gttgcatccg    1620
acttgtggtc tcgctgttcc ttgggagggt ctcctctgag tgattgacta cccgtcagcg    1680
ggggtctttc acatgcagca tgtatcaaaa ttaatttggt ttttttcttt aagtatttac    1740
attaaatggc catagttgca ttaatgaatc ggccaacgcg cggggagagg cggtttgcgt    1800
attgggcgct cttccgcttc ctcgctcact gactcgctgc gctcggtcgt tcggctgcgg    1860
cgagcggtat cagctcactc aaaggcggta atacggttat ccacagaatc aggggataac    1920
gcaggaaaga acatgtgagc aaaaggccag caaaaggcca ggaaccgtaa aaaggccgcg    1980
ttgctggcgt ttttccatag gctccgcccc cctgacgagc atcacaaaaa tcgacgctca    2040
agtcagaggt ggcgaaaccc gacaggacta taaagatacc aggcgtttcc ccctggaagc    2100
tccctcgtgc gctctcctgt tccgaccctg ccgcttaccg gatacctgtc cgcctttctc    2160
ccttcgggaa gcgtggcgct ttctcatagc tcacgctgta ggtatctcag ttcggtgtag    2220
gtcgttcgct ccaagctggg ctgtgtgcac gaaccccccg ttcagcccga ccgctgcgcc    2280
ttatccggta actatcgtct tgagtccaac ccggtaagac acgacttatc gccactggca    2340
gcagccactg gtaacaggat tagcagagcg aggtatgtag gcggtgctac agagttcttg    2400
aagtggtggc ctaactacgg ctacactaga aggacagtat ttggtatctg cgctctgctg    2460
aagccagtta ccttcggaaa aagagttggt agctcttgat ccggcaaaca aaccaccgct    2520
ggtagcggtg gtttttttgt ttgcaagcag cagattacgc gcagaaaaaa aggatctcaa    2580
gaagatcctt tgatcttttc tacggggtct gacgctcagt ggaacgaaaa ctcacgttaa    2640
gggattttgg tcatgagatt atcaaaaagg atcttcacct agatcctttt gcggccgcaa    2700
atcaatctaa agtatatatg agtaaacttg gtctgacagt taccaatgct taatcagtga    2760
ggcacctatc tcagcgatct gtctatttcg ttcatccata gttgcctgac tccccgtcgt    2820
gtagataact acgatacggg agggcttacc atctggcccc agtgctgcaa tgataccgcg    2880
agacccacgc tcaccggctc cagatttatc agcaataaac cagccagccg aagggccga    2940 gcgcagaagt ggtcctgcaa ctttatccgc ctccatccag tctattaatt gttgccggga    3000
agctagagta agtagttcgc cagttaatag tttgcgcaac gttgttgcca ttgctgcagg    3060
catcgtggtg tcacgctcgt cgtttggtat ggcttcattc agctccggtt cccaacgatc    3120
aaggcgagtt acatgatccc ccatgttgtg caaaaaagcg gttagctcct tcggtcctcc    3180
gatcgttgtc agaagtaagt tggccgcagt gttatcactc atggttatgg cagcactgca    3240
taattctctt actgtcatgc catccgtaag atgcttttct gtgactggtg agtactcaac    3300
caagtcattc tgagaatagt gtatgcggcg accgagttgc tcttgcccgg cgtcaatacg    3360
ggataatacc gcgccacata gcagaacttt aaaagtgctc atcattggaa aacgttcttc    3420
ggggcgaaaa ctctcaagga tcttaccgct gttgagatcc agttcgatgt aacccactcg    3480
tgcacccaac tgatcttcag catctttta ctttcaccagc gtttctgggt gagcaaaaac    3540
aggaaggcaa aatgccgcaa aaagggaat aagggcgaca cggaaatgtt gaatactcat    3600
actcttcctt tttcaatatt attgaagcat ttatcagggt tattgtctca tgagcggata    3660
catatttgaa tgtatttaga aaataaaca aataggggtt ccgcgcacat ttccccgaaa    3720
```

-continued

| | |
|---|---|
| agtgccac | 3728 |

<210> SEQ ID NO 3
<211> LENGTH: 8740
<212> TYPE: DNA
<213> ORGANISM: Artificial
<220> FEATURE:
<223> OTHER INFORMATION: Retroviral gene trap vector FlipROSAbetaGeo

<400> SEQUENCE: 3

| | |
|---|---|
| ctgcagcctg aatatgggcc aaacaggata tctgtggtaa gcagttcctg ccccggctca | 60 |
| gggccaagaa cagatggaac agctgaatat gggccaaaca ggatatctgt ggtaagcagt | 120 |
| tcctgccccg gctcagggcc aagaacagat ggtccccaga tgcggtccag ccctcagcag | 180 |
| tttctagaga accatcagat gtttccaggg tgccccaagg acctgaaatg accctgtgcc | 240 |
| ttatttgaac taaccaatca gttcgcttct cgcttctgtt cgcgcgcttc tgctccccga | 300 |
| gctcaataaa agagcccaca acccctcact cggggcgcca gtcctccgat tgactgagtc | 360 |
| gcccgggtac ccgtgtatcc aataaaccct cttgcagttg catccgactt gtggtctcgc | 420 |
| tgttccttgg gagggtctcc tctgagtgat tgactacccg tcagcggggg tctttcattt | 480 |
| gggggctcgt ccgggatcgg gagacccctg cccaggacc accgacccac caccgggagg | 540 |
| caagctggcc agcaacttat ctgtgtctgt ccgattgtct agtgtctatg actgatttta | 600 |
| tgcgcctgcg tcggtactag ttagctaact agctctgtat ctggcggacc cgtggtggaa | 660 |
| ctgacgagtt cggaacaccc ggccgcaacc ctgggagacg tcccagggac ttcggggggcc | 720 |
| gttttttgtgg cccgacctga gtccaaaaat cccgatcgtt ttggactctt tggtgcaccc | 780 |
| cccttagagg agggatatgt ggttctggta ggagacgaga acctaaaaca gttcccgcct | 840 |
| ccgtctgaat ttttgctttc ggtttgggac cgaagccgcg ccgcgcgtct tgtctgctgc | 900 |
| agcatcgttc tgtgttgtct ctgtctgact gtgtttctgt atttgtctga gaattagggc | 960 |
| cagactgtta ccactcccct aagtttgacc ttaggtcact ggaaagatgt cgagcggatc | 1020 |
| gctcacaacc agtcggtaga tgtcaagaag agacgttggg ttaccttctg ctctgcagaa | 1080 |
| tggccaacct ttaacgtcgg atggccgcga cacggcacct ttaaccgaga cctcatcacc | 1140 |
| caggttaaga tcaaggtctt ttcacctggc ccgcatggac acccagacca ggtcccctac | 1200 |
| atcgtgacct gggaagcctt ggcttttgac ccccctccct gggtcaagcc ctttgtacac | 1260 |
| cctaagcctc cgcctcctct tcctccatcc gccccgtctc tcccccttga acctcctcgt | 1320 |
| tcgaccccgc ctcgatcctc cctttatcca gccctcactc cttctctagg cgccggccgg | 1380 |
| atccgttgct gaagttccta ttccgaagtt cctattcttc aaatagtata ggaacttcgt | 1440 |
| taacgaagtt cctattccga agttcctatt ctctagaaag tataggaact tctcgtgacg | 1500 |
| gtctcgaagc cgcggtggag cgaggaagcg gaagagtcta gaataacttc gtatagtata | 1560 |
| cattatacga agttatgggt cgatggtgag atctggacta gagggtcgat ggtgatgctt | 1620 |
| ggataacttc gtatagcata cattatacga agttatcgga tcccagtgtg gtggtactcg | 1680 |
| aggtcgactc tagaggatcg agccccagct ggttctttcc gtctcagaag ccatagagcc | 1740 |
| caccgcatcc ccagcatgcc tgctattgtc ttcccaatcc tccccttgc tgtcctgccc | 1800 |
| cacccccaccc cccagaatag aatgacacct actcagacaa tgcgatgcaa tttcctcatt | 1860 |
| ttattaggaa aggacagtgg gagtggcacc ttccagggtc aaggaaggca cggggggaggg | 1920 |
| gcaaacaaca gatggctggc aactagaagg cacagtcgag gctgatcagc gagctctaga | 1980 |
| gaattgatcc cctcagaaga actcgtcaag aaggcgatag aaggcgatgc gctgcgaatc | 2040 |

-continued

```
gggagcggcg ataccgtaaa gcacgaggaa gcggtcagcc cattcgccgc caagctcttc    2100
agcaatatca cgggtagcca acgctatgtc ctgatagcgg tccgccacac ccagccggcc    2160
acagtcgatg aatccagaaa agcggccatt ttccaccatg atattcggca agcaggcatc    2220
gccatgggtc acgacgagat cctcgccgtc gggcatgcgc gccttgagcc tggcgaacag    2280
ttcggctggc gcgagcccct gatgctcttc gtccagatca tcctgatcga caagaccggc    2340
ttccatccga gtacgtgctc gctcgatgcg atgtttcgct tggtggtcga atgggcaggt    2400
agccggatca agcgtatgca gccgccgcat tgcatcagcc atgatggata ctttctcggc    2460
aggagcaagg tgagatgaca ggagatcctg ccccggcact tcgcccaata gcagccagtc    2520
ccttcccgct tcagtgacaa cgtcgagcac agctgcgcaa ggaacgcccg tcgtggccag    2580
ccacgatagc cgcgctgcct cgtcctgcag ttcattcagg gcaccggaca ggtcggtctt    2640
gacaaaaaga accgggcgcc cctgcgctga cagccggaac acggcggcat cagagcagcc    2700
gattgtctgt tgtgcccagt catagccgaa tagcctctcc acccaagcgg ccggagaacc    2760 tgccgtgcaat ccatcttgtt caatggccga tcccatattg gctgcagccc ggggggatccc   2820 ctgacaccag accaactggt aatggtagcg accggcgctc agctggaatt ccgccgatac    2880
tgacgggctc caggagtcgt cgccaccaat ccccatatgg aaaccgtcga tattcagcca    2940
tgtgccttct tccgcgtgca gcagatgcgc atggctggtt ccatcagtt gctgttgact     3000 gtagcggctg atgttgaact ggaagtcgcc gcgccactgg tgtgggccat aattcaattc    3060
gcgcgtcccg cagcgcagac cgttttcgct cgggaagacg tacggggtat acatgtctga    3120
caatggcaga tcccagcggt caaaacaggc ggcagtaagg cggtcgggat agttttcttg    3180
cggccctaat ccgagccagt ttacccgctc tgctacctgc gccagctggc agttcaggcc    3240
aatccgcgcc ggatgcggtg tatcgctcgc cacttcaaca tcaacggtaa tcgccatttg    3300
accactacca tcaatccggt aggttttccg gctgataaat aaggttttcc cctgatgctg    3360
ccacgcgtga gcggtcgtaa tcagcaccgc atcagcaagt gtatctgccg tgcactgcaa    3420
caacgctgct tcggcctggt aatgccccgc cgccttccag cgttcgaccc aggcgttagg    3480
gtcaatgcgg gtcgcttcac ttacgccaat gtcgttatcc agcggtgcac gggtgaactg    3540
atcgcgcagc ggcgtcagca gttgtttttt atcgccaatc cacatctgtg aaagaaagcc    3600
tgactggcgg ttaaattgcc aacgcttatt acccagctcg atgcaaaaat ccatttcgct    3660
ggtggtcaga tgcgggatgg cgtgggacgc ggcggggagc gtcacactga ggttttccgc    3720
cagacgccac tgctgccagg cgctgatgtg cccggcttct gaccatgcgg tcgcgttcgg    3780
ttgcactacg cgtactgtga gccagagttg cccggcgctc tccggctgcg gtagttcagg    3840
cagttcaatc aactgtttac cttgtggagc gacatccaga ggcacttcac cgcttgccag    3900
cggcttacca tccagcgcca ccatccagtg caggagctcg ttatcgctat gacggaacag    3960
gtattcgctg gtcacttcga tggtttgccc ggataaacgg aactggaaaa actgctgctg    4020
gtgttttgct tccgtcagcg ctggatgcgg cgtgcggtcg gcaaagacca gaccgttcat    4080
acagaactgg cgatcgttcg gcgtatcgcc aaaatcaccg ccgtaagccg accacgggtt    4140
gccgttttca tcatatttaa tcagcgactg atccacccag tcccagacga agccgccctg    4200
taaacgggga tactgacgaa acgcctgcca gtatttagcg aaaccgccaa gactgttacc    4260
catcgcgtgg gcgtattcgc aaaggatcag cgggcgcgtc tctccaggta gcgaaagcca    4320
ttttttgatg gaccatttcg gcacagccgg gaagggctgg tcttcatcca cgcgcgcgta    4380
```

```
catcgggcaa ataatatcgg tggccgtggt gtcggctccg ccgccttcat actgcaccgg    4440
gcgggaagga tcgacagatt tgatccagcg atacagcgcg tcgtgattag cgccgtggcc    4500
tgattcattc cccagcgacc agatgatcac actcgggtga ttacgatcgc gctgcaccat    4560
tcgcgttacg cgttcgctca tcgccggtag ccagcgcgga tcatcggtca gacgattcat    4620
tggcaccatg ccgtgggttt caatattggc ttcatccacc acatacaggc cgtagcggtc    4680
gcacagcgtg taccacagcg gatggttcgg ataatgcgaa cagcgcacgg cgttaaagtt    4740
gttctgcttc atcagcagga tatcctgcac catcgtctgc tcatccatga cctgaccatg    4800
cagaggatga tgctcgtgac ggttaacgcc tcgaatcagc aacggcttgc cgttcagcag    4860
cagcagacca ttttcaatcc gcacctcgcg gaaaccgaca tcgcaggctt ctgcttcaat    4920
cagcgtgccg tcggcggtgt gcagttcaac caccgcacga tagagattcg ggatttcggc    4980
gctccacagt ttcgggtttt cgacgttcag acgtagtgtg acgcgatcgg cataaccacc    5040
acgctcatcg ataatttcac cgccgaaagg cgcggtgccg ctggcgacct gcgtttcacc    5100
ctgccataaa gaaactgtta cccgtaggta gtcacgcaac tcgccgcaca tctgaacttc    5160
agcctccagt acagcgcggc tgaaatcatc attaaagcga gtggcaacat ggaaatcgct    5220
gatttgtgta gtcggtttat gcagcaacga gacgtcacgg aaaatgccgc tcatccgcca    5280
catatcctga tcttccagat aactgccgtc actccaacgc agcaccatca ccgcgaggcg    5340
gttttctccg cgcgtaaaa atgcgctcag gtcaaattca gacggcaaac gactgtcctg    5400
gccgtaaccg acccagcgcc cgttgcacca cagatgaaac gccgagttaa cgccatcaaa    5460
aataattcgc gtctggcctt cctgtagcca gctttcatca acattaaatg tgagcgagta    5520
acaacccgtc ggattctccg tgggaacaaa cggcggattg accgtaatgg dataggttac    5580
gttggtgtag atgggcgcat cgtaaccgtg catctgccag tttgagggga cgacgacagt    5640
atcggcctca ggaagatcgc actccagcca gctttccggc accgcttctg gtgccggaaa    5700
ccaggcaaag cgccattcgc cattcaggct gcgcaactgt tgggaagggc gatcggtgcg    5760
ggcctcttcg ctattacgcc agctggcgaa agggggatgt gctgcaaggc gattaagttg    5820
ggtaacgcca gggttttccc agtcacgacg ttgtaaaacg acgggatccg ccatgtcaca    5880
gatcatcaag cttatcgata ccgtcgatcc ccactggaaa gaccgcgaag agtttgtcct    5940
caaccgcgag ctgtggaaaa aaagggaca ggataagtat gacatcatca aggaaaccct    6000
ggactactgc gccctacaga tctgcagccc gggggatcca ctagttctag cctcgagtag    6060
gaattcgata acttcgtata atgtatacta tacgaagtta tgggtcgatg gtgatgcttg    6120
gcaattcggg tcgatggtga agcttggata acttcgtata atgtatgcta tacgaagtta    6180
tcaattcgcc ctatagtgag tcgtattctc ccgaaaaccg cttctagcaa cgaagttcct    6240
atactatttg aagaatagga acttcggaat aggaacttca gctctgtatc gtctatcgtt    6300
atgtctaatg gtatctgatg cagatcttct gtatcgtcta tcgttatgtc taatggtatc    6360
tgatgcagat ctgctgaagt tcctatactt tctagagaat aggaacttcg gaataggaac    6420
ttcgaattct cgagggcccg ggctcgacca gctgtgcgca tagtggcttg aatcgataaa    6480 ataaagatt ttatttagtc tccagaaaaa gggggaatg aaagacccca cctgtaggtt    6540
tggcaagcta gcacaacccc tcactcgggg cgccagtcct ccgattgact gagtcgcccg    6600
ggtacccgtg tatccaataa accctcttgc agttgcatcc gacttgtggt ctcgctgttc    6660
cttgggaggg tctcctctga gtgattgact acccgtcagc gggggtcttt cacatgcagc    6720
atgtatcaaa attaatttgg ttttttttct taagtatttta cattaaatgg ccatagttgc    6780
```

```
attaatgaat cggccaacgc gcggggagag gcggtttgcg tattgggcgc tcttccgctt    6840
cctcgctcac tgactcgctg cgctcggtcg ttcggctgcg gcgagcggta tcagctcact    6900
caaaggcggt aatacggtta tccacagaat caggggataa cgcaggaaag aacatgtgag    6960
caaaaggcca gcaaaggcca ggaaccgta aaaaggccgc gttgctggcg ttttttccata    7020 ggctccgccc ccctgacgag catcacaaaa atcgacgctc aagtcagagg tggcgaaacc    7080
cgacaggact ataaagatac caggcgtttc ccctggaag ctcccgtgt cgctctcctg    7140 ttccgaccct gccgcttacc ggatacctgt ccgcctttct cccttcggga agcgtggcgc    7200
tttctcatag ctcacgctgt aggtatctca gttcggtgta ggtcgttcgc tccaagctgg    7260
gctgtgtgca cgaaccccc gttcagcccg accgctgcgc cttatccggt aactatcgtc    7320
ttgagtccaa cccggtaaga cacgacttat cgccactggc agcagccact ggtaacagga    7380
ttagcagagc gaggtatgta ggcggtgcta cagagttctt gaagtggtgg cctaactacg    7440
gctacactag aaggacagta tttggtatct gcgctctgct gaagccagtt accttcggaa    7500
aaagagttgg tagctcttga tccggcaaac aaaccaccgc tggtagcggt ggtttttttg    7560
tttgcaagca gcagattacg cgcagaaaaa aaggatctca agaagatcct ttgatctttt    7620
ctacggggtc tgacgctcag tggaacgaaa actcacgtta agggattttg gtcatgagat    7680
tatcaaaaag gatcttcacc tagatccttt tgcggccgca aatcaatcta agtatatat    7740 gagtaaactt ggtctgacag ttaccaatgc ttaatcagtg aggcacctat ctcagcgatc    7800
tgtctatttc gttcatccat agttgcctga ctccccgtcg tgtagataac tacgatacgg    7860
gagggcttac catctggccc cagtgctgca atgataccgc gagacccacg ctcaccggct    7920
ccagatttat cagcaataaa ccagccagcc ggaagggccg agcgcagaag tggtcctgca    7980
actttatccg cctccatcca gtctattaat tgttgccggg aagctagagt aagtagttcg    8040
ccagttaata gtttgcgcaa cgttgttgcc attgctgcag gcatcgtggt gtcacgctcg    8100
tcgtttggta tggcttcatt cagctccggt tcccaacgat caaggcgagt tacatgatcc    8160
cccatgttgt gcaaaaaagc ggttagctcc ttcggtcctc cgatcgttgt cagaagtaag    8220
ttggccgcag tgttatcact catggttatg gcagcactgc ataattctct tactgtcatg    8280
ccatccgtaa gatgctttc tgtgactggt gagtactcaa ccaagtcatt ctgagaatag    8340
tgtatgcggc gaccgagttg ctcttgcccg gcgtcaatac gggataatac cgcgccacat    8400
agcagaactt taaaagtgct catcattgga aaacgttctt cggggcgaaa actctcaagg    8460
atcttaccgc tgttgagatc cagttcgatg taacccactc gtgcacccaa ctgatcttca    8520
gcatctttta ctttcaccag cgtttctggg tgagcaaaaa caggaaggca aaatgccgca    8580
aaaaagggaa taagggcgac acggaaatgt tgaatactca tactcttcct ttttcaatat    8640
tattgaagca tttatcaggg ttattgtctc atgagcggat acatatttga atgtatttag    8700
aaaaataaac aaataggggt tccgcgcaca tttccccgaa                           8740
```

<210> SEQ ID NO 4
<211> LENGTH: 8878
<212> TYPE: DNA
<213> ORGANISM: Artificial
<220> FEATURE:
<223> OTHER INFORMATION: Retroviral gene trap vector eFlip3ROSAbetaGeo

<400> SEQUENCE: 4

```
ctgcagcctg aatatgggcc aaacaggata tctgtggtaa gcagttcctg ccccggctca      60
```

```
gggccaagaa cagatggaac agctgaatat gggccaaaca ggatatctgt ggtaagcagt      120
tcctgccccg gctcagggcc aagaacagat ggtccccaga tgcggtccag ccctcagcag      180
tttctagaga accatcagat gtttccaggg tgccccaagg acctgaaatg accctgtgcc      240
ttatttgaac taaccaatca gttcgcttct cgcttctgtt cgcgcgcttc tgctccccga      300
gctcaataaa agagcccaca acccctcact cggggcgcca gtcctccgat tgactgagtc      360
gcccgggtac ccgtgtatcc aataaaccct cttgcagttg catccgactt gtggtctcgc      420
tgttccttgg gagggtctcc tctgagtgat tgactacccg tcagcggggg tctttcattt      480
gggggctcgt ccgggatcgg agacccctg cccagggacc accgacccac caccgggagg      540
caagctggcc agcaacttat ctgtgtctgt ccgattgtct agtgtctatg actgatttta      600
tgcgcctgcg tcgtactag ttagctaact agctctgtat ctggcggacc cgtggtggaa      660
ctgacgagtt cggaacaccc ggccgcaacc ctggagacg tcccagggac ttcggggcc      720 gttttttgtgg cccgacctga gtccaaaaat cccgatcgtt ttggactctt tggtgcaccc      780
cccttagagg agggatatgt ggttctggta ggagacgaga acctaaaaca gttcccgcct      840
ccgtctgaat ttttgctttc ggtttgggac cgaagccgcg ccgcgcgtct tgtctgctgc      900
agcatcgttc tgtgttgtct ctgtctgact gtgtttctgt atttgtctga gaattagggc      960
cagactgtta ccactccctt aagtttgacc ttaggtcact ggaaagatgt cgagcggatc     1020
gctcacaacc agtcggtaga tgtcaagaag agacgttggg ttaccttctg ctctgcagaa     1080
tggccaacct ttaacgtcgg atggccgcga gacggcacct ttaaccgaga cctcatcacc     1140
caggttaaga tcaaggtctt ttcacctggc ccgcatggac acccagacca ggtccctac     1200 atcgtgacct gggaagcctt ggcttttgac ccccctccct gggtcaagcc cttttgtacac     1260 cctaagcctc cgcctcctct tcctccatcc gccccgtctc tccccttga acctcctcgt     1320 tcgaccccgc ctcgatcctc cctttatcca gccctcactc cttctctagg cgccggccgg     1380
atccgttgct gaagttccta ttccgaagtt cctattcttc aaatagtata ggaacttcgt     1440
taacgaagtt cctattccga agttcctatt ctctagaaag tataggaact tctcgtgacg     1500
gtctcgaagc cgcggtggag cgaggaagcg aagagtcta gaataacttc gtatagtata     1560
cattatacga agttatgggt cgatggtgag atctggacta gagggtcgat ggtgatgctt     1620
ggataacttc gtatagcata cattatacga agttatcgga tcccagtgtg gtggtactcg     1680
aggtcgactc tagaggatcg agcccagct ggttcttttcc gtctcagaag ccatagagcc     1740
caccgcatcc ccagcatgcc tgctattgtc ttcccaatcc tccccttgc tgtcctgccc     1800 cacccccaccc cccagaatag aatgacacct actcagacaa tgcgatgcaa tttcctcatt     1860
ttattaggaa aggacagtgg gagtggcacc ttccagggtc aaggaaggca cgggggaggg     1920
gcaaacaaca gatggctggc aactagaagg cacagtcgag gctgatcagc gagctctaga     1980
gaattgatcc cctcagaaga actcgtcaag aaggcgatag aaggcgatgc gctgcgaatc     2040
gggagcggcg ataccgtaaa gcacgaggaa gcggtcagcc cattcgccgc caagctcttc     2100
agcaatatca cgggtagcca acgctatgtc ctgatagcgg tccgccacac ccagccggcc     2160
acagtcgatg aatccagaaa agcggccatt ttccaccatg atattcggca agcaggcatc     2220
gccatgggtc acgacgagat cctcgccgtc gggcatgcgc gccttgagcc tggcgaacag     2280
ttcggctggc gcgagcccct gatgctcttc gtccagatca tcctgatcga caagaccggc     2340
ttccatccga gtacgtgctc gctcgatgcg atgtttcgct tggtggtcga atgggcaggt     2400
agccggatca agcgtatgca gccgccgcat tgcatcagcc atgatggata ctttctcggc     2460
```

```
aggagcaagg tgagatgaca ggagatcctg ccccggcact tcgcccaata gcagccagtc    2520
ccttcccgct tcagtgacaa cgtcgagcac agctgcgcaa ggaacgcccg tcgtggccag    2580
ccacgatagc cgcgctgcct cgtcctgcag ttcattcagg gcaccggaca ggtcggtctt    2640
gacaaaaaga accgggcgcc cctgcgctga cagccggaac acggcggcat cagagcagcc    2700
gattgtctgt tgtgcccagt catagccgaa tagcctctcc acccaagcgg ccggagaacc    2760
tgcgtgcaat ccatcttgtt caatggccga tcccatattg gctgcagccc ggggatccc    2820 ctgacaccag accaactggt aatggtagcg accggcgctc agctggaatt ccgccgatac    2880
tgacgggctc caggagtcgt cgccaccaat ccccatatgg aaaccgtcga tattcagcca    2940
tgtgccttct tccgcgtgca gcagatggcg atggctggtt ccatcagtt gctgttgact     3000 gtagcggctg atgttgaact ggaagtcgcc gcgccactgg tgtgggccat aattcaattc    3060
gcgcgtcccg cagcgcagac cgttttcgct cgggaagacg tacggggtat acatgtctga    3120
caatggcaga tcccagcggt caaaacaggc ggcagtaagg cggtcgggat agttttcttg    3180
cggccctaat ccgagccagt ttacccgctc tgctacctgc gccagctggc agttcaggcc    3240
aatccgcgcc ggatgcggtg tatcgctcgc cacttcaaca tcaacggtaa tcgccatttg    3300
accactacca tcaatccggt aggttttccg gctgataaat aaggttttcc cctgatgctg    3360
ccacgcgtga gcggtcgtaa tcagcaccgc atcagcaagt gtatctgccg tgcactgcaa    3420
caacgctgct tcggcctggt aatggcccgc cgccttccag cgttcgaccc aggcgttagg    3480
gtcaatgcgg gtcgcttcac ttacgccaat gtcgttatcc agcggtgcac gggtgaactg    3540
atcgcgcagc ggcgtcagca gttgtttttt atcgccaatc cacatctgtg aaagaaagcc    3600 tgactgcgg ttaaattgcc aacgcttatt acccagctcg atgcaaaaat ccatttcgct     3660
ggtggtcaga tgcgggatgg cgtgggacgc ggcggggagc gtcacactga ggttttccgc    3720
cagacgccac tgctgccagg cgctgatgtg cccggcttct gaccatgcgg tcgcgttcgg    3780
ttgcactacg cgtactgtga gccagagttg cccggcgctc tccggctgcg gtagttcagg    3840
cagttcaatc aactgtttac cttgtgggagc gacatccaga ggcacttcac cgcttgccag    3900
cggcttacca tccagcgcca ccatccagtg caggagctct ttatcgctat gacggaacag    3960
gtattcgctg gtcacttcga tggttttgccc ggataaacgg aactggaaaa actgctgctg    4020
gtgttttgct tccgtcagcg ctggatgcgg cgtgcggtcg gcaaagacca gaccgttcat    4080
acagaactgg cgatcgttcg gcgtatcgcc aaaatcaccg ccgtaagccg accacgggtt    4140
gccgttttca tcatatttaa tcagcgactg atccacccag tcccagacga agccgccctg    4200
taaacgggga tactgacgaa acgcctgcca gtatttagcg aaaccgccaa gactgttacc    4260
catcgcgtgg gcgtattcgc aaaggatcag cgggcgcgtc tctccaggta gcgaaagcca    4320
ttttttgatg gaccatttcg gcacagccgg aagggctgg tcttcatcca cgcgcgcgta     4380
catcgggcaa ataatatcgg tggccgtggt gtcggctccg ccgccttcat actgcaccgg    4440
gcgggaagga tcgacagatt tgatccagcg atacagcgcg tcgtgattag cgccgtggcc    4500
tgattcattc cccagcgacc agatgatcac actcgggtga ttacgatcgc gctgcaccat    4560
tcgcgttacg cgttcgctca tcgccggtag ccagcgcgga tcatcggtca gacgattcat    4620
tggcaccatg ccgtgggttt caatattggc ttcatccacc acatacaggc cgtagcggtc    4680
gcacagcgtg taccacagcg gatggttcgg ataatgcgaa cagcgcacgg cgttaaagtt    4740
gttctgcttc atcagcagga tatcctgcac catcgtctgc tcatccatga cctgaccatg    4800
```

```
cagaggatga tgctcgtgac ggttaacgcc tcgaatcagc aacggcttgc cgttcagcag    4860
cagcagacca ttttcaatcc gcacctcgcg gaaaccgaca tcgcaggctt ctgcttcaat    4920
cagcgtgccg tcggcggtgt gcagttcaac caccgcacga tagagattcg ggatttcggc    4980
gctccacagt ttcgggtttt cgacgttcag acgtagtgtg acgcgatcgg cataaccacc    5040
acgctcatcg ataatttcac cgccgaaagg cgcggtgccg ctggcgacct gcgtttcacc    5100
ctgccataaa gaaactgtta cccgtaggta gtcacgcaac tcgccgcaca tctgaacttc    5160
agcctccagt acagcgcggc tgaaatcatc attaaagcga gtggcaacat ggaaatcgct    5220
gatttgtgta gtcggtttat gcagcaacga gacgtcacgg aaaatgccgc tcatccgcca    5280
catatcctga tcttccagat aactgccgtc actccaacgc agcaccatca ccgcgaggcg    5340
gttttctccg gcgcgtaaaa atgcgctcag gtcaaattca gacggcaaac gactgtcctg    5400
gccgtaaccg acccagcgcc cgttgcacca cagatgaaac gccgagttaa cgccatcaaa    5460
aataattcgc gtctggcctt cctgtagcca gctttcatca acattaaatg tgagcgagta    5520
acaacccgtc ggattctccg tgggaacaaa cggcggattg accgtaatgg dataggttac    5580
gttggtgtag atgggcgcat cgtaaccgtg catctgccag tttgagggga cgacgacagt    5640
atcggcctca ggaagatcgc actccagcca gcttccggc accgcttctg gtgccggaaa    5700
ccaggcaaag cgccattcgc cattcaggct gcgcaactgt tgggaagggc gatcggtgcg    5760
ggcctcttcg ctattacgcc agctggcgaa aggggggatgt gctgcaaggc gattaagttg    5820
ggtaacgcca gggttttccc agtcacgacg ttgtaaaacg acgggatccg ccatgtcaca    5880
gatcatcaag cttatcgata ccgtcgatcc ccactggaaa gaccgcgaag agtttgtcct    5940
caaccgcgag ctgtggaaaa aaagggaca ggataagtat gacatcatca aggaaaccct    6000
ggactactgc gccctacaga tctgcagccc ggggggatcca ctagttctag cctcgagtag    6060
gaattcgata acttcgtata atgtatacta tacgaagtta tgggtcgatg gtgatgcttg    6120
gcaattcggg tcgatggtga agcttggata acttcgtata atgtatgcta tacgaagtta    6180
tcaattcgcc ctatagtgag tcgtattctc ccgaaaaccg cttctagcaa cgaagttcct    6240
atactatttg aagaatagga acttcggaat aggaacttca gcagatctgc ttttccattt    6300
gcatttcaaa tgtgatttta acttacatta tacaaagctg aaaggtcagt gcaggatctg    6360
cttttccatt tgcatttcaa atgtgatttt aacttacatt atacaaagct gaaaggtcag    6420
tgcaggatct gcttttccat ttgcatttca aatgtgattt taacttacat tatacaaagc    6480
tgaaaggtca gtgcaggatc tgctgaagtt cctatacttt ctagagaata ggaacttcgg    6540
aataggaact tcgaattctc gagggcccgg gctcgaccag ctgtgcgcat agtggcttga    6600
atcgataaaa taaagatttt atttagtct ccagaaaaag gggggaatga agaccccac    6660 ctgtaggttt ggcaagctag cacaacccct cactcggggc gccagtcctc cgattgactg    6720
agtcgcccgg gtaccgtgt atccaataaa ccctcttgca gttgcatccg acttgtggtc    6780
tcgctgttcc ttgggagggt ctcctctgag tgattgacta cccgtcagcg ggggtctttc    6840
acatgcagca tgtatcaaaa ttaatttggt tttttttctt aagtatttac attaaatggc    6900
catagttgca ttaatgaatc ggccaacgcg cggggagagg cggtttgcgt attgggcgct    6960
cttccgcttc ctcgctcact gactcgctgc gctcggtcgt tcggctgcgg cgagcggtat    7020
cagctcactc aaaggcggta atacggttat ccacagaatc aggggataac gcaggaaaga    7080
acatgtgagc aaaaggccag caaaaggcca ggaaccgtaa aaaggccgcg ttgctggcgt    7140
ttttccatag gctccgcccc cctgacgagc atcacaaaaa tcgacgctca agtcagaggt    7200
```

```
ggcgaaaccc gacaggacta taaagatacc aggcgtttcc ccctggaagc tccctcgtgc    7260
gctctcctgt tccgaccctg ccgcttaccg gatacctgtc cgcctttctc ccttcgggaa    7320
gcgtggcgct ttctcatagc tcacgctgta ggtatctcag ttcggtgtag gtcgttcgct    7380
ccaagctggg ctgtgtgcac gaaccccccg ttcagcccga ccgctgcgcc ttatccggta    7440
actatcgtct tgagtccaac ccggtaagac acgacttatc gccactggca gcagccactg    7500
gtaacaggat tagcagagcg aggtatgtag gcggtgctac agagttcttg aagtggtggc    7560
ctaactacgg ctacactaga aggacagtat ttggtatctg cgctctgctg aagccagtta    7620
ccttcggaaa aagagttggt agctcttgat ccggcaaaca aaccaccgct ggtagcggtg    7680
gtttttttgt ttgcaagcag cagattacgc gcagaaaaaa aggatctcaa gaagatcctt    7740
tgatcttttc tacggggtct gacgctcagt ggaacgaaaa ctcacgttaa gggattttgg    7800
tcatgagatt atcaaaaagg atcttcacct agatcctttt gcggccgcaa atcaatctaa    7860
agtatatatg agtaaacttg gtctgacagt taccaatgct taatcagtga ggcacctatc    7920
tcagcgatct gtctatttcg ttcatccata gttgcctgac tccccgtcgt gtagataact    7980
acgatacggg agggcttacc atctggcccc agtgctgcaa tgataccgcg agacccacgc    8040
tcaccggctc cagatttatc agcaataaac cagccagccg aagggccga gcgcagaagt    8100 ggtcctgcaa ctttatccgc ctccatccag tctattaatt gttgccggga agctagagta    8160
agtagttcgc cagttaatag tttgcgcaac gttgttgcca ttgctgcagg catcgtggtg    8220
tcacgctcgt cgtttggtat ggcttcattc agctccggtt cccaacgatc aaggcgagtt    8280
acatgatccc ccatgttgtg caaaaaagcg gttagctcct tcggtcctcc gatcgttgtc    8340
agaagtaagt tggccgcagt gttatcactc atggttatgg cagcactgca taattctctt    8400
actgtcatgc catccgtaag atgcttttct gtgactggtg agtactcaac caagtcattc    8460
tgagaatagt gtatgcggcg accgagttgc tcttgcccgg cgtcaatacg ggataatacc    8520
gcgccacata gcagaacttt aaaagtgctc atcattggaa aacgttcttc ggggcgaaaa    8580
ctctcaagga tcttaccgct gttgagatcc agttcgatgt aacccactcg tgcacccaac    8640
tgatcttcag catcttttac tttcaccagc gtttctgggt gagcaaaaac aggaaggcaa    8700
aatgccgcaa aaaagggaat aagggcgaca cggaaatgtt gaatactcat actcttcctt    8760
tttcaatatt attgaagcat ttatcagggt tattgtctca tgagcggata catatttgaa    8820
tgtatttaga aaaataaaca ataggggttc cgcgcacat ttccccgaaa agtgccac     8878
```

<210> SEQ ID NO 5
<211> LENGTH: 9091
<212> TYPE: DNA
<213> ORGANISM: Artificial
<220> FEATURE:
<223> OTHER INFORMATION: Retroviral gene trap vector eFlip6ROSAbetaGeo

<400> SEQUENCE: 5

```
ctgcagcctg aatatgggcc aaacaggata tctgtggtaa gcagttcctg ccccggctca      60
gggccaagaa cagatggaac agctgaatat gggccaaaca ggatatctgt ggtaagcagt     120
tcctgccccg gctcagggcc aagaacagat ggtcccaga tgcggtccag ccctcagcag     180
tttctagaga accatcagat gtttccaggg tgccccaagg acctgaaatg accctgtgcc     240
ttatttgaac taaccaatca gttcgcttct cgcttctgtt cgcgcgcttc tgctccccga     300
gctcaataaa agagcccaca cccctcact cggggcgcca gtcctccgat tgactgagtc     360
```

```
gcccgggtac ccgtgtatcc aataaaccct cttgcagttg catccgactt gtggtctcgc    420
tgttccttgg gagggtctcc tctgagtgat tgactacccg tcagcggggg tctttcattt    480
gggggctcgt ccgggatcgg gagacccctg cccagggacc accgacccac caccgggagg    540
caagctggcc agcaacttat ctgtgtctgt ccgattgtct agtgtctatg actgatttta    600
tgcgcctgcg tcggtactag ttagctaact agctctgtat ctggcggacc cgtggtggaa    660
ctgacgagtt cggaacaccc ggccgcaacc ctgggagacg tcccagggac ttcggggcc     720 gttttttgtgg cccgacctga gtccaaaaat cccgatcgtt ttggactctt tggtgcaccc   780
cccttagagg agggatatgt ggttctggta ggagacgaga acctaaaaca gttcccgcct    840
ccgtctgaat ttttgctttc ggtttgggac cgaagccgcg ccgcgcgtct tgtctgctgc    900
agcatcgttc tgtgttgtct ctgtctgact gtgtttctgt atttgtctga gaattagggc    960
cagactgtta ccactccctt aagtttgacc ttaggtcact ggaaagatgt cgagcggatc   1020
gctcacaacc agtcggtaga tgtcaagaag agacgttggg ttaccttctg ctctgcagaa   1080
tggccaacct ttaacgtcgg atggccgcga gacggcacct ttaaccgaga cctcatcacc   1140
caggttaaga tcaaggtctt ttcacctggc ccgcatggac acccagacca ggtcccctac   1200
atcgtgacct gggaagcctt ggcttttgac cccctccct gggtcaagcc ctttgtacac    1260
cctaagcctc cgcctcctct tcctccatcc gccccgtctc tcccccttga acctcctcgt   1320
tcgaccccgc ctcgatcctc cctttatcca gccctcactc cttctctagg cgccggccgg   1380
atccgttgct gaagttccta ttccgaagtt cctattcttc aaatagtata ggaacttcgt   1440
taacgaagtt cctattccga agttcctatt ctctagaaag tataggaact tctcgtgacg   1500
gtctcgaagc cgcggtggag cgaggaagcg gaagagtcta gaataacttc gtatagtata   1560
cattatacga agttatgggt cgatggtgag atctggacta gagggtcgat ggtgatgctt   1620
ggataacttc gtatagcata cattatacga agttatcgga tcccagtgtg gtggtactcg   1680
aggtcgactc tagaggatcg agccccagct ggttctttcc gtctcagaag ccatagagcc   1740
caccgcatcc ccagcatgcc tgctattgtc ttcccaatcc tcccccttgc tgtcctgccc   1800
caccccaccc cccagaatag aatgacacct actcagacaa tgcgatgcaa tttcctcatt   1860
ttattaggaa aggacagtgg gagtggcacc ttccagggtc aaggaaggca cggggagggg   1920
gcaaacaaca gatggctggc aactagaagg cacagtcgag gctgatcagc gagctctaga   1980
gaattgatcc cctcagaaga actcgtcaag aaggcgatag aaggcgatgc gctgcgaatc   2040
gggagcggcg ataccgtaaa gcacgaggaa gcggtcagcc cattcgccgc caagctcttc   2100
agcaatatca cgggtagcca cgctatgtc ctgatagcgg tccgccacac ccagccggcc    2160
acagtcgatg aatccagaaa agcggccatt ttccaccatg atattcggca agcaggcatc   2220
gccatgggtc acgacgagat cctcgccgtc gggcatgcgc gccttgagcc tggcgaacag   2280
ttcggctggc gcgagcccct gatgctcttc gtccagatca tcctgatcga caagaccggc   2340
ttccatccga gtacgtgctc gctcgatgcg atgtttcgct tggtggtcga atgggcaggt   2400
agccggatca agcgtatgca gccgccgcat tgcatcagcc atgatggata ctttctcggc   2460
aggagcaagg tgagatgaca ggagatcctg ccccggcact cgcccaata gcagccagtc   2520 ccttcccgct tcagtgacaa cgtcgagcac agctgcgcaa ggaacgcccg tcgtggccag   2580
ccacgatagc cgcgctgcct cgtcctgcag ttcattcagg gcaccggaca ggtcggtctt   2640
gacaaaaaga accgggcgcc cctgcgctga cagccggaac acggcggcat cagagcagcc   2700
gattgtctgt tgtgcccagt catagccgaa tagcctctcc acccaagcgg ccggagaacc   2760
```

-continued

```
tgcgtgcaat ccatcttgtt caatggccga tcccatattg gctgcagccc gggggatccc   2820
ctgacaccag accaactggt aatggtagcg accggcgctc agctggaatt ccgccgatac   2880
tgacgggctc caggagtcgt cgccaccaat ccccatatgg aaaccgtcga tattcagcca   2940
tgtgccttct tccgcgtgca gcagatggcg atggctggtt tccatcagtt gctgttgact   3000
gtagcggctg atgttgaact ggaagtcgcc gcgccactgg tgtgggccat aattcaattc   3060
gcgcgtcccg cagcgcagac cgttttcgct cgggaagacg tacggggtat acatgtctga   3120
caatggcaga tcccagcggt caaaacaggc ggcagtaagg cggtcgggat agttttcttg   3180
cggccctaat ccgagccagt ttacccgctc tgctacctgc gccagctggc agttcaggcc   3240
aatccgcgcc ggatgcggtg tatcgctcgc cacttcaaca tcaacggtaa tcgccatttg   3300
accactacca tcaatccggt aggttttccg gctgataaat aaggttttcc cctgatgctg   3360
ccacgcgtga gcggtcgtaa tcagcaccgc atcagcaagt gtatctgccg tgcactgcaa   3420
caacgctgct tcggcctggt aatggcccgc cgccttccag cgttcgaccc aggcgttagg   3480
gtcaatgcgg gtcgcttcac ttacgccaat gtcgttatcc agcggtgcac gggtgaactg   3540
atcgcgcagc ggcgtcagca gttgtttttt atcgccaatc cacatctgtg aaagaaagcc   3600
tgactggcgg ttaaattgcc aacgcttatt acccagctcg atgcaaaaat ccatttcgct   3660
ggtggtcaga tgcgggatgg cgtgggacgc ggcggggagc gtcacactga ggttttccgc   3720
cagacgccac tgctgccagg cgctgatgtg cccggcttct gaccatgcgg tcgcgttcgg   3780
ttgcactacg cgtactgtga gccagagttg cccggcgctc tccggctgcg gtagttcagg   3840
cagttcaatc aactgtttac cttgtggagc gacatccaga ggcacttcac cgcttgccag   3900
cggcttacca tccagcgcca ccatccagtg caggagctcg ttatcgctat gacggaacag   3960
gtattcgctg gtcacttcga tggtttgccc ggataaacgg aactggaaaa actgctgctg   4020
gtgttttgct tccgtcagcg ctggatgcgg cgtgcggtcg gcaaagacca gaccgttcat   4080
acagaactgg cgatcgttcg gcgtatcgcc aaaatcaccg ccgtaagccg accacgggtt   4140
gccgttttca tcatatttaa tcagcgactg atccacccag tcccagacga agccgccctg   4200
taaacgggga tactgacgaa acgcctgcca gtatttagcg aaaccgccaa gactgttacc   4260
catcgcgtgg gcgtattcgc aaaggatcag cgggcgcgtc tctccaggta gcgaaagcca   4320
tttttttgatg gaccatttcg gcacagccgg gaagggctgg tcttcatcca cgcgcgcgta   4380
catcgggcaa ataatatcgg tggccgtggt gtcggctccg ccgccttcat actgcaccgg   4440
gcgggaagga tcgacagatt tgatccagcg atacagcgcg tcgtgattag cgccgtggcc   4500
tgattcattc cccagcgacc agatgatcac actcgggtga ttacgatcgc gctgcaccat   4560
tcgcgttacg cgttcgctca tcgccggtag ccagcgcgga tcatcggtca gacgattcat   4620
tggcaccatg ccgtgggttt caatattggc ttcatccacc acatacaggc cgtagcggtc   4680
gcacagcgtg taccacagcg gatggttcgg ataatgcgaa cagcgcacgg cgttaaagtt   4740
gttctgcttc atcagcagga tatcctgcac catcgtctgc tcatccatga cctgaccatg   4800
cagaggatga tgctcgtgac ggttaacgcc tcgaatcagc aacggcttgc cgttcagcag   4860
cagcagacca ttttcaatcc gcacctcgcg gaaaccgaca tcgcaggctt ctgcttcaat   4920
cagcgtgccg tcggcggtgt gcagttcaac caccgcacga tagagattcg ggatttcggc   4980
gctccacagt ttcgggtttt cgacgttcag acgtagtgtg acgcgatcgg cataaccacc   5040
acgctcatcg ataatttcac cgccgaaagg cgcggtgccg ctggcgacct gcgtttcacc   5100
```

```
ctgccataaa gaaactgtta cccgtaggta gtcacgcaac tcgccgcaca tctgaacttc    5160
agcctccagt acagcgcggc tgaaatcatc attaaagcga gtggcaacat ggaaatcgct    5220
gatttgtgta gtcggtttat gcagcaacga gacgtcacgg aaaatgccgc tcatccgcca    5280
catatcctga tcttccagat aactgccgtc actccaacgc agcaccatca ccgcgaggcg    5340
gttttctccg gcgcgtaaaa atgcgctcag gtcaaattca gacggcaaac gactgtcctg    5400
gccgtaaccg acccagcgcc cgttgcacca cagatgaaac gccgagttaa cgccatcaaa    5460
aataattcgc gtctggcctt cctgtagcca gctttcatca acattaaatg tgagcgagta    5520
acaacccgtc ggattctccg tgggaacaaa cggcggattg accgtaatgg gataggttac    5580
gttggtgtag atgggcgcat cgtaaccgtg catctgccag tttgagggga cgacgacagt    5640
atcggcctca ggaagatcgc actccagcca gctttccggc accgcttctg gtgccggaaa    5700
ccaggcaaag cgccattcgc cattcaggct gcgcaactgt tgggaagggc gatcggtgcg    5760
ggcctcttcg ctattacgcc agctggcgaa aggggatgt gctgcaaggc gattaagttg    5820
ggtaacgcca gggttttccc agtcacgacg ttgtaaaacg acgggatccg ccatgtcaca    5880
gatcatcaag cttatcgata ccgtcgatcc ccactggaaa gaccgcgaag agtttgtcct    5940
caaccgcgag ctgtggaaaa aaagggaca ggataagtat gacatcatca aggaaaccct    6000
ggactactgc gccctacaga tctgcagccc gggggatcca ctagttctag cctcgagtag    6060
gaattcgata acttcgtata atgtatacta tacgaagtta tgggtcgatg gtgatgcttg    6120
gcaattcggg tcgatggtga agcttggata acttcgtata atgtatgcta tacgaagtta    6180
tcaattcgcc ctatagtgag tcgtattctc ccgaaaaccg cttctagcaa cgaagttcct    6240
atactatttg aagaatagga acttcggaat aggaacttca gcagatctgc ttttccattt    6300
gcatttcaaa tgtgatttta acttacatta tacaaagctg aaaggtcagt gcaggatctg    6360
cttttccatt tgcatttcaa atgtgatttt aacttacatt atacaaagct gaaaggtcag    6420
tgcaggatct gcttttccat ttgcatttca atgtgatttt taacttacat tatacaaagc    6480
tgaaaggtca gtgcaggatc tgcttttcca tttgcatttc aaatgtgatt ttaacttaca    6540
ttatacaaag ctgaaaggtc agtgcaggat ctgcttttcc atttgcattt caaatgtgat    6600
tttaacttac attatacaaa gctgaaaggt cagtgcagga tctgcttttc catttgcatt    6660
tcaaatgtga ttttaactta cattatacaa agctgaaagg tcagtgcagg atctgctgaa    6720
gttcctatac tttctagaga ataggaactt cggaatagga acttcgaatt ctcgagggcc    6780
cgggctcgac cagctgtgcg catagtggct tgaatcgata aaataaaaga ttttatttag    6840
tctccagaaa aaggggggaa tgaaagaccc cacctgtagg tttggcaagc tagcacaacc    6900
cctcactcgg ggcgccagtc ctccgattga ctgagtcgcc cgggtacccg tgtatccaat    6960
aaaccctctt gcagttgcat ccgacttgtg gtctcgctgt tccttgggag gtctcctct    7020 gagtgattga ctacccgtca gcggggggtct ttcacatgca gcatgtatca aaattaatt    7080 ggttttttt cttaagtatt tacattaaat ggccatagtt gcattaatga atcggccaac    7140
gcgcggggag aggcggtttg cgtattgggc gctcttccgc ttcctcgctc actgactcgc    7200
tgcgctcggt cgttcggctg cggcgagcgg tatcagctca ctcaaaggcg gtaatacggt    7260
tatccacaga atcaggggat aacgcaggaa agaacatgtg agcaaaaggc cagcaaaagg    7320
ccaggaaccg taaaaaggcc gcgttgctgg cgttttttcca taggctccgc ccccctgacg    7380
agcatcacaa aaatcgacgc tcaagtcaga ggtggcgaaa cccgacagga ctataaagat    7440
accaggcgtt ccccctgga agctccctcg tgcgctctcc tgttccgacc ctgccgctta    7500
```

```
ccggatacct gtccgccttt ctcccttcgg gaagcgtggc gctttctcat agctcacgct    7560
gtaggtatct cagttcggtg taggtcgttc gctccaagct gggctgtgtg cacgaacccc    7620
ccgttcagcc cgaccgctgc gccttatccg gtaactatcg tcttgagtcc aacccggtaa    7680
gacacgactt atcgccactg gcagcagcca ctggtaacag gattagcaga gcgaggtatg    7740
taggcggtgc tacagagttc ttgaagtggt ggcctaacta cggctacact agaaggacag    7800
tatttggtat ctgcgctctg ctgaagccag ttaccttcgg aaaaagagtt ggtagctctt    7860
gatccggcaa acaaaccacc gctggtagcg gtggtttttt tgtttgcaag cagcagatta    7920
cgcgcagaaa aaaggatctc aagaagatcc tttgatcttt tctacggggt ctgacgctc     7980 agtggaacga aaactcacgt taagggattt tggtcatgag attatcaaaa aggatcttca    8040
cctagatcct tttgcggccg caaatcaatc taaagtatat atgagtaaac ttggtctgac    8100
agttaccaat gcttaatcag tgaggcacct atctcagcga tctgtctatt tcgttcatcc    8160
atagttgcct gactccccgt cgtgtagata actacgatac gggagggctt accatctggc    8220
cccagtgctg caatgatacc gcgagaccca cgctcaccgg ctccagattt atcagcaata    8280
aaccagccag ccggaagggc cgagcgcaga agtggtcctg caactttatc cgcctccatc    8340
cagtctatta attgttgccg ggaagctaga gtaagtagtt cgccagttaa tagtttgcgc    8400
aacgttgttg ccattgctgc aggcatcgtg gtgtcacgct cgtcgtttgg tatggcttca    8460
ttcagctccg gttcccaacg atcaaggcga gttacatgat cccccatgtt gtgcaaaaaa    8520
gcggttagct ccttcggtcc tccgatcgtt gtcagaagta agttggccgc agtgttatca    8580
ctcatggtta tggcagcact gcataattct cttactgtca tgccatccgt aagatgcttt    8640
tctgtgactg gtgagtactc aaccaagtca ttctgagaat agtgtatgcg gcgaccgagt    8700
tgctcttgcc cggcgtcaat acgggataat accgcgccac atagcagaac tttaaaagtg    8760
ctcatcattg gaaaacgttc ttcggggcga aaactctcaa ggatcttacc gctgttgaga    8820
tccagttcga tgtaacccac tcgtgcaccc aactgatctt cagcatcttt tactttcacc    8880
agcgtttctg ggtgagcaaa aacaggaagg caaaatgccg caaaaaaggg aataagggcg    8940
acacggaaat gttgaatact catactcttc ctttttcaat attattgaag catttatcag    9000
ggttattgtc tcatgagcgg atacatattt gaatgtattt agaaaaataa acaaataggg    9060
gttccgcgca catttccccg aaaagtgcca c                                   9091
```

<210> SEQ ID NO 6
<211> LENGTH: 10372
<212> TYPE: DNA
<213> ORGANISM: Artificial
<220> FEATURE:
<223> OTHER INFORMATION: Retroviral gene trap vector FlipROSAbetaGeoPuro

<400> SEQUENCE: 6

```
ctgcagcctg aatatgggcc aaacaggata tctgtggtaa gcagttcctg ccccggctca      60
gggccaagaa cagatggaac agctgaatat gggccaaaca ggatatctgt ggtaagcagt     120
tcctgccccg gctcagggcc aagaacagat ggtccccaga tgcggtccag ccctcagcag     180
tttctagaga accatcagat gtttccaggg tgccccaagg acctgaaatg accctgtgcc     240
ttatttgaac taaccaatca gttcgcttct cgcttctgtt cgcgcgcttc tgctccccga     300
gctcaataaa agagcccaca acccctcact cggggcgcca gtcctccgat tgactgagtc     360
gcccgggtac ccgtgtatcc aataaaccct cttgcagttg catccgactt gtggtctcgc     420
```

```
tgttccttgg gagggtctcc tctgagtgat tgactacccg tcagcggggg tctttcattt    480
gggggctcgt ccgggatcgg gagacccctg cccaggggacc accgaccccac caccgggagg  540
```
(correcting) 
```
tgttccttgg gagggtctcc tctgagtgat tgactacccg tcagcggggg tctttcattt    480
gggggctcgt ccgggatcgg gagacccctg cccaggggacc accgaccccac caccgggagg  540
caagctggcc agcaacttat ctgtgtctgt ccgattgtct agtgtctatg actgatttta    600
tgcgcctgcg tcggtactag ttagctaact agctctgtat ctggcggacc cgtggtggaa    660
ctgacgagtt cggaacaccc ggccgcaacc ctgggagacg tcccagggac ttcggggcc     720
gttttttgtgg cccgacctga gtccaaaaat cccgatcgtt ttggactctt tggtgcaccc   780
cccttagagg agggatatgt ggttctggta ggagacgaga acctaaaaca gttcccgcct    840
ccgtctgaat ttttgctttc ggtttgggac cgaagccgcg ccgcgcgtct tgtctgctgc    900
agcatcgttc tgtgttgtct ctgtctgact gtgtttctgt atttgtctga gaattagggc    960
cagactgtta ccactccctt aagtttgacc ttaggtcact ggaaagatgt cgagcggatc    1020
gctcacaacc agtcggtaga tgtcaagaag agacgttggg ttaccttctg ctctgcagaa    1080
tggccaacct ttaacgtcgg atggccgcga gacggcacct ttaaccgaga cctcatcacc    1140
caggttaaga tcaaggtctt ttcacctggc ccgcatggac acccagacca ggtcccctac    1200
atcgtgacct gggaagcctt ggcttttgac cccctccct gggtcaagcc ctttgtacac     1260
cctaagcctc cgcctcctct tcctccatcc gccccgtctc tcccccttga acctcctcgt    1320
tcgaccccgc ctcgatcctc cctttatcca gccctcactc cttctctagg cgccggccgg    1380
atccgttgct gaagttccta ttccgaagtt cctattcttc aaatagtata ggaacttcgt    1440
taacgaagtt cctattccga agttcctatt ctctagaaag tataggaact tctcgtgacg    1500
gtctcgaagc cgcgggagat ctaattctag atttaagctt ctgatggaat tagaacttgg    1560
caaaacaata ctgagaatga agtgtatgtg gaacagaggc tgctgatctc gttcttcagg    1620
ctatgaaact gacacatttg gaaaccacag tacttagaac cacaaagtgg gaatcaagag    1680
aaaaacaatg atcccacgag agatctatag atctatagat catgagtggg aggaatgagc    1740
tggcccttaa tttggtttag cttgtttaaa ttatgatatc caactatgaa acattatcat    1800
aaagcaatag taaagagcca cagtaaagag caggcattta tcttaatccc accccacccc    1860
cacccccgta gctccaatcc ttccattcaa aatgtaggta ctctgttctc acccttctta    1920
acaaagtatg acaggaaaaa cttccatttt agtggacatc tttattgttt aatagatcat    1980
caatttctgc agacttacag cggatcccct caggcaccgg gcttgcgggt catgcaccag    2040
gtcgcgcggt ccttcgggca ctcgacgtcg gcggtgacgg tgaagccgag ccgctcgtag    2100
aaggggaggt tgcggggcgc ggaggtctcc aggaaggcgg gcaccccggc gcgctcggcc    2160
gcctccactc cggggagcac gacggcgctg cccagaccct tgccctggtg gtcgggcgag    2220
acgccgacgg tggccaggaa ccacgcgggc tccttgggcc ggtgcggcgc caggaggcct    2280
tccatctgtt gctgcgcggc cagccgggaa ccgctcaact cggccatgcg cgggccgatc    2340
tcggcgaaca ccgcccccgc ttcgacgctc tccggcgtgg tccagaccgc caccgcggcg    2400
ccgtcgtccg cgacccacac cttgccgatg tcgagcccga cgcgcgtgag gaagagttct    2460
tgcagctcgg tgacccgctc gatgtggcgg tccggatcga cggtgtggcg cgtggcgggg    2520
tagtcggcga acgcggcggc gagggtgcgt acgccctggg gacgtcgtc gcgggtggcg     2580
aggcgcaccg tgggcttgta ctcggtcata ttggctgcag gtcgaaaggc ccggagatga    2640
ggaagaggag aacagcgcgg cagacgtgcg cttttgaagc gtgcagaatg ccgggctccg    2700
gaggaccttc gggcgcccgc cccgcccctg agcccgcccc tgagcccgcc cccggaccca    2760
cccccttccca gcctctgagc ccagaaagcg aaggagcaaa gctgctattg gccgctgccc    2820
```

```
caaaggccta cccgcttcca ttgctcagcg gtgctgtcca tctgcacgag actagtgaga    2880
cgtgctactt ccatttgtca cgtcctgcac gacgcgagct gcggggcggg gggaacttc    2940 ctgactaggg gaggagtaga aggtggcgcg aaggggccac caaagaacgg agccggttgg    3000
cgcctaccgg tggatgtgga atgtgtgcga ggccagaggc cacttgtgta gcgccaagtg    3060
cccagcgggg ctgctaaagc gcatgctcca gactgccttg gaaaagcgc ctcccctacc     3120 cggtagaatt ccccgcggtg gagcgaggaa gcggaagagt ctagaataac ttcgtatagt    3180
atacattata cgaagttatg ggtcgatggt gagatctgga ctagagggtc gatggtgatg    3240
cttggataac ttcgtatagc atacattata cgaagttatc ggatcccagt gtggtggtac    3300
tcgaggtcga ctctagagga tcgagcccca gctggttctt tccgtctcag aagccataga    3360
gcccaccgca tccccagcat gcctgctatt gtcttcccaa tcctcccct tgctgtcctg      3420 ccccaccca ccccccagaa tagaatgaca cctactcaga caatgcgatg caatttcctc     3480
attttattag gaaaggacag tgggagtggc accttccagg gtcaaggaag cacggggga    3540 ggggcaaaca acagatggct ggcaactaga aggcacagtc gaggctgatc agcgagctct    3600
agagaattga tcccctcaga agaactcgtc aagaaggcga tagaaggcga tgcgctgcga    3660
atcgggagcg gcgataccgt aaagcacgag gaagcggtca gcccattcgc cgccaagctc    3720
ttcagcaata tcacgggtag ccaacgctat gtcctgatag cggtccgcca cacccagccg    3780
gccacagtcg atgaatccag aaaagcggcc attttccacc atgatattcg gcaagcaggc    3840
atcgccatgg gtcacgacga atcctcgcc gtcgggcatg cgcgccttga gcctggcgaa     3900
cagttcggct ggcgcgagcc cctgatgctc ttcgtccaga tcatcctgat cgacaagacc    3960
ggcttccatc cgagtacgtg ctcgctcgat gcgatgtttc gcttggtggt cgaatgggca    4020
ggtagccgga tcaagcgtat gcagccgccg cattgcatca gccatgatgg atactttctc    4080
ggcaggagca aggtgagatg acaggagatc ctgccccggc acttcgccca atagcagcca    4140
gtcccttccc gcttcagtga caacgtcgag cacagctgcg caaggaacgc ccgtcgtggc    4200
cagccacgat agccgcgctg cctcgtcctg cagttcattc agggcaccgg acaggtcggt    4260
cttgacaaaa agaaccgggc gcccctgcgc tgacagccgg aacacggcgg catcagagca    4320
gccgattgtc tgttgtgccc agtcatagcc gaatagcctc tccacccaag cggccggaga    4380
acctgcgtgc aatccatctt gttcaatggc cgatcccata ttggctgcag ccggggggat    4440
cccctgacac cagaccaact ggtaatggta gcgaccggcg ctcagctgga attccgccga    4500
tactgacggg ctccaggagt cgtcgccacc aatccccata tggaaaccgt cgatattcag    4560
ccatgtgcct tcttccgcgt gcagcagatg gcgatggctg gtttccatca gttgctgttg    4620
actgtagcgc ctgatgttga actggaagtc gccgcgccac tggtgtgggc cataattcaa    4680
ttcgcgcgtc ccgcagcgca gaccgttttc gctcgggaag acgtacgggg tatacatgtc    4740
tgacaatggc agatcccagc ggtcaaaaca ggcggcagta aggcggtcgg atagttttc     4800 ttgcggccct aatccgagcc agtttacccg ctctgctacc tgcgccagct ggcagttcag    4860
gccaatccgc gccggatgcg gtgtatcgct cgccacttca acatcaacgg taatcgccat    4920
ttgaccacta ccatcaatcc ggtaggtttt ccggctgata aataaggttt tcccctgatg    4980
ctgccacgcg tgagcggtcg taatcagcac cgcatcagca agtgtatctg ccgtgcactg    5040
caacaacgct gcttcggcct ggtaatggcc gccgccttc cagcgttcga cccaggcgtt     5100
agggtcaatg cgggtcgctt cacttacgcc aatgtcgtta ccagcggtg cacgggtgaa     5160
```

```
ctgatcgcgc agcggcgtca gcagttgttt tttatcgcca atccacatct gtgaaagaaa    5220
gcctgactgg cggttaaatt gccaacgctt attacccagc tcgatgcaaa aatccatttc    5280
gctggtggtc agatgcggga tggcgtggga cgcggcgggg agcgtcacac tgaggttttc    5340
cgccagacgc cactgctgcc aggcgctgat gtgcccggct tctgaccatg cggtcgcgtt    5400
cggttgcact acgcgtactg tgagccagag ttgcccggcg ctctccggct gcggtagttc    5460
aggcagttca atcaactgtt taccttgtgg agcgacatcc agaggcactt caccgcttgc    5520
cagcggctta ccatccagcg ccaccatcca gtgcaggagc tcgttatcgc tatgacggaa    5580
caggtattcg ctggtcactt cgatggtttg cccggataaa cggaactgga aaaactgctg    5640
ctggtgtttt gcttccgtca gcgctggatg cggcgtgcgg tcggcaaaga ccagaccgtt    5700
catacagaac tggcgatcgt tcggcgtatc gccaaaatca ccgccgtaag ccgaccacgg    5760
gttgccgttt tcatcatatt taatcagcga ctgatccacc cagtcccaga cgaagccgcc    5820
ctgtaaacgg ggatactgac gaaacgcctc ccagtattta gcgaaaccgc caagactgtt    5880
acccatcgcg tgggcgtatt cgcaaaggat cagcgggcg tctctccag gtagcgaaag     5940 ccatttttg atggaccatt tcggcacagc cgggaaggg ctggtcttcat ccacgcgcgc     6000 gtacatcggg caaataatat cggtggccgt ggtgtcggct ccgccgcctt catactgcac    6060
cgggcgggaa ggatcgacag atttgatcca gcgatacagc gcgtcgtgat tagcgccgtg    6120
gcctgattca ttccccagcg accagatgat cacactcggg tgattacgat cgcgctgcac    6180
cattcgcgtt acgcgttcgc tcatcgccgg tagccagcgc ggatcatcgg tcagacgatt    6240
cattggcacc atgccgtggg tttcaatatt ggcttcatcc accacataca ggccgtagcg    6300
gtcgcacagc gtgtaccaca gcggatggtt cggataatgc gaacagcgca cggcgttaaa    6360
gttgttctgc ttcatcagca ggatatcctg caccatcgtc tgctcatcca tgacctgacc    6420
atgcagagga tgatgctcgt gacggttaac gcctcgaatc agcaacggct tgccgttcag    6480
cagcagcaga ccattttcaa tccgcacctc gcggaaaccg acatcgcagg cttctgcttc    6540
aatcagcgtg ccgtcggcgg tgtgcagttc aaccaccgca cgatagagat tcgggatttc    6600
ggcgctccac agtttcgggt tttcgacgtt cagacgtagt gtgacgcgat cggcataacc    6660
accacgctca tcgataattt caccgccgaa aggcgcggtg ccgctggcga cctgcgtttc    6720
accctgccat aaagaaactg ttacccgtag gtagtcacgc aactcgccgc acatctgaac    6780
ttcagcctcc agtacagcgc ggctgaaatc atcattaaag cgagtggcaa catggaaatc    6840
gctgatttgt gtagtcggtt tatgcagcaa cgagacgtca cggaaaatgc cgctcatccg    6900
ccacatatcc tgatcttcca gataactgcc gtcactccaa cgcagcacca tcaccgcgag    6960
gcggttttct ccggcgcgta aaatgcgct caggtcaaat tcagacggca aacgactgtc     7020
ctggccgtaa ccgacccagc gcccgttgca ccacagatga aacgccgagt taacgccatc    7080
aaaaataatt cgcgtctggc cttcctgtag ccagctttca tcaacattaa atgtgagcga    7140
gtaacaaccc gtcggattct ccgtgggaac aaacggcgga ttgaccgtaa tgggataggt    7200
tacgttggtg tagatgggcg catcgtaacc gtgcatctgc cagtttgagg gacgacgac     7260 agtatcggcc tcaggaagat cgcactccag ccagctttcc ggcaccgctt ctggtgccgg    7320
aaaccaggca agcgccatt cgccattcag gctgcgcaac tgttgggaag gcgatcggt      7380 gcgggcctct tcgctattac gccagctggc gaaggggga tgtgctgcaa ggcgattaag     7440
ttgggtaacg ccagggtttt cccagtcacg acgttgtaaa acgacgggat ccgccatgtc    7500
acagatcatc aagcttatcg ataccgtcga tccccactgg aaagaccgcg aagagtttgt    7560
```

```
cctcaaccgc gagctgtgga aaaaaaaggg acaggataag tatgacatca tcaaggaaac    7620
cctggactac tgcgccctac agatctgcag cccgggggat ccactagttc tagcctcgag    7680
taggaattcg ataacttcgt ataatgtata ctatacgaag ttatgggtcg atggtgatgc    7740
ttggcaattc gggtcgatgg tgaagcttgg ataacttcgt ataatgtatg ctatacgaag    7800
ttatcaattc gccctatagt gagtcgtatt ctcccgaaaa ccgcttctag caacgaagtt    7860
cctatactat ttgaagaata ggaacttcgg aataggaact tcagctctgt atcgtctatc    7920
gttatgtcta atggtatctg atgcagatct tctgtatcgt ctatcgttat gtctaatggt    7980
atctgatgca gatctgctga agttcctata ctttctagag aataggaact tcggaatagg    8040
aacttcgaat tctcgagggc ccgggctcga ccagctgtgc gcatagtggc ttgaatcgat    8100
aaaataaaag attttattta gtctccagaa aagggggga atgaaagacc ccacctgtag    8160
gtttggcaag ctagcacaac ccctcactcg gggcgccagt cctccgattg actgagtcgc    8220
ccgggtaccc gtgtatccaa taaaccctct tgcagttgca tccgacttgt ggtctcgctg    8280
ttccttggga gggtctcctc tgagtgattg actacccgtc agcgggggtc tttcacatgc    8340
agcatgtatc aaaattaatt tggttttttt tcttaagtat ttacattaaa tggccatagt    8400
tgcattaatg aatcggccaa cgcgcgggga gaggcggttt gcgtattggg cgctcttccg    8460
cttcctcgct cactgactcg ctgcgctcgg tcgttcggct gcggcgagcg gtatcagctc    8520
actcaaaggc ggtaatacgg ttatccacag aatcagggga taacgcagga agaacatgt     8580 gagcaaaagg ccagcaaaag gccaggaacc gtaaaaaggc cgcgttgctg gcgttttcc     8640 ataggctccg ccccccctgac gagcatcaca aaaatcgacg ctcaagtcag aggtggcgaa    8700
acccgacagg actataaaga taccaggcgt ttccccctgg aagctccctc gtgcgctctc    8760
ctgttccgac cctgccgctt accggatacc tgtccgcctt tctcccttcg ggaagcgtgg    8820
cgctttctca tagctcacgc tgtaggtatc tcagttcggt gtaggtcgtt cgctccaagc    8880
tgggctgtgt gcacgaaccc cccgttcagc ccgaccgctg cgccttatcc ggtaactatc    8940
gtcttgagtc caacccggta agacacgact tatcgccact ggcagcagcc actggtaaca    9000
ggattagcag agcgaggtat gtaggcggtg ctacagagtt cttgaagtgg tggcctaact    9060
acggctacac tagaaggaca gtatttggta tctgcgctct gctgaagcca gttaccttcg    9120
gaaaaagagt tggtagctct tgatccggca acaaaccac cgctggtagc ggtggttttt     9180
ttgtttgcaa gcagcagatt acgcgcagaa aaaaaggatc tcaagaagat cctttgatct    9240
tttctacggg gtctgacgct cagtggaacg aaaactcacg ttaagggatt ttggtcatga    9300
gattatcaaa aaggatcttc acctagatcc ttttgcggcc gcaaatcaat ctaaagtata    9360
tatgagtaaa cttggtctga cagttaccaa tgcttaatca gtgaggcacc tatctcagcg    9420
atctgtctat ttcgttcatc catagttgcc tgactccccg tcgtgtagat aactacgata    9480
cgggagggct taccatctgg ccccagtgct gcaatgatac cgcgagaccc acgctcaccg    9540
gctccagatt tatcagcaat aaaccagcca gccggaaggg ccgagcgcag aagtggtcct    9600
gcaactttat ccgcctccat ccagtctatt aattgttgcc gggaagctag agtaagtagt    9660
tcgccagtta atagtttgcg caacgttgtt gccattgctg caggcatcgt ggtgtcacgc    9720
tcgtcgtttg gtatggcttc attcagctcc ggttcccaac gatcaaggcg agttacatga    9780
tcccccatgt tgtgcaaaaa agcggttagc tccttcggtc ctccgatcgt tgtcagaagt    9840
aagttggccg cagtgttatc actcatggtt atggcagcac tgcataattc tcttactgtc    9900
```

| | |
|---|---|
| atgccatccg taagatgctt ttctgtgact ggtgagtact caaccaagtc attctgagaa | 9960 |
| tagtgtatgc ggcgaccgag ttgctcttgc ccggcgtcaa tacgggataa taccgcgcca | 10020 |
| catagcagaa ctttaaaagt gctcatcatt ggaaaacgtt cttcggggcg aaaactctca | 10080 |
| aggatcttac cgctgttgag atccagttcg atgtaaccca ctcgtgcacc caactgatct | 10140 |
| tcagcatctt ttactttcac cagcgtttct gggtgagcaa aaacaggaag gcaaaatgcc | 10200 |
| gcaaaaaagg gaataagggc gacacggaaa tgttgaatac tcatactctt cctttttcaa | 10260 |
| tattattgaa gcatttatca gggttattgt ctcatgagcg gatacatatt tgaatgtatt | 10320 |
| tagaaaaata acaaataggg gttccgcgc acatttcccc gaaaagtgcc ac | 10372 |

```
<210> SEQ ID NO 7
<211> LENGTH: 10501
<212> TYPE: DNA
<213> ORGANISM: Artificial
<220> FEATURE:
<223> OTHER INFORMATION: Retroviral gene trap vector
      eFlip3ROSAbetaGeoPuro

<400> SEQUENCE: 7
```

| | |
|---|---|
| ctgcagcctg aatatgggcc aaacaggata tctgtggtaa gcagttcctg ccccggctca | 60 |
| gggccaagaa cagatggaac agctgaatat gggccaaaca ggatatctgt ggtaagcagt | 120 |
| tcctgccccg gctcagggcc aagaacagat ggtcccaga tgcggtccag ccctcagcag | 180 |
| tttctagaga accatcagat gtttccaggg tgccccaagg acctgaaatg accctgtgcc | 240 |
| ttatttgaac taaccaatca gttcgcttct cgcttctgtt cgcgcgcttc tgctccccga | 300 |
| gctcaataaa agagcccaca cccctcact cggggcgcca gtcctccgat tgactgagtc | 360 |
| gcccgggtac ccgtgtatcc aataaaccct cttgcagttg catccgactt gtggtctcgc | 420 |
| tgttccttgg gagggtctcc tctgagtgat tgactacccg tcagcggggg tctttcattt | 480 |
| gggggctcgt ccgggatcgg gagacccctg cccaggacc accgaccac caccgggagg | 540 |
| caagctggcc agcaacttat ctgtgtctgt ccgattgtct agtgtctatg actgattta | 600 |
| tgcgcctgcg tcggtactag ttagctaact agctctgtat ctggcggacc cgtggtggaa | 660 |
| ctgacgagtt cggaacaccc ggccgcaacc ctggagacg tcccagggac ttcggggcc | 720 |
| gtttttgtgg cccgacctga gtccaaaaat cccgatcgtt ttggactctt tggtgcaccc | 780 |
| cccttagagg agggatatgt ggttctggta ggagacgaga acctaaaaca gttcccgcct | 840 |
| ccgtctgaat ttttgctttc ggtttgggac cgaagccgcg ccgcgcgtct tgtctgctgc | 900 |
| agcatcgttc tgtgttgtct ctgtctgact gtgtttctgt atttgtctga gaattagggc | 960 |
| cagactgtta ccactccctt aagtttgacc ttaggtcact ggaaagatgt cgagcggatc | 1020 |
| gctcacaacc agtcggtaga tgtcaagaag agacgttggg ttaccttctg ctctgcagaa | 1080 |
| tggccaacct ttaacgtcgg atggccgcga cggcacct taaccgaga cctcatcacc | 1140 |
| caggttaaga tcaaggtctt ttcacctggc ccgcatggac acccagacca ggtcccctac | 1200 |
| atcgtgacct gggaagcctt ggcttttgac cccctcct gggtcaagcc ctttgtacac | 1260 |
| cctaagcctc cgcctcctct tcctccatcc gccccgtctc tcccccttga acctcctcgt | 1320 |
| tcgaccccgc ctcgatcctc cctttatcca gccctcactc cttctctagg cgccggccgg | 1380 |
| atccgttgct gaagttccta ttccgaagtt ccattcttc aaatagtata ggaacttcgt | 1440 |
| taacgaagtt cctattccga agttcctatt ctctagaaag tataggaact tctcgtgacg | 1500 |
| gtctcgaagc cgcgggagat ctaattctag atttaagctt ctgatggaat tagaacttgg | 1560 |

```
caaaacaata ctgagaatga agtgtatgtg aacagaggc tgctgatctc gttcttcagg      1620
ctatgaaact gacacatttg gaaaccacag tacttagaac cacaaagtgg gaatcaagag      1680
aaaaacaatg atcccacgag agatctatag atctatagat catgagtggg aggaatgagc      1740
tggcccttaa tttggtttag cttgtttaaa ttatgatatc caactatgaa acattatcat      1800
aaagcaatag taaagagcca cagtaaagag caggcattta tcttaatccc accccacccc      1860
cacccccgta gctccaatcc ttccattcaa aatgtaggta ctctgttctc acccttctta      1920
acaaagtatg acaggaaaaa cttccatttt agtggacatc tttattgttt aatagatcat      1980
caatttctgc agacttacag cggatcccct caggcaccgg gcttgcgggt catgcaccag      2040
gtcgcgcggt ccttcgggca ctcgacgtcg gcggtgacgg tgaagccgag ccgctcgtag      2100
aaggggaggt tgcggggcgc ggaggtctcc aggaaggcgg gcaccccggc gcgctcggcc      2160
gcctccactc cggggagcac gacggcgctg cccagaccct tgccctggtg gtcgggcgag      2220
acgccgacgg tggccaggaa ccacgcgggc tccttgggcc ggtgcggcgc caggaggcct      2280
tccatctgtt gctgcgcggc cagccgggaa ccgctcaact cggccatgcg cgggccgatc      2340
tcggcgaaca ccgccccgc ttcgacgctc tccggcgtgg tccagaccgc caccgcggcg      2400
ccgtcgtccg cgacccacac cttgccgatg tcgagcccga cgcgcgtgag gaagagttct      2460
tgcagctcgg tgacccgctc gatgtggcgg tccggatcga cggtgtggcg cgtggcgggg      2520
tagtcggcga acgcggcggc gagggtgcgt acggccctgg ggacgtcgtc gcgggtggcg      2580
aggcgcaccg tgggcttgta ctcggtcata ttggctgcag gtcgaaaggc ccggagatga      2640
ggaagaggag aacagcgcgg cagacgtgcg cttttgaagc gtgcagaatg ccgggctccg      2700
gaggaccttc gggcgcccgc cccgcccctg agcccgcccc tgagcccgcc cccggaccca      2760 cccttccca gcctctgagc ccagaaagcg aaggagcaaa gctgctattg gccgctgccc      2820
caaaggccta cccgcttcca ttgctcagcg gtgctgtcca tctgcacgag actagtgaga      2880
cgtgctactt ccatttgtca cgtcctgcac gacgcgagct gcgggcgggg gggaacttc      2940 ctgactaggg gaggagtaga aggtggcgcg aaggggccac caaagaacgg agccggttgg      3000
cgcctaccgg tggatgtgga atgtgtgcga ggccagaggc cacttgtgta gcgccaagtg      3060
cccagcgggg ctgctaaagc gcatgctcca gactgccttg ggaaaagcgc ctcccctacc      3120
cggtagaatt ccccgcggtg gagcgaggaa gcggaagagt ctagaataac ttcgtatagt      3180
atacattata cgaagttatg ggtcgatggt gagatctgga ctagagggtc gatggtgatg      3240
cttggataac ttcgtatagc atacattata cgaagttatc ggatcccagt gtggtggtac      3300
tcgaggtcga ctctagagga tcgagcccca gctggttctt tccgtctcag aagccataga      3360
gcccaccgca tccccagcat gcctgctatt gtcttcccaa tcctcccccct tgctgtcctg      3420 ccccacccca cccccagaa tagaatgaca cctactcaga caatgcgatg caatttcctc      3480
attttattag gaaaggacag tgggagtggc accttccagg gtcaaggaag gcacggggga      3540
ggggcaaaca acagatggct ggcaactaga aggcacagtc gaggctgatc agcgagctct      3600
agagaattga tcccctcaga agaactcgtc aagaaggcga tagaaggcga tgcgctgcga      3660
atcgggagcg gcgataccgt aaagcacgag gaagcggtca gcccattcgc cgccaagctc      3720
ttcagcaata tcacgggtag ccaacgctat gtcctgatag cggtccgcca cacccagccg      3780
gccacagtcg atgaatccag aaaagcggcc attttccacc atgatattcg gcaagcaggc      3840
atcgccatgg gtcacgacga gatcctcgcc gtcgggcatg cgcgccttga gcctggcgaa      3900
cagttcggct ggcgcgagcc cctgatgctc ttcgtccaga tcatcctgat cgacaagacc      3960
```

```
ggcttccatc cgagtacgtg ctcgctcgat gcgatgtttc gcttggtggt cgaatgggca    4020
ggtagccgga tcaagcgtat gcagccgccg cattgcatca gccatgatgg atactttctc    4080
ggcaggagca aggtgagatg acaggagatc ctgccccggc acttcgccca atagcagcca    4140
gtcccttccc gcttcagtga caacgtcgag cacagctgcg caaggaacgc ccgtcgtggc    4200
cagccacgat agccgcgctg cctcgtcctg cagttcattc agggcaccgg acaggtcggt    4260
cttgacaaaa agaaccgggc gcccctgcgc tgacagccgg aacacggcgg catcagagca    4320
gccgattgtc tgttgtgccc agtcatagcc gaatagcctc tccacccaag cggccggaga    4380
acctgcgtgc aatccatctt gttcaatggc cgatcccata ttggctgcag cccgggggat    4440
cccctgacac cagaccaact ggtaatggta gcgaccggcg ctcagctgga attccgccga    4500
tactgacggg ctccaggagt cgtcgccacc aatccccata tggaaaccgt cgatattcag    4560
ccatgtgcct tcttccgcgt gcagcagatg gcgatggctg gtttccatca gttgctgttg    4620
actgtagcgg ctgatgttga actggaagtc gccgcgccac tggtgtgggc cataattcaa    4680
ttcgcgcgtc ccgcagcgca gaccgttttc gctcgggaag acgtacgggg tatacatgtc    4740
tgacaatggc agatcccagc ggtcaaaaca ggcggcagta aggcggtcgg atagttttc    4800 ttgcggccct aatccgagcc agtttacccg ctctgctacc tgcgccagct ggcagttcag    4860
gccaatccgc gccggatgcg gtgtatcgct cgccacttca acatcaacgg taatcgccat    4920
ttgaccacta ccatcaatcc ggtaggtttt ccggctgata ataaggtttt cccctgatg    4980 ctgccacgcg tgagcggtcg taatcagcac cgcatcagca agtgtatctg ccgtgcactg    5040
caacaacgct gcttcggcct ggtaatggcc cgccgccttc agcgttcga cccaggcgtt    5100 agggtcaatg cgggtcgctt cacttacgcc aatgtcgtta ccagcggtg cacgggtgaa    5160 ctgatcgcgc agcggcgtca gcagttgttt tttatcgcca atccacatct gtgaaagaaa    5220
gcctgactgg cggttaaatt gccaacgctt attacccagc tcgatgcaaa aatccatttc    5280
gctggtggtc agatgcggga tggcgtggga cgcggcgggg agcgtcacac tgaggttttc    5340
cgccagacgc cactgctgcc aggcgctgat gtgcccggct tctgaccatg cggtcgcgtt    5400
cggttgcact acgcgtactg tgagccagag ttgcccggcg ctctccggct gcggtagttc    5460
aggcagttca atcaactgtt taccttgtgg agcgacatcc agaggcactt caccgcttgc    5520
cagcggctta ccatccagcg ccaccatcca gtgcaggagc tcgttatcgc tatgacggaa    5580
caggtattcg ctggtcactt cgatggtttg cccggataaa cggaactgga aaaactgctg    5640
ctggtgtttt gcttccgtca gcgctggatg cggcgtgcgg tcggcaaaga ccagaccgtt    5700
catacagaac tggcgatcgt tcggcgtatc gccaaaatca ccgccgtaag ccgaccacgg    5760
gttgccgttt tcatcatatt taatcagcga ctgatccacc cagtcccaga cgaagccgcc    5820
ctgtaaacgg ggatactgac gaaacgcctg ccagtattta gcgaaaccgc caagactgtt    5880
acccatcgcg tgggcgtatt cgcaaaggat cagcgggcgc gtctctccag gtagcgaaag    5940 ccatttttg atggaccatt tcggcacagc cgggaagggc tggtcttcat ccacgcgcgc    6000
gtacatcggg caaataatat cggtggccgt ggtgtcggct ccgccgcctt catactgcac    6060
cgggcgggaa ggatcgacag atttgatcca gcgatacagc gcgtcgtgat tagcgccgtg    6120
gcctgattca ttccccagcg accagatgat cacactcggg tgattacgat cgcgctgcac    6180
cattcgcgtt acgcgttcgc tcatcgccgg tagccagcgc ggatcatcgg tcagacgatt    6240
cattggcacc atgccgtggg tttcaatatt ggcttcatcc accacataca ggccgtagcg    6300
```

```
gtcgcacagc gtgtaccaca gcggatggtt cggataatgc gaacagcgca cggcgttaaa    6360
gttgttctgc ttcatcagca ggatatcctg caccatcgtc tgctcatcca tgacctgacc    6420
atgcagagga tgatgctcgt gacggttaac gcctcgaatc agcaacggct tgccgttcag    6480
cagcagcaga ccattttcaa tccgcacctc gcggaaaccg acatcgcagg cttctgcttc    6540
aatcagcgtg ccgtcggcgg tgtgcagttc aaccaccgca cgatagagat cgggatttc    6600 ggcgctccac agtttcgggt tttcgacgtt cagacgtagt gtgacgcgat cggcataacc    6660
accacgctca tcgataattt caccgccgaa aggcgcggtg ccgctggcga cctgcgtttc    6720
accctgccat aaagaaactg ttacccgtag gtagtcacgc aactcgccgc acatctgaac    6780
ttcagcctcc agtacagcgc ggctgaaatc atcattaaag cgagtggcaa catggaaatc    6840
gctgatttgt gtagtcggtt tatgcagcaa cgagacgtca cggaaaatgc cgctcatccg    6900
ccacatatcc tgatcttcca gataactgcc gtcactccaa cgcagcacca tcaccgcgag    6960
gcggttttct ccggcgcgta aaatgcgct caggtcaaat tcagacggca aacgactgtc    7020
ctggccgtaa ccgacccagc gcccgttgca ccacagatga aacgccgagt taacgccatc    7080
aaaaataatt cgcgtctggc cttcctgtag ccagctttca tcaacattaa atgtgagcga    7140
gtaacaaccc gtcggattct ccgtgggaac aaacggcgga ttgaccgtaa tgggataggt    7200
tacgttggtg tagatgggcg catcgtaacc gtgcatctgc cagtttgagg ggacgacgac    7260
agtatcggcc tcaggaagat cgcactccag ccagctttcc ggcaccgctt ctggtgccgg    7320
aaaccaggca aagcgccatt cgccattcag gctgcgcaac tgttgggaag ggcgatcggt    7380
gcgggcctct tcgctattac gccagctggc gaaaggggga tgtgctgcaa ggcgattaag    7440
ttgggtaacg ccagggtttt cccagtcacg acgttgtaaa acgacgggat ccgccatgtc    7500
acagatcatc aagcttatcg ataccgtcga tccccactgg aaagaccgcg aagagtttgt    7560
cctcaaccgc gagctgtgga aaaaaaggg acaggataag tatgacatca tcaaggaaac    7620
cctggactac tgcgccctac agatctgcag cccgggggat ccactagttc tagcctcgag    7680
taggaattcg ataacttcgt ataatgtata ctatacgaag ttatgggtcg atggtgatgc    7740
ttggcaattc gggtcgatgg tgaagcttgg ataacttcgt ataatgtatg ctatacgaag    7800
ttatcaattc gccctatagt gagtcgtatt ctcccgaaaa ccgcttctag caacgaagtt    7860
cctatactat ttgaagaata ggaacttcgg aataggaact tcagcagatc tgcttttcca    7920
tttgcatttc aaatgtgatt ttaacttaca ttatacaaag ctgaaaggtc agtgcaggat    7980
ctgcttttcc atttgcattt caaatgtgat tttaacttac attatacaaa gctgaaaggt    8040
cagtgcagga tctgcttttc catttgcatt tcaaatgtga ttttaactta cattatacaa    8100
agctgaaagg tcagtgcagg atctgctgaa gttcctatac tttctagaga ataggaactt    8160
cggaatagga acttcgaatt ctcgagggcc cgggctcgac cagctgtgcg catagtggct    8220
tgaatcgata aaataaaaga ttttatttag tctccagaaa aaggggggaa tgaagaccc    8280 cacctgtagg tttggcaagc tagcacaacc cctcactcgg ggcgccagtc tccgattga    8340 ctgagtcgcc cgggtacccg tgtatccaat aaaccctctt gcagttgcat ccgacttgtg    8400
gtctcgctgt tccttgggag ggtctcctct gagtgattga ctacccgtca gcggggtct    8460 ttcacatgca gcatgtatca aaattaattt ggttttttt cttaagtatt tacattaaat    8520
ggccatagtt gcattaatga atcggccaac gcgcggggag aggcggtttg cgtattgggc    8580
gctcttccgc ttcctcgctc actgactcgc tgcgctcggt cgttcggctg cggcgagcgg    8640
tatcagctca ctcaaaggcg gtaatacggt tatccacaga atcaggggat aacgcaggaa    8700
```

```
agaacatgtg agcaaaaggc cagcaaaagg ccaggaaccg taaaaaggcc gcgttgctgg    8760
cgttttccca taggctccgc cccctgacg agcatcacaa aaatcgacgc tcaagtcaga    8820
ggtggcgaaa cccgacagga ctataaagat accaggcgtt tccccctgga agctccctcg    8880
tgcgctctcc tgttccgacc ctgccgctta ccggatacct gtccgccttt ctcccttcgg    8940
gaagcgtggc gctttctcat agctcacgct gtaggtatct cagttcggtg taggtcgttc    9000
gctccaagct gggctgtgtg cacgaacccc cgttcagcc cgaccgctgc gccttatccg    9060
gtaactatcg tcttgagtcc aacccggtaa gacacgactt atcgccactg gcagcagcca    9120
ctggtaacag gattagcaga gcgaggtatg taggcggtgc tacagagttc ttgaagtggt    9180
ggcctaacta cggctacact agaaggacag tatttggtat ctgcgctctg ctgaagccag    9240
ttaccttcgg aaaaagagtt ggtagctctt gatccggcaa acaaaccacc gctggtagcg    9300
gtggtttttt tgtttgcaag cagcagatta cgcgcagaaa aaaggatctc aagaagatc    9360 ctttgatctt ttctacgggg tctgacgctc agtggaacga aaactcacgt taagggattt    9420
tggtcatgag attatcaaaa aggatcttca cctagatcct tttgcggccg caaatcaatc    9480
taaagtatat atgagtaaac ttggtctgac agttaccaat gcttaatcag tgaggcacct    9540
atctcagcga tctgtctatt tcgttcatcc atagttgcct gactccccgt cgtgtagata    9600
actacgatac gggagggctt accatctggc cccagtgctg caatgatacc gcgagaccca    9660
cgctcaccgg ctccagattt atcagcaata aaccagccag ccggaagggc cgagcgcaga    9720
agtggtcctg caactttatc cgcctccatc cagtctatta attgttgccg ggaagctaga    9780
gtaagtagtt cgccagttaa tagtttgcgc aacgttgttg ccattgctgc aggcatcgtg    9840
gtgtcacgct cgtcgtttgg tatggcttca ttcagctccg gttcccaacg atcaaggcga    9900
gttacatgat cccccatgtt gtgcaaaaaa gcggttagct ccttcggtcc tccgatcgtt    9960
gtcagaagta agttggccgc agtgttatca ctcatggtta tggcagcact gcataattct   10020
cttactgtca tgccatccgt aagatgcttt tctgtgactg gtgagtactc aaccaagtca   10080
ttctgagaat agtgtatgcg gcgaccgagt tgctcttgcc cggcgtcaat acggataat   10140 accgcgccac atagcagaac tttaaaagtg ctcatcattg gaaaacgttc ttcggggcga   10200
aaactctcaa ggatcttacc gctgttgaga tccagttcga tgtaacccac tcgtgcaccc   10260
aactgatctt cagcatcttt tactttcacc agcgtttctg ggtgagcaaa aacaggaagg   10320
caaaatgccg caaaaaaggg aataagggcg acacggaaat gttgaatact catactcttc   10380 cttttcaat attattgaag catttatcag ggttattgtc tcatgagcgg atacatattt   10440
gaatgtattt agaaaaataa acaaataggg gttccgcgca catttccccg aaaagtgcca   10500
c                                                                   10501
```

<210> SEQ ID NO 8
<211> LENGTH: 10710
<212> TYPE: DNA
<213> ORGANISM: Artificial
<220> FEATURE:
<223> OTHER INFORMATION: Retroviral gene trap vector
      eFlip6ROSAbetaGeoPuro

<400> SEQUENCE: 8

```
ctgcagcctg aatatgggcc aaacaggata tctgtggtaa gcagttcctg ccccggctca      60
gggccaagaa cagatggaac agctgaatat gggccaaaca ggatatctgt ggtaagcagt     120
tcctgccccg gctcagggcc aagaacagat ggtccccaga tgcggtccag ccctcagcag     180
```

```
tttctagaga accatcagat gtttccaggg tgccccaagg acctgaaatg accctgtgcc      240
ttatttgaac taaccaatca gttcgcttct cgcttctgtt cgcgcgcttc tgctccccga      300
gctcaataaa agagcccaca acccctcact cggggcgcca gtcctccgat tgactgagtc      360
gcccgggtac ccgtgtatcc aataaaccct cttgcagttg catccgactt gtggtctcgc      420
tgttccttgg gagggtctcc tctgagtgat tgactacccg tcagcggggg tctttcattt      480
gggggctcgt ccgggatcgg gagaccctg cccaggacc accgaccac caccgggagg       540 caagctggcc agcaacttat ctgtgtctgt ccgattgtct agtgtctatg actgatttta      600
tgcgcctgcg tcggtactag ttagctaact agctctgtat ctggcggacc cgtggtggaa      660
ctgacgagtt cggaacaccc ggccgcaacc ctgggagacg tcccagggac ttcggggggcc     720 gttttgtgg cccgacctga gtccaaaaat cccgatcgtt ttggactctt tggtgcaccc      780
cccttagagg agggatatgt ggttctggta ggagacgaga acctaaaaca gttcccgcct      840
ccgtctgaat ttttgctttc ggtttgggac cgaagccgcg ccgcgcgtct tgtctgctgc      900
agcatcgttc tgtgttgtct ctgtctgact gtgtttctgt atttgtctga gaattagggc      960
cagactgtta ccactcccttt aagtttgacc ttaggtcact ggaaagatgt cgagcggatc      1020
gctcacaacc agtcggtaga tgtcaagaag agacgttggg ttaccttctg ctctgcagaa      1080
tggccaacct ttaacgtcgg atggccgcga gacggcacct ttaaccgaga cctcatcacc      1140
caggttaaga tcaaggtctt ttcacctggc ccgcatggac acccagacca ggtcccctac      1200
atcgtgacct gggaagcctt ggcttttgac ccccctccct gggtcaagcc ctttgtacac      1260
cctaagcctc cgcctcctct tcctccatcc gccccgtctc tcccccttga acctcctcgt      1320
tcgaccccgc ctcgatcctc cctttatcca gccctcactc cttctctagg cgccggccgg      1380
atccgttgct gaagttccta ttccgaagtt cctattcttc aaatagtata ggaacttcgt      1440
taacgaagtt cctattccga agttcctatt ctctagaaag tataggaact tctcgtgacg      1500
gtctcgaagc cgggagatct aattctagat ttaagcttct gatggaatta gaacttggca      1560
aaacaatact gagaatgaag tgtatgtgga acagaggctg ctgatctcgt tcttcaggct      1620
atgaaactga cacatttgga aaccacagta cttagaacca caaagtggga atcaagagaa      1680
aaacaatgat cccacgagag atctatagat ctatagatca tgagtgggag gaatgagctg      1740
gcccttaatt tggtttagct tgtttaaatt atgatatcca actatgaaac attatcataa      1800
agcaatagta aagagccaca gtaaagagca ggcatttatc ttaatcccac cccacccca       1860 cccccgtagc tccaatcctt ccattcaaaa tgtaggtact ctgttctcac ccttcttaac      1920
aaagtatgac aggaaaaact tccatttag tggacatctt tattgtttaa tagatcatca      1980
atttctgcag acttacagcg gatccctca ggcaccgggc ttgcgggtca tgcaccaggt       2040
cgcgcggtcc ttcgggcact cgacgtcggc ggtgacggtg aagccgagcc gctcgtagaa      2100
ggggaggttg cggggcgcgg aggtctccag gaaggcgggc accccggcgc gctcggccgc      2160
ctccactccg gggagcacga cggcgctgcc cagacccttg ccctggtggt cgggcgagac      2220
gccgacggtg gccaggaacc acgcgggctc cttgggccgg tgcggcgcca ggaggccttc      2280
catctgttgc tgcgcggcca gccgggaacc gctcaactcg ccatgcgcg ggccgatctc       2340 ggcgaacacc gccccgcttc gacgctctc cggcgtggtc cagaccgcca ccgcggcgcc       2400
gtcgtccgcg acccacacct tgccgatgtc gagcccgacg cgcgtgagga agagttcttg      2460
cagctcggtg acccgctcga tgtggcggtc cggatcgacg gtgtggcgcg tggcggggta      2520
```

```
gtcggcgaac gcggcggcga gggtgcgtac ggccctgggg acgtcgtcgc gggtggcgag    2580
gcgcaccgtg ggcttgtact cggtcatatt ggctgcaggt cgaaaggccc ggagatgagg    2640
aagaggagaa cagcgcggca gacgtgcgct tttgaagcgt gcagaatgcc gggctccgga    2700
ggaccttcgg gcgcccgccc cgccctgag cccgccctg agcccgcccc cggacccacc      2760
ccttcccagc ctctgagccc agaaagcgaa ggagcaaagc tgctattggc cgctgcccca    2820
aaggcctacc cgcttccatt gctcagcggt gctgtccatc tgcacgagac tagtgagacg    2880
tgctacttcc atttgtcacg tcctgcacga cgcgagctgc ggggcggggg ggaacttcct    2940
gactagggga ggagtagaag gtggcgcgaa ggggccacca agaacggag ccggttggcg      3000 cctaccggtg gatgtggaat gtgtgcgagg ccagaggcca cttgtgtagc gccaagtgcc    3060
cagcggggct gctaaagcgc atgctccaga ctgccttggg aaaagcgcct cccctacccg    3120
gtagaattcc ccggtggagc gaggaagcgg aagagtctag aataacttcg tatagtatac    3180
attatacgaa gttatgggtc gatggtgaga tctggactag agggtcgatg gtgatgcttg    3240
gataacttcg tatagcatac attatacgaa gttatcggat cccagtgtgg tggtactcga    3300
ggtcgactct agaggatcga gccccagctg gttctttccg tctcagaagc catagagccc    3360
accgcatccc cagcatgcct gctattgtct tcccaatcct ccccttgct gtcctgcccc     3420 accccacccc ccagaataga atgacaccta ctcagacaat gcgatgcaat ttcctcattt    3480
tattaggaaa ggacagtggg agtggcacct tccagggtca aggaaggcac ggggagggg    3540 caaacaacag atggctggca actagaaggc acagtcgagg ctgatcagcg agctctagag    3600
aattgatccc ctcagaagaa ctcgtcaaga aggcgataga aggcgatgcg ctgcgaatcg    3660
ggagcggcga taccgtaaag cacgaggaag cggtcagccc attcgccgcc aagctcttca    3720
gcaatatcac gggtagccaa cgctatgtcc tgatagcggt ccgccacacc cagccggcca    3780
cagtcgatga atccagaaaa gcggccattt tccaccatga tattcggcaa gcaggcatcg    3840
ccatgggtca cgacgagatc ctcgccgtcg gcatgcgcg ccttgagcct ggcgaacagt     3900
tcggctggcg cgagcccctg atgctcttcg tccagatcat cctgatcgac aagaccggct    3960
tccatccgag tacgtgctcg ctcgatgcga tgtttcgctt ggtggtcgaa tgggcaggta    4020
gccggatcaa gcgtatgcag ccgccgcatt gcatcagcca tgatggatac tttctcggca    4080
ggagcaaggt gagatgacag gagatcctgc cccggcactt cgcccaatag cagccagtcc    4140
cttcccgctt cagtgacaac gtcgagcaca gctgcgcaag gaacgcccgt cgtggccagc    4200
cacgatagcc gcgctgcctc gtcctgcagt tcattcaggg caccggacag tcggtcttg     4260 acaaaaagaa ccgggcgccc ctgcgctgac agccggaaca cggcggcatc agagcagccg    4320
attgtctgtt gtgcccagtc atagccgaat agcctctcca cccaagcggc cggagaacct    4380
gcgtgcaatc catcttgttc aatggccgat cccatattgg ctgcagcccg ggggatcccc    4440
tgacaccaga ccaactggta atggtagcga ccggcgctca gctggaattc cgccgatact    4500
gacgggctcc aggagtcgtc gccaccaatc cccatatgga aaccgtcgat attcagccat    4560
gtgccttctt ccgcgtgcag cagatggcga tggctggttt ccatcagttg ctgttgactg    4620
tagcggctga tgttgaactg gaagtcgccg cgccactggt gtgggccata attcaattcg    4680
cgcgtcccgc agcgcagacc gttttcgctc gggaagacgt acggggtata catgtctgac    4740
aatggcagat cccagcggtc aaaacaggcg cagtaaggc ggtcgggata gttttcttgc     4800
ggccctaatc cgagccagtt tacccgctct gctacctgcg ccagctggca gttcaggcca    4860
atccgcgccg gatgcggtgt atcgctcgcc acttcaacat caacggtaat cgccatttga    4920
```

```
ccactaccat caatccggta ggttttccgg ctgataaata aggttttccc ctgatgctgc   4980
cacgcgtgag cggtcgtaat cagcaccgca tcagcaagtg tatctgccgt gcactgcaac   5040
aacgctgctt cggcctggta atggcccgcc gccttccagc gttcgaccca ggcgttaggg   5100
tcaatgcggg tcgcttcact tacgccaatg tcgttatcca gcggtgcacg ggtgaactga   5160
tcgcgcagcg gcgtcagcag ttgtttttta tcgccaatcc acatctgtga agaaagcct   5220 gactggcggt taaattgcca acgcttatta cccagctcga tgcaaaaatc catttcgctg   5280
gtggtcagat gcgggatggc gtgggacgcg gcggggagcg tcacactgag gttttccgcc   5340
agacgccact gctgccaggc gctgatgtgc ccggcttctg accatgcggt cgcgttcggt   5400
tgcactacgc gtactgtgag ccagagttgc ccggcgctct ccggctgcgg tagttcaggc   5460
agttcaatca actgtttacc ttgtggagcg acatccagag gcacttcacc gcttgccagc   5520
ggcttaccat ccagcgccac catccagtgc aggagctcgt tatcgctatg acggaacagg   5580
tattcgctgg tcacttcgat ggtttgcccg gataaacgga actggaaaaa ctgctgctgg   5640
tgttttgctt ccgtcagcgc tggatgcggc gtgcggtcgg caaagaccag accgttcata   5700
cagaactggc gatcgttcgg cgtatcgcca aaatcaccgc cgtaagccga ccacgggttg   5760
ccgttttcat catatttaat cagcgactga tccacccagt cccagacgaa gccgccctgt   5820
aaacggggat actgacgaaa cgcctgccag tatttagcga aaccgccaag actgttaccc   5880
atcgcgtggg cgtattcgca aaggatcagc gggcgcgtct ctccaggtag cgaaagccat   5940
tttttgatgg accatttcgg cacagccggg aagggctggt cttcatccac gcgcgcgtac   6000
atcgggcaaa taatatcggt ggccgtggtg tcggctccgc cgccttcata ctgcaccggg   6060
cgggaaggat cgacagattt gatccagcga tacagcgcgt cgtgattagc gccgtggcct   6120
gattcattcc ccagcgacca gatgatcaca ctcgggtgat tacgatcgcg ctgcaccatt   6180
cgcgttacgc gttcgctcat cgccggtagc cagcgcggat catcggtcag acgattcatt   6240
ggcaccatgc cgtgggtttc aatattggct tcatccacca catacaggcc gtagcggtcg   6300
cacagcgtgt accacagcgg atggttcgga taatgcgaac agcgcacggc gttaaagttg   6360
ttctgcttca tcagcaggat atcctgcacc atcgtctgct catccatgac ctgaccatgc   6420
agaggatgat gctcgtgacg gttaacgcct cgaatcagca acggcttgcc gttcagcagc   6480
agcagaccat tttcaatccg cacctcgcgg aaaccgacat cgcaggcttc tgcttcaatc   6540
agcgtgccgt cggcggtgtg cagttcaacc accgcacgat agagattcgg gatttcggcg   6600
ctccacagtt tcgggttttc gacgttcaga cgtagtgtga cgcgatcggc ataaccacca   6660
cgctcatcga taatttcacc gccgaaaggc gcggtgccgc tggcgacctg cgtttcaccc   6720
tgccataaag aaactgttac ccgtaggtag tcacgcaact cgccgcacat ctgaacttca   6780
gcctccagta cagcgcggct gaaatcatca ttaaagcgag tggcaacatg gaaatcgctg   6840
atttgtgtag tcgtttatg cagcaacgag acgtcacgga aaatgccgct catccgccac   6900
atatcctgat cttccagata actgccgtca ctccaacgca gcaccatcac cgcgaggcgg   6960
ttttctccgg cgcgtaaaaa tgcgctcagg tcaaattcag acggcaaacg actgtcctgg   7020
ccgtaaccga cccagcgccc gttgcaccac agatgaaacg ccgagttaac gccatcaaaa   7080
ataattcgcg tctggccttc ctgtagccag cttttcatcaa cattaaatgt gagcgagtaa   7140
caacccgtcg gattctccgt gggaacaaac ggcggattga ccgtaatggg ataggttacg   7200
ttggtgtaga tgggcgcatc gtaaccgtgc atctgccagt ttgaggggac gacgacagta   7260
```

```
tcggcctcag gaagatcgca ctccagccag ctttccggca ccgcttctgg tgccggaaac      7320
caggcaaagc gccattcgcc attcaggctg cgcaactgtt gggaagggcg atcggtgcgg      7380
gcctcttcgc tattacgcca gctggcgaaa gggggatgtg ctgcaaggcg attaagttgg      7440
gtaacgccag ggttttccca gtcacgacgt tgtaaaacga cgggatccgc catgtcacag      7500
atcatcaagc ttatcgatac cgtcgatccc cactggaaag accgcgaaga gtttgtcctc      7560
aaccgcgagc tgtggaaaaa aaagggacag gataagtatg acatcatcaa ggaaccctg      7620 gactactgcg ccctacagat ctgcagcccg ggggatccac tagttctagc ctcgagtagg      7680
aattcgataa cttcgtataa tgtatactat acgaagttat gggtcgatgg tgatgcttgg      7740
caattcgggt cgatggtgaa gcttggataa cttcgtataa tgtatgctat acgaagttat      7800
caattcgccc tatagtgagt cgtattctcc gaaaaccgc ttctagcaac gaagttccta      7860
tactatttga agaataggaa cttcggaata ggaacttcag cagatctgct tttccatttg      7920
catttcaaat gtgattttaa cttacattat acaaagctga aggtcagtg caggatctgc      7980 ttttccattt gcatttcaaa tgtgatttta acttacatta tacaaagctg aaaggtcagt      8040
gcaggatctg cttttccatt tgcatttcaa atgtgatttt aacttacatt atacaaagct      8100
gaaaggtcag tgcaggatct gcttttccat ttgcatttca aatgtgattt taacttacat      8160
tatacaaagc tgaaaggtca gtgcaggatc tgcttttcca tttgcatttc aaatgtgatt      8220
ttaacttaca ttatacaaag ctgaaaggtc agtgcaggat ctgcttttcc atttgcattt      8280
caaatgtgat tttaacttac attatacaaa gctgaaaggt cagtgcagga tctgctgaag      8340
ttcctatact ttctagagaa taggaacttc ggaataggaa cttcgaattc tcgagggccc      8400
gggctcgacc agctgtgcgc atagtggctt gaatcgataa aataaaagat tttatttagt      8460
ctccagaaaa aggggggaat gaaagacccc acctgtaggt ttggcaagct agcacaaccc      8520
ctcactcggg gcgccagtcc tccgattgac tgagtcgccc gggtaccgt gtatccaata      8580 aaccctcttg cagttgcatc cgacttgtgg tctcgctgtt ccttgggagg gtctcctctg      8640
agtgattgac tacccgtcag cgggggtctt tcacatgcag catgtatcaa aattaatttg      8700
gttttttttc ttaagtattt acattaaatg gccatagttg cattaatgaa tcggccaacg      8760
cgcggggaga ggcggtttgc gtattgggcg ctcttccgct tcctcgctca ctgactcgct      8820
gcgctcggtc gttcggctgc ggcgagcggt atcagctcac tcaaaggcgg taatacggtt      8880
atccacagaa tcaggggata acgcaggaaa gaacatgtga gcaaaaggcc agcaaaaggc      8940
caggaaccgt aaaaaggccg cgttgctggc gtttttccat aggctccgcc cccctgacga      9000
gcatcacaaa aatcgacgct caagtcagag gtggcgaaac ccgacaggac tataaagata      9060
ccaggcgttt ccccctggaa gctccctcgt gcgctctcct gttccgaccc tgccgcttac      9120
cggatacctg tccgcctttc tcccttcggg aagcgtggcg ctttctcata gctcacgctg      9180
taggtatctc agttcggtgt aggtcgttcg ctccaagctg ggctgtgtgc acgaaccccc      9240
cgttcagccc gaccgctgcg ccttatccgg taactatcgt cttgagtcca acccggtaag      9300
acacgactta tcgccactgg cagcagccac tggtaacagg attagcagag cgaggtatgt      9360
aggcggtgct acagagttct tgaagtggtg gcctaactac ggctacacta aggacagt      9420 atttggtatc tgcgctctgc tgaagccagt taccttcgga aaaagagttg gtagctcttg      9480
atccggcaaa caaaccaccg ctggtagcgg tggtttttt gtttgcaagc agcagattac      9540
gcgcagaaaa aaaggatctc aagaagatcc tttgatcttt tctacggggt ctgacgctca      9600
gtggaacgaa aactcacgtt aagggatttt ggtcatgaga ttatcaaaaa ggatcttcac      9660
```

```
ctagatcctt ttgcggccgc aaatcaatct aaagtatata tgagtaaact tggtctgaca    9720
gttaccaatg cttaatcagt gaggcaccta tctcagcgat ctgtctattt cgttcatcca    9780
tagttgcctg actccccgtc gtgtagataa ctacgatacg ggagggctta ccatctggcc    9840
ccagtgctgc aatgataccg cgagacccac gctcaccggc tccagattta tcagcaataa    9900
accagccagc cggaagggcc gagcgcagaa gtggtcctgc aactttatcc gcctccatcc    9960
agtctattaa ttgttgccgg gaagctagag taagtagttc gccagttaat agttgcgca   10020 acgttgttgc cattgctgca ggcatcgtgg tgtcacgctc gtcgtttggt atggcttcat   10080
tcagctccgg ttcccaacga tcaaggcgag ttacatgatc ccccatgttg tgcaaaaaag   10140
cggttagctc cttcggtcct ccgatcgttg tcagaagtaa gttggccgca gtgttatcac   10200
tcatggttat ggcagcactg cataattctc ttactgtcat gccatccgta agatgctttt   10260
ctgtgactgg tgagtactca accaagtcat tctgagaata gtgtatgcgg cgaccgagtt   10320
gctcttgccc ggcgtcaata cgggataata ccgcgccaca tagcagaact ttaaaagtgc   10380
tcatcattgg aaaacgttct cggggcgaaa actctcaag gatcttaccg ctgttgagat   10440
ccagttcgat gtaacccact cgtgcaccca actgatcttc agcatctttt actttcacca   10500
gcgtttctgg gtgagcaaaa acaggaaggc aaaatgccgc aaaaaaggga taagggcga    10560 cacggaaatg ttgaatactc atactcttcc tttttcaata ttattgaagc atttatcagg   10620
gttattgtct catgagcgga tacatatttg aatgtattta gaaaaataaa caaatagggg   10680
ttccgcgcac atttccccga aaagtgccac                                    10710

<210> SEQ ID NO 9
<211> LENGTH: 20
<212> TYPE: DNA
<213> ORGANISM: Artificial
<220> FEATURE:
<223> OTHER INFORMATION: primer I1

<400> SEQUENCE: 9
cgcctcctct tcctccatcc                                                20

<210> SEQ ID NO 10
<211> LENGTH: 40
<212> TYPE: DNA
<213> ORGANISM: Artificial
<220> FEATURE:
<223> OTHER INFORMATION: primer I3

<400> SEQUENCE: 10
actcttccgc ttcctcgctc caccgcggct tcgagaccgt                          40

<210> SEQ ID NO 11
<211> LENGTH: 20
<212> TYPE: DNA
<213> ORGANISM: Artificial
<220> FEATURE:
<223> OTHER INFORMATION: primer I2

<400> SEQUENCE: 11
gggcctcttc gctattacgc                                                20

<210> SEQ ID NO 12
<211> LENGTH: 40
<212> TYPE: DNA
<213> ORGANISM: Artificial
<220> FEATURE:
```

```
<223> OTHER INFORMATION: primer I4

<400> SEQUENCE: 12
acggtctcga agccgcggtg gagcgaggaa gcggaagagt                    40

<210> SEQ ID NO 13
<211> LENGTH: 20
<212> TYPE: DNA
<213> ORGANISM: Artificial
<220> FEATURE:
<223> OTHER INFORMATION: primer I6

<400> SEQUENCE: 13
gctcctcgcc cttgctcacc                                         20

<210> SEQ ID NO 14
<211> LENGTH: 40
<212> TYPE: DNA
<213> ORGANISM: Artificial
<220> FEATURE:
<223> OTHER INFORMATION: primer I8

<400> SEQUENCE: 14
tagaagcggt tttcgggaga atacgactca ctatagggcg                    40

<210> SEQ ID NO 15
<211> LENGTH: 20
<212> TYPE: DNA
<213> ORGANISM: Artificial
<220> FEATURE:
<223> OTHER INFORMATION: primer I5

<400> SEQUENCE: 15
tgctggcctt ttgctcacat                                         20

<210> SEQ ID NO 16
<211> LENGTH: 40
<212> TYPE: DNA
<213> ORGANISM: Artificial
<220> FEATURE:
<223> OTHER INFORMATION: primer I7

<400> SEQUENCE: 16
cgccctatag tgagtcgtat tctcccgaaa accgcttcta                    40

<210> SEQ ID NO 17
<211> LENGTH: 71
<212> TYPE: DNA
<213> ORGANISM: Artificial
<220> FEATURE:
<223> OTHER INFORMATION: oligonucleotide P5

<400> SEQUENCE: 17
gatcctgcac tgacctttca gctttgtata atgtaagtta aaatcacatt tgaaatgcaa    60
atggaaaagc a                                                  71

<210> SEQ ID NO 18
<211> LENGTH: 71
<212> TYPE: DNA
<213> ORGANISM: Artificial
<220> FEATURE:
<223> OTHER INFORMATION: oligonucleotide P6

<400> SEQUENCE: 18
gatctgcttt tccatttgca tttcaaatgt gattttaact tacattatac aaagctgaaa    60
```
ggtcagtgca g            71

<210> SEQ ID NO 19
<211> LENGTH: 45
<212> TYPE: DNA
<213> ORGANISM: Artificial
<220> FEATURE:
<223> OTHER INFORMATION: primer P7

<400> SEQUENCE: 19
gggggctgca gacttacagc ggatcccctc aggcaccggg cttgc            45

<210> SEQ ID NO 20
<211> LENGTH: 36
<212> TYPE: DNA
<213> ORGANISM: Artificial
<220> FEATURE:
<223> OTHER INFORMATION: primer P8

<400> SEQUENCE: 20
gggggctgca gccaatatga ccgagtacaa gcccac            36

<210> SEQ ID NO 21
<211> LENGTH: 48
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: 36..46
<223> OTHER INFORMATION: n represents inosine at positions 36, 37, 40,
      41, 45 and 46

<400> SEQUENCE: 21
ctactactac taggccacgc gtcgactagt acgggnnggn ngggnngg            48

<210> SEQ ID NO 22
<211> LENGTH: 22
<212> TYPE: DNA
<213> ORGANISM: Artificial
<220> FEATURE:
<223> OTHER INFORMATION: primer

<400> SEQUENCE: 22
gccagggttt tcccagtcac ga            22

<210> SEQ ID NO 23
<211> LENGTH: 32
<212> TYPE: DNA
<213> ORGANISM: Artificial
<220> FEATURE:
<223> OTHER INFORMATION: primer

<400> SEQUENCE: 23
ctactactac taggccacgc gtcgactagt ac            32

<210> SEQ ID NO 24
<211> LENGTH: 38
<212> TYPE: DNA
<213> ORGANISM: Artificial
<220> FEATURE:
<223> OTHER INFORMATION: primer

<400> SEQUENCE: 24
tgtaaaacga cggccagtgt gaaggctgtg cgaggccg            38

<210> SEQ ID NO 25
<211> LENGTH: 21
<212> TYPE: DNA
<213> ORGANISM: Artificial
<220> FEATURE:
<223> OTHER INFORMATION: oligonucleotide I16

<400> SEQUENCE: 25
cgagccccag ctggttcttt c                                              21

<210> SEQ ID NO 26
<211> LENGTH: 25
<212> TYPE: DNA
<213> ORGANISM: Artificial
<220> FEATURE:
<223> OTHER INFORMATION: oligonucleotide SR1

<400> SEQUENCE: 26
gctagcttgc caaacctaca ggtgg                                          25

<210> SEQ ID NO 27
<211> LENGTH: 21
<212> TYPE: DNA
<213> ORGANISM: Artificial
<220> FEATURE:
<223> OTHER INFORMATION: oligonucleotide I15

<400> SEQUENCE: 27
gtctcagaag ccatagagcc c                                              21

<210> SEQ ID NO 28
<211> LENGTH: 24
<212> TYPE: DNA
<213> ORGANISM: Artificial
<220> FEATURE:
<223> OTHER INFORMATION: oligonucleotide ISR2

<400> SEQUENCE: 28
gccaaaccta caggtggggt cttt                                           24

<210> SEQ ID NO 29
<211> LENGTH: 22
<212> TYPE: DNA
<213> ORGANISM: Artificial
<220> FEATURE:
<223> OTHER INFORMATION: oligonucleotide I14

<400> SEQUENCE: 29
actatcccga ccgccttact gc                                             22

<210> SEQ ID NO 30
<211> LENGTH: 22
<212> TYPE: DNA
<213> ORGANISM: Artificial
<220> FEATURE:
<223> OTHER INFORMATION: oligonucleotide iPCRu3

<400> SEQUENCE: 30
cctccgattg actgagtcgc cc                                             22

<210> SEQ ID NO 31
<211> LENGTH: 22
<212> TYPE: DNA
<213> ORGANISM: Artificial
<220> FEATURE:

```
<223> OTHER INFORMATION: oligonucleotide I13

<400> SEQUENCE: 31
tgttttgacc gctgggatct gc                                              22

<210> SEQ ID NO 32
<211> LENGTH: 22
<212> TYPE: DNA
<213> ORGANISM: Artificial
<220> FEATURE:
<223> OTHER INFORMATION: oligonucleotide iPCRu4

<400> SEQUENCE: 32
tacccgtgta tccaataaac cc                                              22

<210> SEQ ID NO 33
<211> LENGTH: 64
<212> TYPE: DNA
<213> ORGANISM: mus musculus

<400> SEQUENCE: 33
tctttgtttc tttcagcttt gtataagtaa gttaaaatca catttgaaat gcaaatggaa     60
aagc                                                                  64
```

ENHANCER-CONTAINING GENE TRAP VECTORS FOR RANDOM AND TARGETED GENE TRAPPING

The present invention relates to a novel class of gene trap vectors for efficiently identifying silent or weakly expressed target genes in mammalian genomes, methods of their production and methods for identifying and mutating target genes. The gene trap vectors of the present invention can also be used for inducing the expression of silent genes and enhancing the expression of weakly expressed genes. The use of the enhanced gene trap vectors for creating transgenic organisms to study gene function and to validate pharmaceutical compounds prior to clinical applications is a further aspect of the present invention. The novel gene trap vectors as referred to herein are termed as "enhanced gene trap vectors" (eGTV).

BACKGROUND OF THE INVENTION

In the past few years, a variety of gene trap vectors have been shown as being useful tools for the identification and analysis of permanently or transiently expressed genes. Standard gene trap vectors are DNA or retroviral vectors that insert a promoterless reporter gene into a large number of chromosomal sites. A classic gene trap vector integrates into introns, which are the non-expressed regions of a gene. Introns are flanked by exons, which are the expressed regions of a gene. Transcription of a trapped mammalian gene yields a primary messenger RNA consisting of exon, intron and vector sequences. Primary mRNA processing removes the intron sequences and splices the exons together at specific sites (splice sites) located at the 5' and 3' ends of each exon. As a result, the gene trap vector sequences encoding for the reporter gene become associated with the upstream exons in a processed fusion transcript from which a truncated cellular protein is translated together with the reporter protein.

With the completion of sequencing of the human and mouse genomes, the interest in tools suitable for performing genome-wide mutagenesis has significantly increased. Large scale insertional mutagenesis in mammalian cells has been most effectively induced with conventional gene trap vectors (Hansen, J. et al., Proc. Natl. Acad. Sci. USA 100:9918-22 (2003); Skarnes, W. C. et al., Nat. Genet. 36:543-4 (2004); Wiles, M. V. et al., Nat. Genet. 24:13-4 (2000); Zambrowicz, B. P. et al., Proc. Natl. Acad. Sci. USA 100:14109-14 (2003)). When selecting genes by means of their expression, recombinants will be obtained in which the reporter gene is fused to the regulatory elements of an endogenous gene. Transcripts generated by these gene fusion faithfully reflect the activity of individual cellular genes and serve as molecular tags to identify and/or clone any genes linked to specific functions. Thus, gene trap vectors simultaneously mutate and report on the expression of an endogenous gene at the site of insertion and provide a DNA tag for a rapid identification of the disrupted gene. The application of this technique in a genome-wide manner should allow for the identification of most, if not all, active transcripts in a genome and is thus an important tool for genome annotation. More importantly, gene trapping in mouse embryonic stem (ES) cells enables the establishment of ES cell libraries with mutations in a substantial fraction of genes in the mouse genome, which can be used to produce transgenic mice[24]. Thus, the gene trapping methodology enables the analysis of gene function in the context of an entire organism.

For some years targeted mutagenesis in pluripotent mouse embryonic stem (ES) cells has been used to inactivate genes for which cloned sequences were available (Capecchi, M. R., Trends Genet. 5:70-6 (1989)). Since ES cells can pass mutations induced in vitro to transgenic offspring in vivo, it is possible to analyze the consequences of gene disruptions in the context of entire organisms. As a result, numerous mouse strains with functionally inactivated genes ("knock out mice") have been created by this technology. However, targeted mutagenesis requires detailed knowledge of gene structure and organization as well as its physical isolation in a cloning vector. Overall, the generation of mutant mouse strains by this procedure is still time consuming, labor intensive, expensive and inefficient because it can handle only one gene at the time.

The principal element of a standard gene trap vector is a gene disruption and selection cassette (GDSC) consisting of a promoterless reporter gene and/or selectable marker gene flanked by an upstream 3' splice site (splice acceptor; SA) and a downstream transcriptional termination sequence (polyadenylation sequence; polyA; see FIG. 1). The GDSC is inserted into an intron of a target gene and transcription takes place from the upstream target gene promoter. Since the 3' end of the exon upstream of the vector insertion is flanked by a splice donor (SD) site, it is spliced to the GDSC resulting in a fusion transcript in which the upstream exons of the trapped gene are fused in frame to the reporter and/or selectable marker gene. Due to the presence of a polyA sequence in the GDSC, transcription is terminated prematurely, and, as a result, any exon(s) downstream of the GDSC are not transcribed anymore. Consequently, the processed fusion transcript encodes a truncated form of the target gene, consisting of the upstream exon(s), and the reporter/selectable marker gene.

From the above it becomes apparent that standard gene trap vectors can only disrupt genes that are actively transcribed in the target cell. Genes that are not expressed or expressed only too weakly for detection, i.e. at low expression levels, cannot be recovered by standard gene trapping. This poses a significant problem for genome-wide mutagenesis programs seeking a large scale and cost-effective functional analysis of the ~30,000 mammalian genes. In mouse embryonic stem (ES) cells, for example, only about one half of all genes are expressed, leaving ~15,000 genes inaccessible to standard gene trapping. The overall impact of a gene trap resource for elucidating gene function in vivo will thus rest on the fraction of the genome that is accessible with the standard gene trapping technology.

In order to trap genes that are not accessible to standard trapping, gene trap vectors that can be activated independently of gene expression have been developed previously. These vectors are based on a selectable marker gene flanked upstream by a constitutive promoter and downstream by a 5' splice site (splice donor, SD) (Zambrowicz, B. P. et al., Nature 392:608-11 (1998)). These elements are inserted downstream of a standard GDSC such as described above.

An insertion of these standard vectors into an intron of a gene induces splicing of the selectable marker gene, which, in turn, becomes associated with the downstream exon(s) of that gene. As a result, the cells express a fusion transcript initiating at the constitutive promoter and terminating at the polyA site of the trapped gene (=polyA trap). Since the selectable marker gene is expressed independently of the trapped gene's expression, poly-A traps should, at least in principle, enable the recovery of mutations in any gene.

However, there are some major drawbacks with these gene trap vectors and gene trapping methods. Several large scale screening efforts in ES cells with this technology have shown that polyA-containing gene trap vectors generate a high number of false positive recombinants and, more importantly, are not considered to be highly mutagenic (Zambrowicz, B. P. et al., Proc. Natl. Acad. Sci. USA 100: 14109-14 (2003)). So far two main reasons have been cited for their poor performance: (i) the vectors frequently acquire cryptic polyA sites on the non-coding strands of genes, and (ii) selection is biased for gene trap insertions close to the 3' ends of genes, which are frequently non-mutagenic.

From the above it follows that there exists a need for gene trap vectors and gene trapping methods that overcome the above drawbacks, and which are efficient in the identification and mutation of cellular genes that are either not expressed or expressed too weakly to be detected by standard detection methodology. Thus, the provision of a gene trap strategy making most, if not all, genes of a genome accessible to effective trapping in a target cell would be highly desirable.

The problem underlying the present invention can thus be regarded as the provision of a gene trap vector and a gene targeting cassette that allows for the identification of gene products that are normally not expressed or expressed at non-detectable expression levels in a mammalian target cells. The solution provided by the present invention thus concerns a gene trap vector (eGTV) as defined in independent claim 1.

SUMMARY OF THE INVENTION

The present invention relates to a novel class of gene trap vectors that are capable of targeting genes independently of their expression.

In a first aspect of the invention, the gene trap vector of the invention comprises a gene disruption and selection cassette (GDSC) and at least one cell type-specific enhancer element that can be placed at any site within the vector, preferably upstream of the GDSC.

In a further aspect of the invention ubiquitous enhancer elements may be used. Such ubiquitous enhancer elements are e.g. the aldolase A enhancer (Moch C. et al., Gene Expr. 6:1-14 (1996)), the ployoma virus enhancer (Tanimoto K., et al., Nucleic Acids Res. 27:3130-3137 (1999)), the Oct-1 enhancer (Kemler I. et al., Nucleic Acids Res. 19:237-242 (1991)), and the murine adenosine desamidase enhancer (Winston J. H. et al., Somat. Cell Mol. Genet. 22:261-278 (1996)).

In a further aspect the gene trap vector of the invention comprises more than one enhancer element upstream and/or downstream of the GDSC. The GDSC of the invention comprises from 5' to 3': a splice acceptor sequence, a reporter gene and/or selectable marker gene and a transcription termination site. Preferably the transcription termination site comprises a polyA stretch consisting of adenylic acid (poly A) repeats.

In another aspect the enhancer elements of the present invention are located downstream of a target gene promoter and contain binding sites for transcription activating factors. Preferred enhancer elements of the invention are of the class of responsive elements containing repeat units of specific recognition sites for the corresponding enhancer element-binding partners.

In a further preferred embodiment, the enhancer elements are stretches of nucleic acid sequences of natural or synthetic, viral or non-viral origin that bind transcription activating factors in a sequence-specific manner. Examples are enhancer elements comprising hormone responsive elements, transcription factor binding elements, viral enhancer elements. Enhancer elements of the invention may comprise transcription factor binding sites for AP-1, AP-2, CRE, SRE, NF-kB, SRF, SP1, Oct1, Oct2, Oct3, Oct4 transcription factor binding sites. Preferably, the transcription factor binding sites are arranged as tandem repeats.

In a further aspect the enhanced gene trap vector of the invention comprises recombinase recognition elements for introducing GDSC inversions by site-specific recombinases. Examples of such recognition elements are FRT and IoxP recombination target sequences.

In a preferred embodiment, the gene trap vector of the invention contains one or more Oct-4 responsive enhancer elements that are inserted between two homotypic or heterotypic site-specific recombination targets (RTs).

In a preferred embodiment the reporter gene of the GDSC is β-galactosidase and the selectable marker gene is the neomycinphosphotransferase spliced together in a fusion gene.

In a preferred embodiment, the gene disruption and selection cassette (GDSC) and the enhancer element(s) are integrated in a retrovirus or a plasmid.

Preferred embodiments of retroviral gene trap vectors are FlipROSAβgeo, eFlip3ROSAβgeo and eFlip6ROSAβgeo comprising a puromycin resistance gene inserted downstream of the GDSC allowing for the quantification of gene trap insertions (WO 01/29208).

In another aspect, the present invention relates to a method for generating a transgenic non-human organism comprising
(i) incorporation of a gene trapping construct of the present invention into a cell of said non-human organism; and
(ii) selection of cells in which said gene trapping construct is incorporated in a gene.

In a preferred embodiment of said method, it is suitable for identifying and/or isolating of a target gene in a non-human organism and comprises the steps:
(i) incorporation of a gene trapping construct according to the present invention in a vertebrate cell;
(ii) selection of cells in which the gene trapping construct is incorporated in a gene; and optionally
(iii) identification and/or isolation of the gene in which said gene trapping construct is incorporated.

In yet another aspect of the present invention, the gene trap vector can be used for mutating a target gene in a mammalian cell. The method for mutating a target gene in a mammalian cell, comprises
(i) transfection/infection of said cell with a gene trapping construct according to the present invention;
(ii) incorporation of the gene trapping construct into the target gene, wherein the incorporation results in a truncated non-functional expression product.

It thus follows that the gene trap vectors of the present invention can be used for detecting, identifying or mutating a functional gene in a cell.

In another aspect, the gene trap vectors of the invention can be used for the generation of a gene trap library comprising gene trap insertions identified by the gene trapping methods of the present invention.

In a further aspect, the gene trap vectors of the invention can be used for targeted gene trapping in combination with homologous recombination.

In another aspect, the gene trap vectors of the invention can be used to create mouse mutant strains which are, among others, useful as models for genetic human disease and for validation of pharmaceutical compounds by monitoring in vivo effects of said compounds.

DEFINITIONS

Figure 1:
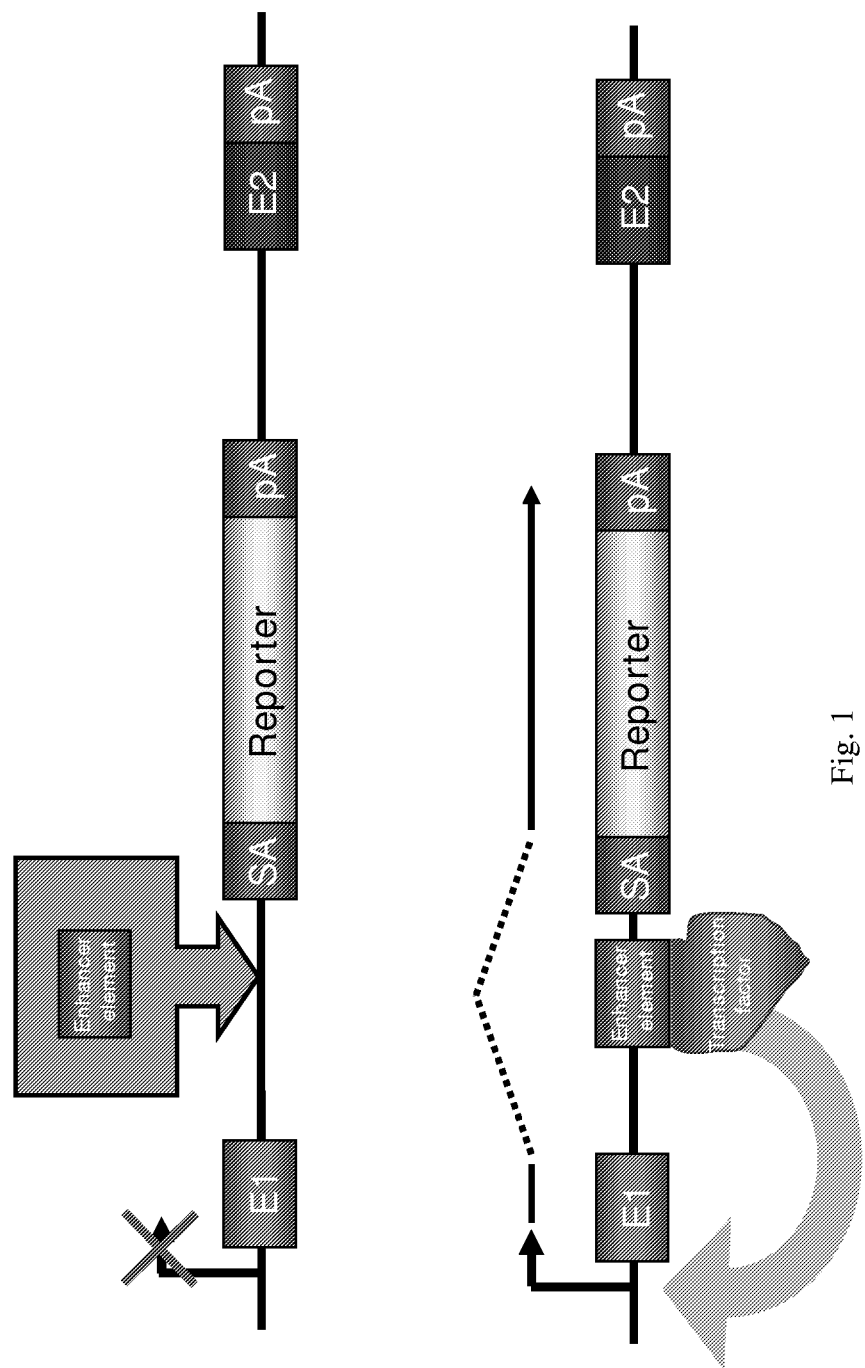
FIG. 1: Mechanism of eGTV activation. Insertion of enhancer elements binding a cell type specific transcription factor along with a gene disruption and selection cassette (GDSC) into an intron of a silent gene leads to its activation. SA=splice acceptor, pA=polyadenylation sequence.

"Upstream" refers to nucleotide sequences that precede the codons specifying the mRNA or that precede (are on the 5' side of) the protein coding sequence.

"Downstream" refers to nucleotide sequences that follow the codons specifying the mRNA or that follow (are on the 3' side of) the protein coding sequence.

"Target Gene" defines a specific locus on a chromosome consisting of exons and introns to be trapped by a gene trap vector.

"Transcription activating factor" refers to a compound, e.g. a protein, polypeptide or peptide that has the ability of inducing gene expression by binding to a specific nucleic acid sequence (DNA, RNA).

"Transcription factor" refers to a compound, such as a protein, polypeptide or peptide that binds to one or more transcription factor recognition sites in the proximity of a gene promoter resulting in an activation of mRNA synthesis of said gene.

"Silent promoter" refers to a promoter that is not activated and consequently does not express the gene under control of this promoter.

"Silent gene" refers to a gene that is not expressed.

"Weakly expressed gene" refers to a gene, which is expressed at low expression level, wherein said expression levels are lower than that of a normally expressed gene. Also encompassed by the terms "weakly expressed" are a number of copies of the expression product that is too low to be detected by conventional standard detection methods.

"Gene disruption and selection cassette (GDSC)" refers to genetic elements comprising from 5' to 3' a splice acceptor sequence, a reporter and/or selection gene and a transcription termination site (e.g. poly A repeats).

"Gene trapping" refers to a random mutagenesis approach in functional genomics and is based on the random integration of a gene disruption and selection cassette into a genome.

"Targeted trapping" refers to a gene specific mutagenesis approach in functional genomics and is based on the insertion of a GDSC into the genome by homologous recombination.

"Gene trap vector" refers to a promoterless gene trapping construct consisting of nucleic acid, wherein the gene trapping construct is capable of generating a fusion transcript with the targeted endogenous gene. The presence of splice acceptor elements in the gene trap vector results in the generation of a fusion protein after its insertion into introns.

"Enhanced gene trap vector" (eGTV) refers to a gene trap vector, which contains one or more enhancer elements in addition to a gene disruption and selection cassette (GDSC).

"Reporter gene" refers to a gene encoding for a gene product (e.g. CAT, β galactosidase, βgeo, GFP, EGFP, alkaline phosphatase) that can be readily detected by standard biochemical assays.

"Selectable marker gene" refers to a gene whose expression in a transfected cell allows for the isolation of gene trap vector-expressing cells in drug-containing media (e.g. neomycin, puromycin, diphtheria toxin).

"PolyA" (A=adenylic acid) refers to a nucleic acid sequence that comprises the AAUAAA consensus sequence, which enables polyadenylation of a processed transcript. In a gene disruption or selection cassette (GDSC), the polyA sequence is located downstream to the reporter and/or selectable marker gene and signals the end of the transcript to the RNA-polymerase.

"Splicing" refers to the process by which non-coding regions (introns) are removed from primary RNA transcripts to produce mature messenger RNA (mRNA) containing only exons.

"5' splice site" (splice donor SD)" and "3' splice site" (splice acceptor SA) refer to intron flanking consensus sequences that mark the sites of splicing.

"Enhancer element" or "enhancer" refers to a nucleic acid sequence, which can increase the levels of transcription of a gene into messenger RNA. Typically, an enhancer element functions in either orientation and at various distances from a cellular promoter.

"Responsive enhancer element" refers to an enhancer element, which is specific for a particular transcription factor. When bound by the specific transcription factor, the levels of expression of the gene are enhanced. An example is the Oct-4 responsive element (ORE), which in combination with the transcription factor Oct-4 increases the gene's expression level.

"GDSC inversion" refers to an aberration in which a GDSC segment is deleted, reinserted and turned by 180 degrees from its original orientation, so that the gene sequence for the segment is reversed with respect to that of the rest of the chromosome. Said inversions can by accomplished by using recombinase enzymes (e.g. Cre, FLPe, φC31).

"Tandem repeats" refers to copies of genetic elements repeated one after another along a genomic or vector site.

"Homotypic" means being of the same type or form.

"Heterotypic" means being of different type or form.

"ROSA" (Reverse-Orientation-Splice-Acceptor) refers to a gene trap cassette inserted into a retroviral backbone in reverse transcriptional orientation relative to the retrovirus (Friedrich, G., Soriano, P., Genes Dev. 5:1513-1523 (1991)).

| Sequence Listing | |
|---|---|
| SEQ ID NO: | free text |
| 1 | FlipROSAβGeo(int) |
| 2 | pBABErfl |
| 3 | FlipROSAβGeo |
| 4 | eFlip3ROSAβGeo |

-continued

Sequence Listing

| SEQ ID NO: | free text |
|---|---|
| 5 | eFlip6ROSAβGeo |
| 6 | FlipROSAβGeoPuro |
| 7 | eFlip3ROSAβGeoPuro |
| 8 | eFlip6ROSAβGeoPuro |
| 9-16 | primer I1, I3, I2, I4, I6, I8, I5 and I7 |
| 17-18 | oligonucleotides P5 and P6 |
| 19-20 | primer P7 and P8 |
| 21-24 | primer |
| 25-32 | oligonucleotides I16, SR1, I15, ISR2, I14, iPCRu3, I13 and iPCRu4 |

DETAILED DESCRIPTION OF THE INVENTION

The present invention relates to a novel class of gene trap vectors with the ability to trap silent or weakly expressed genes in a vertebrate genome. More specifically, the gene trap vectors and gene trapping constructs of the invention allow for trapping genes that are expressed at a low expression level, i.e. genes that usually escape detection by standard detection methods because the copy number of their expressed products is too low to be detectable by standard detection methodology (e.g. by utilization of antibodies in Western blotting or ELISA (enzyme-linked immunosorbent assay). This novel class of gene trap vectors will be in the following referred to as "enhanced gene trap vectors" (eGTV).

The invention is based on the finding that the expression of a silent or weakly expressed gene can be induced or enhanced by using a gene trap vector construct that contains one or more enhancer elements capable of activating the trapped gene's promoter. This, in turn, activates gene trap expression, which enables further analysis of the gene. By using enhancer elements that are responsive to cell type specific transcription factors in gene trap vectors, it is possible to disrupt genes that are not accessible to standard methodology.

Gene trap vectors have been designed containing a standard GDSC in combination with at least one enhancer element that can insert either randomly (gene trapping) or specifically (targeted gene trapping) throughout the genome. It is preferred that the gene trap vectors of the invention integrate in non-expressed sites of the genome (introns), i.e. between the expressed regions (exons) of a gene. Following transcriptional activation of the trapped gene by means of the inserted enhancer elements, a fusion transcript is generated between the upstream exons and the GDSC resulting in a selectable mutation. To determine the identity of the trapped gene, the fusion transcript can be reverse transcribed, amplified by PCR and subsequently sequenced.

Conventional gene trap vectors and classic gene targeting methods require gene expression for the successful mutagenesis of target genes. However, genes that are not actively transcribed cannot be disrupted by these methods. Depending on the cell type, between 50-80% of all genes are not transcribed under natural conditions because the cell does either not require the gene product for survival and proliferation, or because the cell has ceased to differentiate any further.

We therefore sought to provide a gene trap vector with the ability to either induce gene expression or to enhance gene expression of a target gene. To achieve this, the gene trap vectors of the invention contain at least one enhancer element serving as a binding site for transcription activating molecules that, when bound, are able to turn on the transcription of the trapped gene.

The gene trap vectors of the invention are equipped with cell type specific enhancer elements that are placed into the target genes upon vector insertion. It is preferred that one, two or more enhancer elements are arranged within the gene trap vector depending on the degree of activation and/or class of genes to be analyzed. The enhancer elements can be placed at various distances from the promoter of the gene of interest, preferably they are arranged downstream of the promoter region. In preferred embodiments, the enhancer elements are of natural or synthetic, viral or non-viral origin and bind transcriptional activators. In yet another preferred embodiment of the invention, the enhancer elements comprise responsive elements such as hormone responsive elements, transcription factor binding elements, and viral enhancer elements. The specific selection of the enhancer elements will depend on the cell type and class of genes to be analyzed. In a further preferred embodiment, the enhancer elements comprise binding sites of the following transcription factors: AP-1, AP-2, CRE, SRE, NF-kB, SRF, SP1, Oct1, Oct2, Oct3, Oct4 (Nakabeppu, Y. et al., Cell 55:907-15 (1988); Bosher, J. M. et al., Oncogene 13:1707-7 (1996); Gotquin, V. et al., Genes Dev. 12 2073-90 (1998); Scholer, H. R. et al., Nature 344:435-9 (1990)). Preferably, the transcription factor binding sites are arranged as tandem repeats.

The binding of a transcription factor to its cognate enhancer element induces the expression of silent genes and enhances the expression of weakly expressed genes. By activating gene expression, the enhancer-bound transcription factors also activate the inserted enhanced gene trap vector (eGTV) of the invention in much the same way than standard gene trap cassettes are activated, however, with the advantages referred to below. Thus, by using the enhanced gene trap vectors of the invention, it is possible to identify and select genes that would normally escape such a selection (see FIG. 1).

Figure 2:
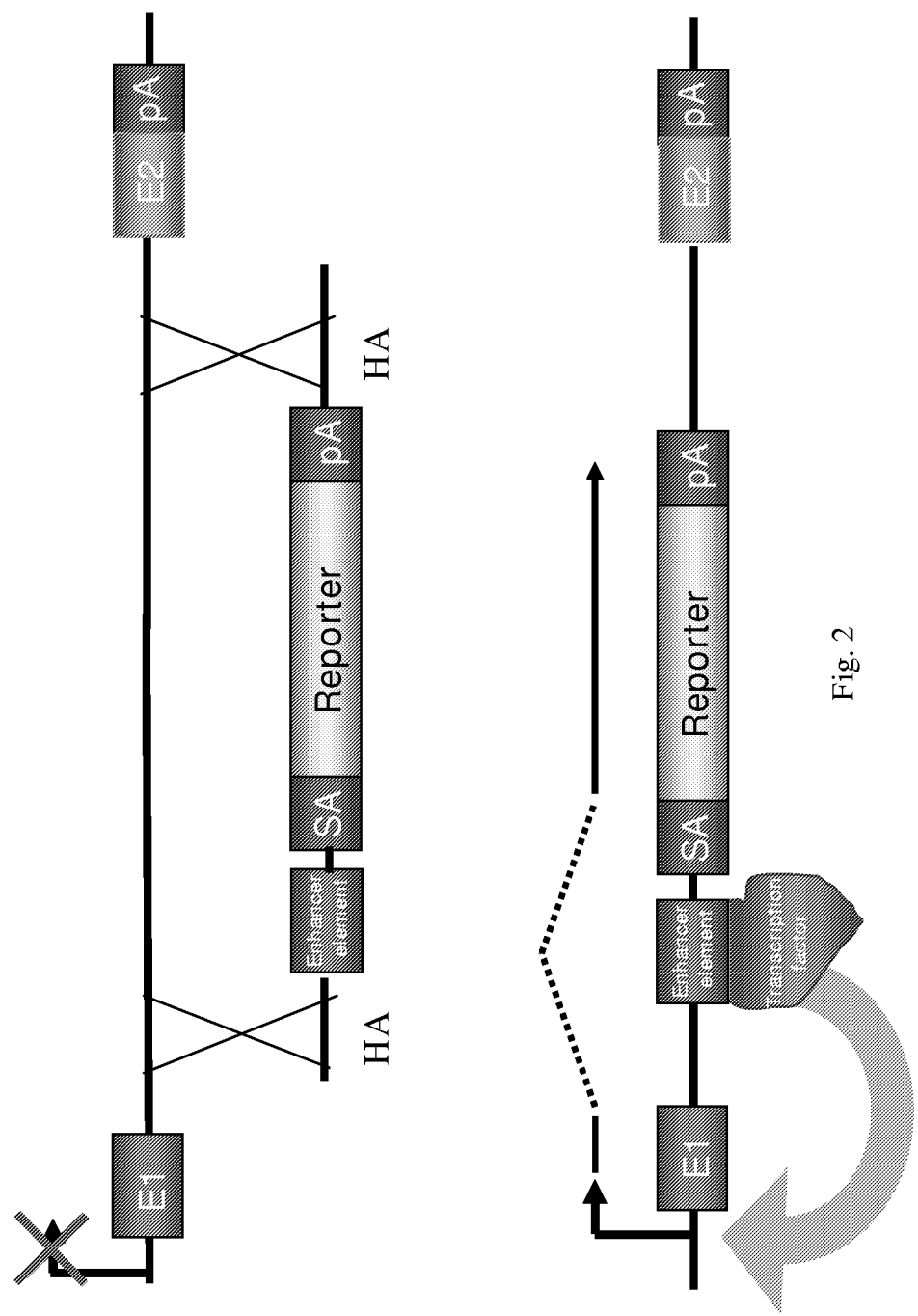
FIG. 2: Enhanced target-directed gene trapping (targeted trapping). A GDSC is inserted together with enhancer elements binding a specific transcription factor into the intron of a silent target gene by homologous recombination. The eGTV activates gene expression and enables drug selection of homologous recombinants. SA=splice acceptor, pA=polyadenylation sequence, HA=homology arms.

The enhanced gene trap vectors of the present invention are not only suitable for random mutagenesis but can also be used for targeted gene trapping involving the introduction of a GDSC along with one or more specific enhancer elements into a silent gene by homologous recombination (see FIG. 2). The activation of a target gene by specifically binding a transcription factor simultaneously activates the GDSC, and thus enables the recovery of homologous recombinants by drug selection. The number of genes accessible to trapping in a particular target cell is thereby increased above the number of genes accessible to standard trapping (see examples).

Figure 3:
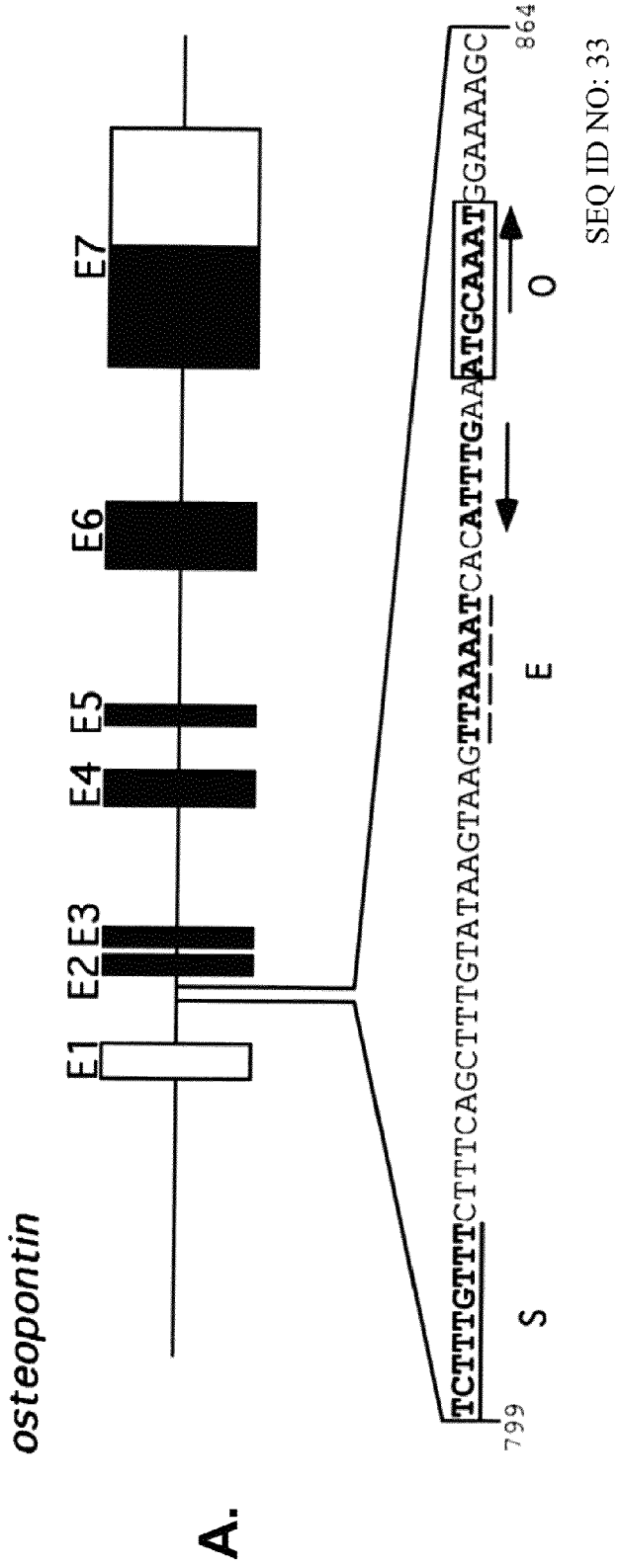
FIG. 3: The Oct-4 intronic enhancer of the osteopontin gene. (A.) Position of the Oct-4 enhancer in the osteopontin gene. (B.) Sequence of the Oct-4 responsive element (ORE) used in the eGTV vectors. The Sox2 (S) binding sequence has been inactivated by mutagenesis. O=Oct-4 binding sequence, E=engrailed binding sequence.

In a preferred embodiment, these enhancer elements include intronic Oct-4 enhancer elements derived from the osteopontin gene (see FIG. 3). Oct-4 is a transcription factor, which is highly and specifically expressed in undifferentiated embryonic stem (ES) cells (Scholer, H. R. et al., Nature 344:435-9 (1990)). The Oct-4 transcription factor specifically recognizes and binds to the conserved octamer motif -ATG-CAAAT-, which is present in Oct-4 enhancers (see FIG. 3). In ES cells, insertions of a gene trap vector of the invention comprising Oct-4 responsive enhancer elements (OREs) into the introns of silent or weakly expressed genes will activate these genes by binding the Oct-4 transcription factor (see examples). This, in turn, induces GDSC expression, which enables selection for gene trap events.

It is preferred that the reporter gene of the invention is γ-galactosidase, βgeo or a gene encoding for a luminescent gene, e.g. a fluorescent gene such as green fluorescent protein (GFP) or firefly luciferase. It is further preferred that the selectable marker gene encodes an anti-antibiotic such as neomycin- and hygromycin-phosphotransferases or puromycin-acetyl-transferase.

In another aspect of the invention, the gene trap vectors comprise target sequences for site-specific recombinases to enable postinsertional GDSC inversions and/or excisions. Thus, in an embodiment the enhanced gene trap vectors of this aspect of the invention contains: (i) a GDSC consisting of a β-galactosidase-neomycinphosphotransferase fusion gene (βgeo) flanked by SA- and polyA-sequences for gene trapping, (ii) elements enabling GDSC inversions by site specific recombinases for conditional mutagenesis, and (iii) one or more Oct-4 responsive enhancer elements (ORE), preferably inserted between two heterotypic site-specific recombination targets (RTs) (see FIG. 3).

Any suitable recombinase can be used for inversion, such as Cre recombinase, Flp recombinase or φC31 recombinase.

It is preferred that the gene trap vectors of the invention are contained in a retrovirus or a plasmid. These gene trapping constructs contain in addition to a GDSC at least one enhancer element for transcriptional activation of an upstream or downstream gene promoter. Retroviruses insert a single copy of the reporter and/or selectable marker cassette per locus, with no rearrangement of flanking sequences. In particular, retroviruses have a preference for insertions at the 5' ends of genes.

The gene trap vectors of the invention are preferably retroviral gene trap vectors selected from the group consisting of FlipROSAβgeo, eFlip3ROSAβgeo and eFlip6ROSAβgeo (WO 01/29208). These vectors preferably comprise a puromycin resistance gene inserted downstream of the GDSC allowing for the quantification of most if not all gene trap insertions.

The above specified retroviral or plasmid based gene trap vectors are suitable for disrupting both silent and expressed genes across any mammalian genome (e.g. human, mouse). For example, by using the gene trap vectors of the invention in a genome wide manner, a large collection of embryonic stem (ES) cell lines harboring gene trap insertions in single genes can be assembled and used to make mutant mice. In particular, for pharmaceutical research seeking to validate the utility of specific genes and their products as targets for drug development, mutant mice are excellent genetic tools.

In another aspect, the invention relates to a method for the identification of a functional yet silent gene in mammalian cells. The method comprises the transduction of cells with an enhanced gene trap vector as described herein and the incorporation of the reporter gene and/or selectable marker cassette into genomic sites. If the vector inserts into the intron of silent genes, gene trap vector-induced promoter activation results in GDSC expression, which in turn enables cell selection. Preferably, the disrupted gene is identified by RT-PCR (RACE) or PCR (PCR=polymerase chain reaction; RT=reverse transcription) (Hansen, J. et al., Proc. Natl. Acad. Sci. USA 100:9918-22 (2003); von Melchner et al., Proc. Natl. Acad. Sci. USA 87:3733-7 (1990)).

In a preferred embodiment, the method of the present invention is adapted to reach a cost-effective saturation of the genome with insertional mutations in the fastest possible way. The steps involved in this method are: (i) transducing a large number of embryonic stem (ES) cells with enhanced gene trap vectors (eGTV) of the invention, (ii) selecting eGTV-expressing clones and establishing cell lines from them, (iii) creating an ES cell bank containing ES cell lines with mutations in single genes, (iv) amplifying genomic sequences adjacent to the eGTV insertion by PCR and/or sequences appended to eGTV transcripts by RT-PCR (RACE) from the ES cell lines, (v) sequencing the amplification products to obtain cell line specific gene trap sequence tags (GTSTs, "flank bank"), (vi) identifying and cataloguing the disrupted genes by GTST homology searches in the public databases, (vii) making mutant strains of mice using ES cells from the ES cell bank.

The invention further encompasses a method for mutating a functional gene within the genome. The mutation is introduced by incorporating a gene trap vector of the invention into intronic sites of a gene. As a result of the splicing process (see supra), a fusion product will be obtained comprising one or more exons of the gene and the reporter/selectable marker gene cassette. Due to the fact that transcription terminates at the polyA site, the downstream exons of the gene will not be part of the fusion product. Therefore, the mRNA of the gene is not complete but truncated since every exon that follows the gene trap vector will not be expressed.

A further aspect of the invention relates to a method for producing both "null" and "conditional" mutations in genes of an organism regardless of whether the genes are expressed or not. In a preferred embodiment the method comprises the following steps:
(i) incorporation of a gene trapping vector construct in a suitable cell;
(ii) selection of cells having the vector construct incorporated in a gene by expression analysis of the selectable marker;
(iii) identification and/or isolation of the gene in which the construct is incorporated by PCR or Reverse Transcriptase (RT)-PCR.

The gene trap vectors of the invention and their uses allow both random or targeted mutagenesis in mammalian cells. For a targeted-insertional mutagenesis (=targeted gene trapping), sequence information of the gene of interest is required for specific integration, whereas in a random insertional mutagenesis the integration occurs at non-specific sites. A method for targeted-insertional mutagenesis using enhanced targeted gene trapping constructs of the present invention comprises the following steps:
(i) design of a gene trapping construct comprising the enhancer elements and the GDSC from an enhanced gene trap vector flanked by sequences homologous to the an intron preferably flanking a 5' exon of the specific target gene (=homology arms; see FIG. 2);
(ii) transduction of the gene trapping construct into a suitable cell;
(iii) isolation of homologous recombinants by selecting for GDSC expression;
(iv) verification of homologous recombination in the selected cells by a suitable detection method, preferably 5' RACE, genomic PCR or Southern blot analysis.

Taken together the enhanced gene trap vectors (eGTV) of the invention and the methods employing them are suitable to solve the drawbacks of conventional gene trap- and gene targeting vectors currently used in the field. In particular, it shows that the eGTV have the capability to
(i) induce mutations in genes regardless of their expression, including genes for which cloned sequences are not available;
(ii) increase the number of genes accessible to trapping and targeted trapping in comparison to the number presently accessible by standard gene trap and targeted trapping vectors;
(iii) increase the gene trapping rate by reducing redundancy, and thereby saving costs.

In its application to pharmaceutical research, the eGTV technology greatly assists the creation of a library of ES cell clones, which includes all genes of the mouse genome (~30, 000), modified by the insertion of an eGTV vector. Sequence analysis from the modified alleles allows, as described above, to identify the genes modified in individual clones, resulting in a database. This collection is the resource required to quickly generate a large number of mutant mouse strains for pharmaceutical research. Such mutant strains are an optimal tool to study the function of genes in the mouse as a mammalian model organism for human disease. The evaluation of gene function, in particular in mouse strains prone to develop a disease, allows to validate the utility of an individual gene for pharmaceutical drug development. For example, a given number of genes could be thought to be involved into insulin receptor signaling as a therapeutic target for Diabetes treatment. The generation and physiological analysis of mouse mutants for these genes would identify which gene products play a role in insulin signaling. Subsequently, drug development could be focused only on such "validated targets". Thus, within pharmaceutical drug development, mutants serve as a validation instrument to identify useful target molecules.

In addition, a subset of mutants could develop diseases, which mimic known human disorders and serve as a model for their treatment.

Once validated targets are available, the mutants can be used in combination with gene expression profiling to determine "on" and "off" target effects of candidate drugs.

Since the use of the gene trap technology is not restricted to murine ES cells and mouse mutants its application can be extended to any other vertebrate or invertebrate model organism (e.g. rats, zebra fish, *Drosophila*) to characterize the biological function of selected genes. As described above for the mouse, such mutants could be used for the validation of target genes for pharmaceutical drug development.

In another application the gene trap technology can be used to validate the utility of selected genes of plants for agricultural purposes. Plant mutants can be used to identify valuable target genes for herbicide development as well as to identify genes involved into the fertility of economically useful species.

As further exemplified in the examples below, the eGTV vectors of the invention do not only allow the identification of expressed genes in a cell but also the identification of yet unidentified, silent or poorly expressed genes. In summary, eGTVs provide superior tools for the field of genomics and functional genetical analysis.

In the following examples, material and methods of the present invention are provided. It should be understood that these examples are for illustrative purpose only and are not to be construed as limiting this invention in any manner. All publications, patents, and patent applications cited herein are hereby incorporated by reference in their entity for all purposes.

EXAMPLES

Example 1

To test the trapping efficiency of enhanced gene trap vectors, the retroviral gene trap vectors FlipROSAβgeo, eFlip3ROSAβgeo and eFlip6ROSAβgeo (FIG. 4) were equipped with a puromycin resistance gene, which is independently transcribed from a pgk promoter. This element, inserted downstream of a β-galactosidase (LacZ)-neomycin-phosphotransferase fusion gene (βgeo) flanked by SA- and polyA-sequences enables the quantification of all gene trap insertions across the genome of a target cell. Enhanced gene trap vectors contain in addition to a GDSC either 3 or 6 Oct-4 responsive elements (OREs) arranged in tandem repeats (see FIG. 4).

A. Construction of the Gene Trap Vectors FlipROSAβgeo, eFlip3ROSAβgeo and eFlip6ROSAβgeo.

Construction of the gene trap vector FlipROSAβgeo: For the construction of FlipROSAβgeo an overlap extension PCR strategy was chosen using the oligonucleotides I1 (5'-CGC CTC CTC TTC CTC CAT CC-3'; SEQ ID NO:9) and 13 (5'-ACT CTT CCG CTT CCT CGC TCC ACC GCG GCT TCG AGA CCG T-3'; SEQ ID NO:10) for amplification of the 5' f3-frt recombinase target (RT) sequences from FlipROSAβgeo(int) (see SEQ ID NO:1) and the oligonucleotides 12 (5'-GGG CCT CTT CGC TAT TAC GC-3'; SEQ ID NO:11) and 14 (5'-ACG GTC TCG AAG CCG CGG TGG AGC GAG GAA GCG GAA GAG T-3'; SEQ ID NO:12) for amplification of the 5' lox511-loxP RTs from pFIEx; Schnutgen, F. et al., Nat. Biotechnol. (2003)). The two PCR products were purified, annealed and re-amplified using the oligonucleotides I1 and I2. The resulting PCR product was cloned into the BamHI site of the retroviral vector pBABESrfI (modified from pBABE puro; see SEQ ID NO:2) (Morgenstern, J. P., Land, H., Nucl. Acids. Res. 18:3587-3596 (1990)) to obtain -pBLF5'-. Similarly, the 3' RTs were amplified with the oligonucleotides 16 (5'-GCT CCT CGC CCT TGC TCA CC-3'; SEQ ID NO:13) and 18 (5'-TAG AAG CGG TTT TCG GGA GAA TAC GAC TCA CTA TAG GGC G-3'; SEQ ID NO:14) for loxP-lox511 and with the oligonucleotides 15 (5'-TGC TGG CCT TTT GCT CAC AT-3'; SEQ ID NO:15) and 17 (5'-CGC CCT ATA GTG AGT CGT ATT CTC CCG AAA ACC GCT TCT A-3'; SEQ ID NO:16) for the frt-f3. The two products were purified, annealed and re-amplified with the oligonucleotides 16 and 17. The resulting PCR product containing all four RTs was cloned into the EcoRI restriction site of pBLF5' to obtain pBLF. The GDSC (SA-βgeo-pA) was recovered as an XhoI restriction fragment from ROSAβgeo (Friedrich, G., Soriano, P., Genes. Dev. 5:1513-1523 (1991)) and cloned into the SnaBI restriction site of pBLF to obtain the final gene trap vector -FlipROSAβgeo-. The final vector was verified by DNA sequencing (see SEQ ID NO:3).

Construction of the gene trap vector eFlip3ROSAβgeo: Oct 4 responsive elements (ORE) from the osteopontin gene (Botquin, V. et al., Genes Dev. 12:2073-90 (1998)) were obtained by annealing the oligonucleotides P5 (5'-GAT CCT GCA CTG ACC TTT CAG CTT TGT ATA ATG TAA GTT AAA ATC ACA TTT GAA ATG CAA ATG GAA AAG CA-3'; SEQ ID NO:17) and P6 (5'-GAT CTG CTT TTC CAT TTG CAT TTC AAA TGT GAT TTT AAC TTA CAT TAT ACA AAG CTG AAA GGT CAG TGC AG-3'; SEQ ID NO:18) and cloning into the BamHI/BglII sites of pEGFP-N1 resulting in pEGFP-O1. pEGFP-O2 to pEGFP-O6 was obtained by subsequent ligation of additional to pEGFP-O1. 3-6 OREs obtained from pEGFP-O3 and pEGFP-O6 were cloned as BamHI/BglII fragments into the BglII site located in the spacer between the frt and the f3 sites of FlipRosaβgeo to obtain eFlip3ROSAβgeo and eFlip6ROSAβgeo. The primary structure of the final vectors was confirmed by DNA sequencing (SEQ ID NOs:4 and 5).

B. Construction of the Gene Trap Vectors FlipROSAβ-geoPuro, eFlip3ROSA-βgeoPuro and eFlip6ROSAβgeoPuro Construction of the gene trap vector FlipROSAβgeoPuro: The puromycin cDNA was obtained from pBabePuro (Morgenstern, J. P., Land, H., Nucl. Acids. Res. 18:3587-3596 (1990)) by PCR using the primers P7 (5'-GGG GGC TGC AGA CTT ACA GCG GAT CCC CTC AGG CAC CGG GCT TGC-3'; SEQ ID NO:19) and P8 (5'-GGG GGC TGC AGC CAA TAT GAC CGA GTA CAA GCC CAC-3'; SEQ ID NO:20). The puromycin cDNA was then used to replace the neomycin resistance gene of expression plasmid pD383 (Zazopoulos, E. et al., Nature 390:311-5 (1997)), obtain pD383/puro. The pgk promoter-puro-polyA cassette of pD383/puro was cloned as a XhoI restriction fragment into a unique SadI site of FlipROSAβgeo, eFlip3ROSAβgeo and eFlip6ROSAβgeo to obtain of FlipROSAβgeoPuro, eFlip3ROSAβgeoPuro and eFlip6ROSAβgeoPuro, respectively (SEQ ID NOs:6-8).

C. Isolation of Puromycin Resistant Clones and Quantification of Gene Trap Events by LacZ Staining.

Generation of retroviral particles: Virus producer cells ($4 \times 10^5$) (Kinsella, T. M., Nolan, G. P., Hum. Gene Ther. 7:1405-13 (1996)) were seeded onto P90 dishes and grown in DMEM (high glucose) supplemented with 10% FCS, 20 mM glutamine, 1× non-essential amino acids, and 0.1 mM β-mercaptoethanol. After incubating for 3 days, the cell were transfected with the retroviral constructs using Lipofectamin 2000 (Invitrogen) and the manufacturers instructions. 48 hours later, cells were overlaid with 5 ml or ES cell medium (see below) and virus particle containing supernatants were harvested after incubating for 4.5 hours. Supernatants were filtered through a 0.45 μm Millipore filter, supplemented with 5 μg/ml Poybrene and stored at −80° C. until use.

ES cell cultures: 129/Sv/C57BL6 F1-ES-cells were grown in DMEM (high glucose) supplemented with 15% FCS, 2 mM glutamine, 20 mM HEPES, 1 mM sodium pyruvate, 1× non-essential amino acids, 0.1 mM mercapto-ethanol, and 1500 U/ml leukemia inhibitory factor (LIF) (Chemicon).

Infection of mouse embryonic stem cells: $1 \times 10^5$ ES cells were seeded onto gelatinized P60 Petri dishes and allowed to attach overnight. Cells were then exposed to 2 ml virus containing supernatant for 4.5 h. After adding 2 ml of fresh ES cell medium and incubating overnight, cells were put in selection for 12 days using ES cell medium containing either 0.6 μg/ml puromycin.

X-Gal staining: After washing in PBS, cells were fixed in 3% formaldehyde and incubated overnight in lacZ staining buffer (5 mM $K_3[Fe(CN)_6]$, 5 mM $K_4[Fe(CN)_6]$, 2 mM $MgCl_2$ in PBS) and 1.25 ml X-Gal solution (40 mg/ml in dimethylformamide).

D. Results:

Since retroviruses integrate mostly randomly throughout the genome, only a small fraction of the vectors will produce a gene trap event by inserting into an expressed gene. Gene trap events induce γ-galactosidase (LacZ) expression, which can be visualized by staining with X-Gal. Consistent with previous observations, less than 4% of all FlipROSAβ-geoPuro insertions (=number of puromycin resistant clones) generated a gene trap event (=number of LacZ+ clones) (Table 1). In contrast, over 30% of the eFlip6ROSAβgeoPuro insertions generated a gene trap event, suggesting an ORE/Oct-4 mediated induction of gene expression at the insertion site (Table 1). Since activation can involve both expressed and non-expressed genes, the vectors of the invention will (i) improve the efficiency of trapping by decreasing the threshold for reporter protein detection, and (ii) increase the fraction of genes accessible to trapping by including silent genes.

TABLE 1

Induction of gene expression by enhanced gene trap vectors*

| | FlipROSAβGeo | | eFlip3ROSAβGeo | | eFlip6ROSAβGeo | |
|---|---|---|---|---|---|---|
| Expt. | LacZ+ | total | LacZ+ | total | LacZ+ | total |
| 1 | 0 | 55 | 7 | 66 | 8 | 45 |
|   | 1 | 46 | 5 | 23 | 12 | 35 |
| 2 | 2 | 35 | 2 | 32 | 9 | 35 |
|   | 4 | 40 | 5 | 37 | 12 | 46 |

TABLE 1-continued

Induction of gene expression by enhanced gene trap vectors*

| | FlipROSAβGeo | | eFlip3ROSAβGeo | | eFlip6ROSAβGeo | |
|---|---|---|---|---|---|---|
| Expt. | LacZ+ | total | LacZ+ | total | LacZ+ | total |
| 3 | 2 | 157 | 6 | 95 | 42 | 127 |
|   | 7 | 103 | 5 | 138 | 41 | 97 |
|   | 16 | 436 | 30 | 391 | 124 | 385 |
|   | 3.7% | | 7.7% | | 32.2% | |

*F1-ES cells were infected with retrovirus particle containing supernatants from FNXEco producer cells after transiently transfecting the gene trap plasmids. After selecting in 0.8 μg/ml puromycin for 10 days, resistant clone were stained with X-Gal and counted. Results are from duplicate plates of 3 independent experiments are shown.

Example 2

Figure 4:
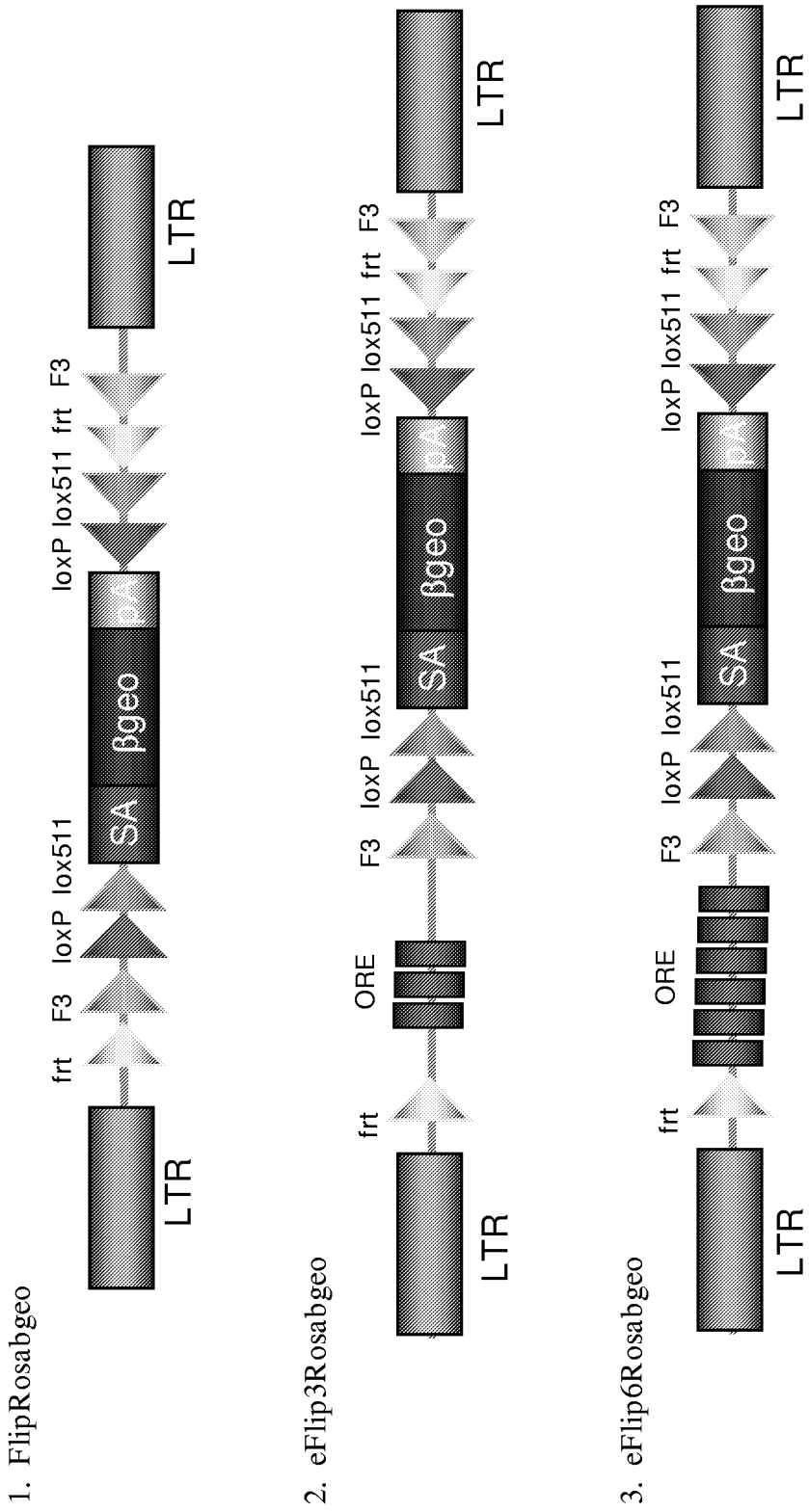
FIG. 4: Conditional gene trap vectors. (Top) classic; (Bottom) enhanced. LTR=long terminal repeat, SA=splice acceptor, βgeo=β-galactosidase/neomycin-phosphotransferase fusion gene, pA=polyadenylation sequence, ORE=Oct-4 responsive elements. Triangles represent the homotypic and heterotypic site specific recombinase recognition targets for the FLPe (frt, F3) and Cre (loxP, lox511).

To determine whether enhanced gene trap vectors trap genes more efficiently, we produced several hundreds of ES cell clones with each of the conditional gene trap vectors—FlipRosaβgeo and eFlip6Rosaβgeo—(FIG. 4). After isolating the GTSTs by 5' RACE, we determined the number of genes trapped by each vector that had not been trapped before with the collection of standard gene trap vectors used by the German Gene Trap Consortium (GGTC).

A. Isolation of Mutant ES Cell Lines Expressing FlipRosaβ-geo and eFlip6ROSAβgeo:

eFlip6ROSAβgeo gene trap virus was produced as described in Example 1B for the FlipROSAβgeoPuro class of vectors. ES cells were infected with the virus containing supernatants at an M.O.I.<0.5 as described in Example 1B. Gene trap expressing ES-cell lines were selected in 130 μg/ml G418 (Invitrogen), manually picked, expanded, and stored frozen in liquid nitrogen until use.

B. Recovery of GTSTs by 5' RACE and Database Analysis:

cDNAs were prepared from the polyadenylated RNA using a RoboAmp robotic device (MWG Biotech, Ebersberg, Germany) with a processing capacity of 96 samples/day. Samples of $2 \times 10^5$ cells were lysed in 1 ml of lysis buffer containing 100 mM Tris/HCl pH 8.0, 500 mM LiCl, 10 mM EDTA, 1% LiDS and 5 mM DTT. Polyadenylated RNA was captured from the lysates by biotin-labeled oligo-d(T)-primers according to the manufacturers instructions (Roche Diagnostics Corp., Indianapolis, Ind., USA) and placed on streptavidin-coated 96-well plates (AB Gene, Surrey, UK). After washing, solid-phase cDNA synthesis was performed in-situ using random hexamers and SuperScript II RT (Invitrogen, Karlsruhe, Germany). To remove excess primers the cDNAs were filtered through Multiscreen PCR plates (Millipore Corp. Bedford, Mass., USA). The 5" ends of the purified cDNAs were tailed with dCTPs using terminal transferase -TdT- (Invitrogen, Karlsruhe, Germany) following the manufacturer's instructions.

For PCR amplification of GTSTs, the following vector-specific primers were used: 5'-CTA CTA CTA CTA GGC CAC GCG TCG ACT AGT ACG GGI IGG GII GGG IIG-3' (SEQ ID NO:21) and 5'-GCC AGG GTT TIC CCA GTC ACG A-3" (SEQ ID NO:22); 5'-CTA CTA CTA CTA GGC CAC GCG TCG ACT AGT AC-3' (SEQ ID NO:23) and 5'-TGT AAA ACG ACG GCC AGT GTG AAG GCT GTG CGA GGC CG-3' (SEQ ID NO:24) (nested). Amplification products were directly sequenced using AB377 or ABI3700 sequencing machines (Applied Biosystems ABI, Foster City, USA).

After filtering sequences against repeats and removing all vector sequences from the GTSTs, a PHRED score was assigned to each individual nucleotide. GTSTs qualified as informative if they were at least 50 nucleotides long and exhibited a minimum mean PHRED score of 20 (FIG. 1, supplementary information). Homology searches were performed using the publicly available sequence databases and the BlastN algorithm. Databases included GenBank, UniGene, OMIM (all at http://www.ncbi.nlm.nih.gov), ENSEMBL (http://www.ensembl.org), RIKEN (http://www.rarf.riken.go.jp) and GeneOntology (http://www.geneontology.org).

C. Results:

GGTC's library is presently the largest public library of ES cell lines with gene trap insertion in single genes. It presently contains 13,616 GTSTs (www.genetrap.de) corresponding to 3,349 unique genes. Table 2 shows, that 15% of the genes trapped by eFlipRosaβgeo were not present in the database, i.e. had not been trapped before, which is almost twice as much the number of novel genes trapped by standard FlipRosaβgeo. This suggests that in ES cells the genomic target accessible to enhanced gene trap vectors is significantly larger.

TABLE 2

Trapping efficiency of novel genes by enhanced gene trap vectors as estimated by 5'RACE*

| Vector | GTSTs | Novel genes (Refseq) |
|---|---|---|
| FlipRosaβgeo | 1,766 | 145 (8%) |
| eFlip6Rosaβgeo | 1,187 | 174 (15%) |

*GTSTs recovered from FlipRosaβgeo and eFlip6Rosaβgeo expressing ES cell clones were aligned to the GGTC-GTST database using the BlastN algorithm This conclusion was re-enforced by determining the number of sentinel genes trapped by the two vectors that were not present in any gene trap resource, including the International Gene Trap Consortium's (IGTC) database with 27,000 GTSTs and Lexicon Genetics' Omnibank with 200,000 GTSTs (all available at NCBI). "Sentinel" genes are fully genome annotated genes, which are presently at 7,984 (Skarnes, W. C. et al., Nat. Genet. 24:13-4 (2000)). Table 3 shows that eFlipRosaβgeo trapped sentinel genes not present in both resources about 40% more efficiently than FlipRosaβgeo.

TABLE 3

Trapping efficiency of novel sentinel genes by enhanced gene trap vectors*

| Vector | Sentinel genes | not trapped by IGTC | not trapped by Lexicon |
|---|---|---|---|
| FlipRosaβgeo | 265 | 26 (29.8%) | 7 (2.6%) |
| eFlipRosaβgeo | 243 | 43 (17.7%) | 11 (4.5%) |

*GTSTs recovered from FlipRosaβgeo and eFlip6Rosaβgeo expressing ES cell clones corresponding to sentinel genes were aligned to the IGTC's and Lexicon's databases using the BlastN algorithm.

Example 3

The large scale recovery of GTSTs from mutant ES cell lines produced with conventional gene trap vectors relies on the PCR amplification of fusion transcripts using semiautomatic 5' RACE. The method, while generally robust, is dependent on transcript levels, which if too low preclude PCR amplification. In contrast to conventional gene trap expressing clones for which over 80% of RT-PCR amplifications were successful, less than 50% of the eGTV expressing clones gave meaningful 5' RACE amplification products, suggesting that the eGTV insertions occurred into either silent or weakly expressed genes. To test this hypothesis, we subjected 51 ES cell lines that failed to generate amplification products to genomic (inverse) PCR.

A. Recovery of GTSTs by Inverse PCR:

Genomic DNA was isolated using the DNeasy kit of Quiagen according to the manufacturers protocol. DNA was eluted in 150 µl. Approximately 3 µg genomic DNA were digested in 100 µl with 20 u NspI at 37° C. overnight. Digested DNA was purified using the Qiaquick kit according to the manufacturers protocol, ligated in 300 µl at 16° C. overnight and again purified using the Qiaquick kit.

5' inverse PCRs were carried out using the oligonucleotides I16 (5'-CGA GCC CCA GCT GGT TCT TTC-3'; SEQ ID NO:25) and SR1 (5'-GCT AGC TTG CCA AAC CTA CAG GTG G-3'; SEQ ID NO:26). Nested PCR was carried out using the oligonucleotides I15 (5'-GTC TCA GAA GCC ATA GAG CCC-3'; SEQ ID NO:27) and SR2 (5'-GCC AAA CCT ACA GGT GGG GTC TTT-3'; SEQ ID NO:28). 3' inverse PCR was carried out using the oligonucleotides I14 (5'-ACT ATC CCG ACC GCC TTA CTG C-3'; SEQ ID NO:29) and iPCRu3 (5'-CCT CCG ATT GAC TGA GTC GCC C-3'; SEQ ID NO:30). Nested PCR was carried out using the oligonucleotides I13 (5'-TGT TTT GAC CGC TGG GAT CTG C-3'; SEQ ID NO:31) and iPCRu4 (5'-TAC CCG TGT ATC CAA TAA ACC C-3'; SEQ ID NO:32).

B. Results:

Sequencing of the amplification products showed that of 25 eGTV insertions in annotated genes, 15 (60%) were novel and not present in GGTC's database, suggesting that the novel genes were either silent or poorly transcribed prior to insertion.

TABLE 3 eFlip6Rosabgeo insertions into annotated genes identified by inverse PCR

| Clone | Chromosome | Gene | Novel* |
|---|---|---|---|
| M103A02 | 5 | Add1 | no |
| M103A06 | 7 | ENSMUSG00000036862 | YES |
| M103B03 | 1 | Fbxo36 | YES |
| M103B04 | 17 | ENSMUSESTT00000012809 + ENSMUSESTT00000012808 | no |
| M103B05 | 12 | SERINE PALMITOYL-TRANSFERASE 2 | no |
| M103B06 | 4 | Perlecan | no |
| M103B07 | 11 | POTENTIAL HELICASE WITH ZINC-FINGER DOMAIN | no |
| M103C01 | 7 | ENSMUSESTG00000006748 | no |
| M103C02 | 7 | ENSMUSG00000007833 | YES |
| M103C05 | 17 | 1700061G19Rik | YES |
| M103C07 | 12 | SERINE PALMITOYL-TRANSFERASE 2 | no |
| M103D01 | 7 | ENSMUSESTT00000023443 | YES |
| M103D03 | 5 | Q8C4V2 | YES |
| M103D04 | 5 | SBBI26 HOMOLOG | YES |
| M103E01 | 17 | MYELIN-OLIGODENDROCYTE GLYCOPROTEIN PRECURSOR | YES |
| M103E02 | 11 | TUMOR DIFFERENTIALLY EXPRESSED PROTEIN 1 | YES |
| M103E03 | 19 | ENSMUSESTG00000018244 | YES |
| M103E05 | 11 | Plcd3 | YES |
| M103E06 | 12 | SERINE PALMITOYL-TRANSFERASE 2 | no |
| M103E08 | 12 | Actn1 | no |
| M103F02 | 11 | B230379M23Rik | no |
| M103F03 | 7 | ENSMUSESTG00000019374, TYPE I INOSITOL-1,4,5-TRISPHOSPHATE 5-PHOSPHATASE | YES |
| M103F04 | 7 | 2410004H02Rik, Aldehydedehydrogenase | YES |

TABLE 3-continued eFlip6Rosabgeo insertions into annotated
genes identified by inverse PCR

| Clone | Chromo-some | Gene | Novel* |
|---|---|---|---|
| M103F05 | 8 | ENSMUSESTG00000004620 | YES |
| M103F06 | 8 | GH REGULATED TBC PROTEIN 1 | YES |

*refers to genes not present in the GGTC database.

Example 4

Figure 5:
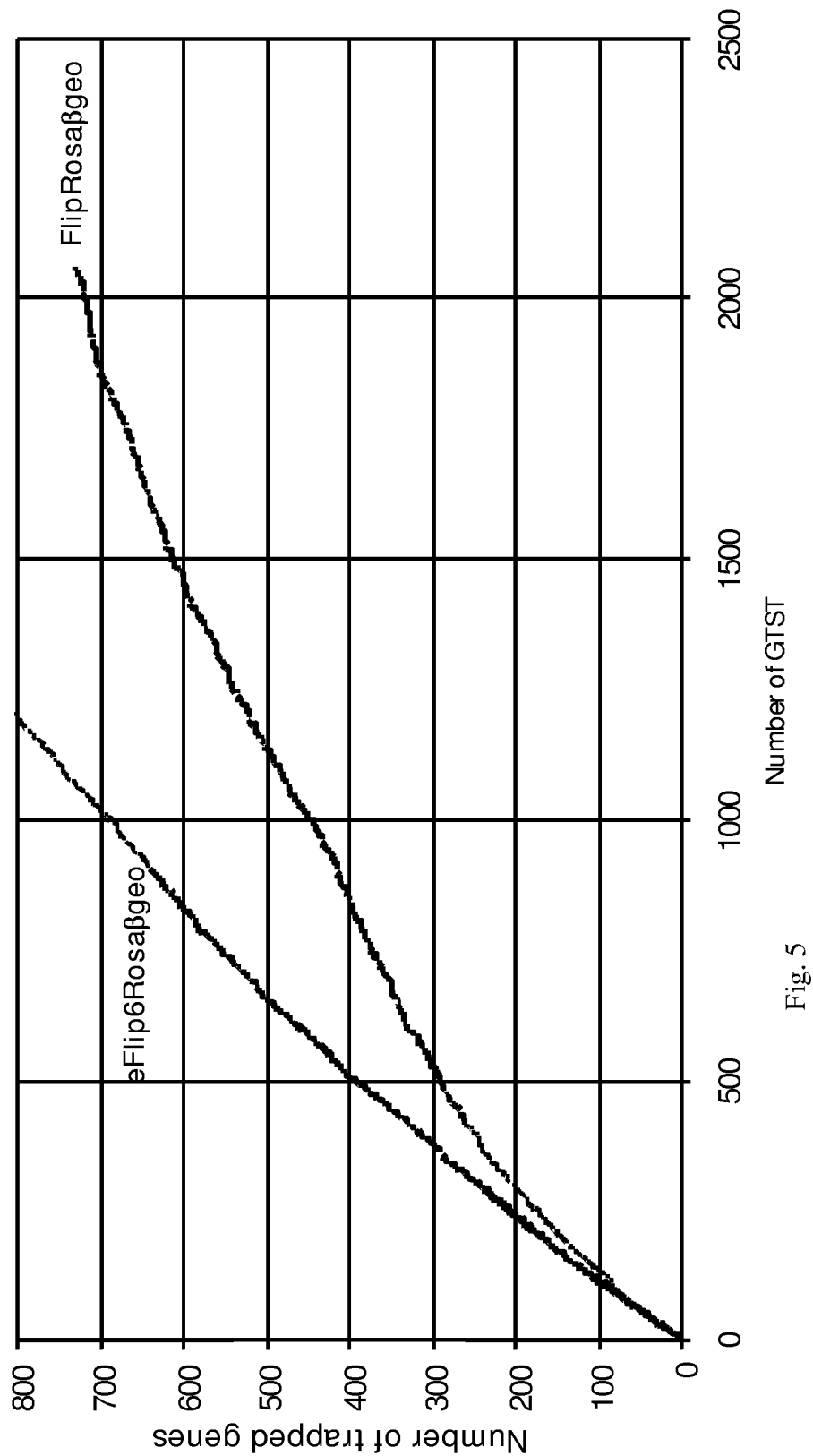
FIG. 5: Comparative rates of trapping exhibited by enhanced and non-enhanced gene trap vectors. Unique genes were identified by blasting (BLASTN) the GTSTs against the RefSeq database. The number of novel genes among accumulating insertions was determined chronologically.

This example describes the comparative rate of trapping of the FlipROSAβgeo and eFlip6ROSAβgeo gene trap vectors. FIG. 5 shows that at average eFlip6ROSAβgeo traps a novel gene in with every 1.4 insertions. In contrast, the non-enhanced FlipROSAβgeo requires 2.8 insertions to trap a novel gene, clearly indicating that the enhancer elements in the eFlip6ROSAβgeo gene trap vector significantly improve the efficiency of trapping.

Example 5

This example describes another enhanced gene trap vector of the invention containing the cytomegalo-virus (CMV) immediate early enhancer which is essentially ubiquitous. This enhancer has been shown to activate gene expression in embryonic stem cells (Chung, S. et al., Stem Cells 20:139-45 (2002)) and in all mouse tissues in either orientation and up to a distance of several kbp from the promoter (Dorsch-Hasler, K. et al., Proc. Natl. Acad. Sci. USA 82:8325-9 (1985)). The CMV enhancer has been used in combination with the chicken 6-actin promoter to drive the expression of transgenes in the mouse (Rodriguez, C. I. et al., Nat. Genet. 25:139-40 (2000); Zong H. et al., Cell 121:479-492 (2005); Okabe M. et al., FEBS Lett. 407:313-319 (1997)).

Example 6

This example describes another enhanced gene trap vector of the invention containing the enhancer from the mouse embryonic stem cell virus. This virus is a synthetic retrovirus derived from a mutant myeloproliferative sarcoma virus (PCMV). The enhancer element of this virus is demonstrated activity in embryonic carcinoma cells as well as embryonic stem cells[21].

Example 7

This example described the use of trapped ES cell lines for making mutant mice. ES-cell derived chimeras were generated by injecting C57Bl/6 blastocysts with ES cells from the following trapped lines as obtained in Example 2: P015F03 P016F03, P023A01, P023F01, Q001D04, and Q016D06. Male chimeras were obtained with each clone and were bred to C57Bl/6 females. Litters were analyzed for germline transmission using the agouti coat color marker and tail blotting. So far, the clones P015F03 and P016F03 generated transmitted the mutation to the F1 generation. F1 mice were intercrossed to obtain homozygous (mutant) F2 offspring for phenotype analysis.

---

The invention claimed is:

1. A gene trap vector comprising a gene disruption and selection cassette (GDSC) and one or more non-viral, cell-type-specific enhancer elements that are active in mammalian cells, wherein said GDSC comprises a promoterless reporter gene and/or a promoterless selectable marker gene flanked upstream by a 3' splice acceptor (SA) site and downstream by a transcriptional termination polyA sequence.

2. The gene trap vector of claim 1, wherein the vector is a plasmid.

3. The gene trap vector of claim 1, wherein said one or more non-viral, cell-type-specific enhancer elements
 (i) are located upstream of the GDSC, and/or
 (ii) are located downstream of the GDSC.

4. The gene trap vector of claim 1, wherein the one or more non-viral, cell-type-specific enhancer elements contain at least one binding site for a transcription activating factor.

5. The gene trap vector of claim 1, wherein the one or more non-viral, cell-type-specific enhancer elements contain binding sites that bind transcription activation factors in a sequence-specific manner.

6. The gene trap vector of claim 5, wherein the binding sites are arranged as tandem repeats.

7. The gene trap vector of claim 1, wherein the one or more non-viral, cell-type-specific enhancer elements are selected from the group consisting of hormone responsive elements and transcription factor binding elements.

8. The gene trap vector of claim 1, wherein the one or more non-viral, cell-type-specific enhancer elements are tandem repeats that comprise a transcription factor binding site selected from the group consisting of NF-kB, Oct2, Oct3, and Oct4 transcription factor binding sites.

9. The gene trap vector of claim 8, wherein the transcription factor binding sites are the Oct-4 transcription factor binding sites.

10. The gene trap vector of claim 9, wherein the Oct-4 transcription factor binding site are inserted between two homotypic or heterotypic site-specific recombination targets.

11. The gene trap vector of claim 1, wherein the reporter gene is a R-galactosidase neomycinphosphotransferase fusion gene.

12. The gene trap vector of claim 1, further comprising a puromycin resistance gene inserted upstream or downstream of the GDSC.

13. The gene trap vector of claim 12, wherein the puromycin resistance gene is in direct or inverse transcriptional orientation relative to the GDSC.

14. The gene trap vector of claim 1, further comprising site-specific recombinase recognition elements that are oriented in opposing directions and flank the GDSC and the one or more enhancer elements such that inversion of the GDSC and the one or more enhancer element is mediated in the presence of the site-specific recombinase.

15. The gene trap vector of claim 14, wherein the recombinase is a Cre or a Flp recombinase.

16. The gene trap vector of claim 1, wherein the vector comprises a 5' and a 3' nucleotide sequence homologous to the 5' and the 3' sequence of an intron of a target gene, wherein the nucleotide sequences flank the GDSC and the one or more non-viral, cell-type-specific enhancer elements and further mediate homologous recombination at the intron.

17. A mammalian cell comprising the gene trap vector of claim 1.

18. A retroviral gene trap vector comprising a GDSC and one or more cell-type-specific enhancer elements that are active in mammalian cells, wherein said GDSC comprises a promoterless reporter gene and/or a promoterless selectable marker gene flanked upstream by a 3' splice acceptor (SA) site and downstream by a transcriptional termination polyA sequence.

19. The retroviral gene trap vector of claim 18, which is eFlip3ROSApgeo or eFlip6ROSApgeo having the nucleotide sequence of SEQ ID Nos:4 and 5, respectively.

* * * * *